US008632838B2

(12) United States Patent
Roth et al.

(10) Patent No.: US 8,632,838 B2
(45) Date of Patent: Jan. 21, 2014

(54) ARTICLES HAVING NON-FOULING SURFACES AND PROCESSES FOR PREPARING THE SAME INCLUDING PRETREATMENT OF ARTICLES

(75) Inventors: Laurence A. Roth, Cambridge, MA (US); Zheng Zhang, Cambridge, MA (US); Chad C. Huval, Cambridge, MA (US); Michael A. Bouchard, Cambridge, MA (US); Christopher R. Loose, Cambridge, MA (US)

(73) Assignee: Semprus Biosciences Corporation, Cambridge, MA (US)

( * ) Notice: Subject to any disclaimer, the term of this patent is extended or adjusted under 35 U.S.C. 154(b) by 24 days.

(21) Appl. No.: 13/156,772

(22) Filed: Jun. 9, 2011

(65) Prior Publication Data
US 2011/0305895 A1    Dec. 15, 2011

Related U.S. Application Data

(60) Provisional application No. 61/353,200, filed on Jun. 9, 2010.

(51) Int. Cl.
*B05D 3/10* (2006.01)
*B32B 5/16* (2006.01)

(52) U.S. Cl.
USPC ............ 427/2.1; 427/299; 427/307; 427/322; 428/323

(58) Field of Classification Search
USPC .................... 428/323; 427/2.1, 299, 307, 322
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson et al. | |
| 4,480,011 A | 10/1984 | Durand et al. | |
| 4,636,208 A | 1/1987 | Rath | |
| 4,877,864 A | 10/1989 | Wang et al. | |
| 5,002,794 A | 3/1991 | Ratner et al. | |
| 5,013,649 A | 5/1991 | Wang et al. | |
| 5,180,375 A | 1/1993 | Feibus | |
| 5,453,467 A | 9/1995 | Bamford et al. | |
| 5,661,007 A | 8/1997 | Wozney et al. | |
| 5,688,678 A | 11/1997 | Hewick et al. | |
| 5,739,236 A | 4/1998 | Bowers et al. | |
| 5,844,016 A | 12/1998 | Sawhney et al. | |
| 5,866,113 A | 2/1999 | Hendriks et al. | |
| 5,997,895 A | 12/1999 | Narotam et al. | |
| 6,054,504 A | 4/2000 | Dalla Riva Toma | |
| 6,150,459 A | 11/2000 | Mayes et al. | |
| 6,177,406 B1 | 1/2001 | Wang et al. | |
| 6,200,338 B1 * | 3/2001 | Solomon et al. ............ | 623/1.34 |
| 6,358,557 B1 | 3/2002 | Wang et al. | |
| 6,395,800 B1 | 5/2002 | Jones et al. | |
| 6,432,919 B1 | 8/2002 | Wang et al. | |
| 6,534,268 B1 | 3/2003 | Kawai et al. | |
| 6,711,879 B2 | 3/2004 | Korteweg et al. | |
| 7,087,658 B2 | 8/2006 | Swan et al. | |
| 7,220,491 B2 | 5/2007 | Rouns et al. | |
| 7,238,364 B2 | 7/2007 | Sawhney et al. | |
| 7,238,426 B2 | 7/2007 | Jiang et al. | |
| 7,276,286 B2 | 10/2007 | Chapman et al. | |
| 7,306,625 B1 | 12/2007 | Stratford et al. | |
| 7,431,888 B2 | 10/2008 | Frechet et al. | |
| 2001/0050749 A1 | 12/2001 | Wanatabe | |
| 2003/0021823 A1 | 1/2003 | Landers et al. | |
| 2003/0143335 A1 | 7/2003 | Qiu et al. | |
| 2004/0256232 A1 | 12/2004 | Jiang et al. | |
| 2006/0057180 A1 | 3/2006 | Chilkoti et al. | |
| 2006/0217285 A1 | 9/2006 | Destarac | |
| 2007/0048249 A1 | 3/2007 | Youngblood et al. | |
| 2007/0104891 A1 | 5/2007 | Fournand et al. | |
| 2007/0254006 A1 | 11/2007 | Loose et al. | |
| 2008/0181861 A1 | 7/2008 | Jiang et al. | |
| 2008/0255305 A1 | 10/2008 | Brook et al. | |
| 2009/0155335 A1 * | 6/2009 | O'Shaughnessey et al. . | 424/423 |
| 2009/0197791 A1 | 8/2009 | Balastre et al. | |
| 2009/0311301 A1 | 12/2009 | Kleiner et al. | |
| 2010/0035074 A1 | 2/2010 | Cohen et al. | |
| 2010/0072642 A1 | 3/2010 | Broad et al. | |
| 2010/0099160 A1 | 4/2010 | Jiang et al. | |

FOREIGN PATENT DOCUMENTS

| | | | |
|---|---|---|---|
| WO | 03/000433 A1 | 1/2003 | |
| WO | 2007/002493 A2 | 1/2007 | |
| WO | 2007/024393 A2 | 3/2007 | |
| WO | 2007/095393 A2 | 8/2007 | |
| WO | 2008/006911 A2 | 1/2008 | |
| WO | 2008/019381 A2 | 2/2008 | |

(Continued)

OTHER PUBLICATIONS

Patent Cooperation Treaty, International Search Report issued for PCT/US2011/039799, mailed Feb. 23, 2012, 3 pages.
Patent Cooperation Treaty, International Search Report issued for PCT/US2011/039806, mailed Mar. 12, 2012, 4 pages.
Patent Cooperation Treaty, International Search Report issued for PCT/US2011/039815, mailed Feb. 24, 2012, 3 pages.
Vermette, P. et al., Tissue Engineering Intelligence Unit 6, Biomedical Applications of Polyurethanes, Chapter 7, 2001, 175-211.
Salim, M. et al., Studies of electroosmotic flow and the effects of protein adsorption in plasma-polymerized microchannel surfaces, Electrophoresis, 2009, 30, 1877-1887.
Bell, C.; Peppas, N., Biomedical membranes from hydrogels and interpolymer complexes. Biopolymers II 1995, 122, 125-175.

(Continued)

*Primary Examiner* — Cachet Sellman
(74) *Attorney, Agent, or Firm* — Bryan Cave LLP

(57) ABSTRACT

Processes are described herein for preparing medical devices and other articles having a low-fouling surface on a substrate comprising a polymeric surface. The polymeric surface material may possess a range of polymeric backbones and substituents while providing the articles with a highly efficient, biocompatible, and non-fouling surface. The processes involve treating the substrate to reduce the concentration of chemical species on the surface of or in the substrate without altering the bulk physical properties of the device or article, and thereafter forming a grafted polymer layer on the treated substrate surface.

44 Claims, No Drawings

(56) References Cited

FOREIGN PATENT DOCUMENTS

| WO | 2008/083390 A2 | 7/2008 |
|---|---|---|
| WO | 2009-079664 A1 | 6/2009 |
| WO | 2009/085096 A2 | 7/2009 |

OTHER PUBLICATIONS

Chapman, R. G.; Ostuni, E.; Liang, M. N.; Meluleni, G.; Kim, E.; Yan, L.; Pier, G.; Warren, H. S.; Whitesides, G. M., Polymeric Thin Films That Resist the Adsorption of Proteins and the Adhesion of Bacteria. Langmuir 2001, 17 (4), 1225-1233.

Cheng, G.; Li, G.; Xue, H.; Chen, S.; Bryers, J. D.; Jiang, S., Zwitterionic carboxybetaine polymer surfaces and their resistance to long-term biofilm formation. Biomaterials 2009, 30 (28), 5234-40.

Cheng, G.; Zhang, Z.; Chen, S.; Bryers, J. D.; Jiang, S., Inhibition of bacterial adhesion and biofilm formation on zwitterionic surfaces. Biomaterials 2007, 28 (29), 4192-4199.

Du, H.; Chandaroy, P.; Hui, S. W., Grafted poly-(ethylene glycol) on lipid surfaces inhibits protein adsorption and cell adhesion. Biochimica et Biophysica Acta (BBA)—Biomembranes 1997, 1326 (2), 236-248.

Feng, W.; Brash, J.; Zhu, S., Atom-Transfer Radical Grafting Polymerization of 2-Methacryloyloxyethyl Phosphorycholine from Silicon Wafer Surfaces. Journal of Polymer Science Part A: Polymer Chemistry 2004, 42, 2931-2942.

Goda, T.; Konno, T.; Takai, M.; Moro, T.; Ishihara, K., Biomimetic phosphorylcholine polymer grafting from polydimethylsiloxane surface using photo-induced polymerization. Biomaterials 2006, 27 (30), 5151-60.

Harder, P.; Grunze, M.; Dahint, R.; Whitesides, G. M.; Laibinis, P. E., Molecular Conformation in Oligo(ethylene glycol)-Terminated Self-Assembled Monolayers on Gold and Silver Surfaces Determines Their Ability to Resist Protein Adsorption. The Journal of Physical Chemistry B 1998, 102 (2), 426-436.

Haynie, S. L.; Crum, G. A.; Doele, B. A., Antimicrobial activities of amphiphilic peptides covalently bonded to a water-insoluble resin. Antimicrobial Agents and Chemotherapy 1995, 39 (2), 301-307.

Ignatova et al., Combination of Electrografting and Atom-Transfer Radical Polymerization for Making the Stainless Steel Surface Antibacterial and Protein Antiadhesive. Langmuir 2005, 22 (1), 255-262.

Ishihara, K.; Iwasaki, Y.; Ebihara, S.; Shindo, Y.; Nakabayashi, N., Photoinduced graft polymerization of 2-methacryloyloxyethyl phosphorylcholine on polyethylene membrane surface for obtaining blood cell adhesion resistance. Colloids Surf B Biointerfaces 2000, 18 (3-4), 325-335.

Yuan, J.; Zhang, J.; Zang, X.; Shen, J.; Lin, S., Improvement of blood compatibility on cellulose membrane surface by grafting betaines. Colloids and Surfaces B: Biointerfaces 30.

Jiang, Y.; Rongbing, B.; Ling, T.; Jian, S.; Sicong, L., Blood compatibility of polyurethane surface grafted copolymerization with sulfobetaine monomer. Colloids Surf B Biointerfaces 2004, 36 (1), 27-33.

Jin, Z.; Feng, W.; Beisser, K.; Zhu, S.; Sheardown, H.; Brash, J. L., Protein-resistant polyurethane prepared by surface-initiated atom transfer radical graft polymerization (ATRgP) of water-soluble polymers: effects of main chain and side chain lengths of grafts. Colloids Surf B Biointerfaces 2009, 70 (1), 53-9.

Jin, Z.; Feng, W.; Zhu, S.; Sheardown, H.; Brash, J. L., Protein-resistant polyurethane via surface-initiated atom transfer radical polymerization of oligo(ethylene glycol) methacrylate. J Biomed Mater Res A 2009, 91 (4), 1189-201.

Zhang, J.; Yuan, J.; Yuan, Y.; Shen, J.; Lin, S., Chemical modification of cellulose membranes with sulfo ammonium zwitterionic vinyl monomer to improve hemocompatibility. Colloids and Surfaces B: Biointerfaces 30.

Jun, Z.; Youling, Y.; Kehua, W.; Jian, S.; Sicong, L., Surface modification of segmented poly(ether urethane) by grafting sulfo ammonium zwitterionic monomer to improve hemocompatibilities. Colloids and Surfaces B: Biointerfaces 2003, 28 (1), 1-9.

Kang, E. T.; Tan, K. L.; Liaw, D. J.; Chiang, H. H., Surface modification and functionalization of electroactive polymer films via grafting of polyelectrolyte, polyampholyte and polymeric acids. Journal to Materials Science 1996, 31, 1295-1301.

Keiji Fujimoto, Y. T., Hiroyuki Inoue, Yoshito Ikada, Ozone-induced graft polymerization onto polymer surface. J Polym Sci A Polym Chem 1993, 31, 1035-1043.

Kildal, K.; Olafsen, K.; Stori, A., Peroxide-initiated grafting of acrylamide on to polyethylene surfaces. Journal of Applied Polymer Science 1992, 44 (11), 1893-1898.

Liu, P.-S.; Chen, Q.; Liu, X.; Yuan, B.; Wu, S.-S.; Shen, J.; Lin, S.-C., Grafting of Zwitterion from Cellulose Membranes via ATRP for Improving Blood Compatibility. Biomacromolecules 2009, 10 (10), 2809-2816.

Massia, S. P.; Stark, J., Immobilized RGD peptides on surface-grafted dextran promote biospecific cell attachment. J Biomed Mater Res 2001, 56 (3), 390-9.

Michel, R.; Pasche, S.; Textor, M.; Castner, D. G., Influence of PEG Architecture on Protein Adsorption and Conformation. Langmuir 2005, 21 (26), 12327-12332.

Sakharov Am, M. L., Skibida Ip, Catalytic oxidative deformylation of polyethylene glycols with the participation of molecular oxygen. Kinet Catal 2001, 42, 662-668.

Villa-Diaz, L. G.; Nandivada, H.; Ding, J.; Nogueira-de-Souza, N. C.; Krebsbach, P. H.; O'Shea, K. S.; Lahann, J.; Smith, G. D., Synthetic polymer coatings for long-term growth of human embryonic stem cells. Nat Biotechnol 2010, 28 (6), 581-3.

West, S. L.; Salvage, J. P.; Lobb, E. J.; Armes, S. P.; Billingham, N. C.; Lewis, A. L.; Hanlon, G. W.; Lloyd, A. W., The biocompatibility of crosslinkable copolymer coatings containing sulfobetaines and phosphobetaines. Biomaterials 2004, 25 (7-8), 1195-1204.

Wozney, J. M.; Rosen, V.; Celeste, A. J.; Mitsock, L. M.; Whitters, M. J.; Kriz, R. W.; Hewick, R. M.; Wang, E. A., Novel regulators of bone formation: molecular clones and activities. Science 1988, 242 (4885), 1528-1534.

Yuan, Y.; Ai, F.; Zang, X.; Zhuang, W.; Shena, J.; Lin, S., Polyurethane vascular catheter surface grafted with zwitterionic sulfobetaine monomer activated by ozone. Colloids and Surfaces B: Biointerfaces 35.

Yuan, J.; Chen, L.; Jiang, X.; Shen, J.; Lin, S., Chemical graft polymerization of sulfobetaine monomer on polyurethane surface for reduction in platelet adhesion. Colloids Surf B Biointerfaces 2004, 39 (1-2), 87-94.

Yuan, J.; Zhang, J.; Zhou, J.; Yuan, Y. L.; Shen, J.; Lin, S. C., Platelet adhesion onto segmented polyurethane surfaces modified by carboxybetaine. J Biomater Sci Polym Ed 2003, 14 (12), 1339-49.

Yuan, Y.; Ai, F.; Zhang, X.; Shen, J.; Lin, S., Grafting Sulfobetaine monomer onto the segmented poly(ether-urethane) surface to improve hemocompatibility. J Biomaterial Sci Polym Ed 2002, 13, 1081-92.

Yuan, Y.; Zhang, J.; Ai, F.; Yuan, J.; Zhou, J.; Shen, J.; Lin, S., Surface modification of SPEC films by ozone induced graft copolymerization to improve hemocompatibility. Colloids and Surfaces B: Biointerfaces 2003, 29, 247-256.

Zhang, V., Cheng, Yang, Xue, Jiang, Nonfouling Behavior of Polycarboxybetaine-Grafted Surfaces: Structural and Environmental Effects—Biomacromolecules (ACS Publications). Biomacromolecules (Web): Sep. 12, 2008, 10, 2686-92.

Zhang, Z.; Chen, S.; Chang, Y.; Jiang, S., Surface grafted sulfobetaine polymers via atom transfer radical polymerization as superlow fouling coatings. J Phys Chem B 2006, 110 (22), 10799-804.

Zhang, Z.; Zhang, M.; Chen, S.; Horbett, T. A.; Ratner, B. D.; Jiang, S., Blood compatibility of surfaces with superlow protein adsorption. Biomaterials 2008, 29 (32), 4285-91.

Zhang, Z.; Chao, T.; Chen, S.; Jiang, S., Superlow Fouling Sulfobetaine and Carboxybetaine Polymers on Glass Slides. Langmuir 2006, 22 (24), 10072-10077.

Jiang, Zwitterionic Separation Materials for Liquid Chromatography and Capillary Electrophoresis Synthesis, Characterization and Application for Inorganic Ion and Biomolecule Separations, PhD Dissertation, Umeå University, Umeå, Sweden, 63 pages.

Odian, Principles of Polymerization, 3rd Edition, 1 page.

* cited by examiner

ARTICLES HAVING NON-FOULING SURFACES AND PROCESSES FOR PREPARING THE SAME INCLUDING PRETREATMENT OF ARTICLES

FIELD OF THE INVENTION

The present invention generally relates to articles of manufacture, such as medical devices, having a non-fouling surface comprising a grafted polymer layer. The surface resists the adhesion of biological material. The present invention also relates to processes for preparing such articles.

BACKGROUND OF THE INVENTION

Many different materials have been investigated to resist non-specific protein adsorption. Chemistries utilized for this purpose include, but are not limited to: polyethers (e.g., polyethylene glycol), polysaccharides such as dextran, hydrophilic polymers such as polyvinylpyrrolidone or hydroxyethyl-methacrylate, heparin, intramolecular zwitterions or mixed charge materials, and hydrogen bond accepting groups such as those described in U.S. Pat. No. 7,276,286. The ability of these materials in preventing protein adsorption varies greatly between the chemistries. Of these materials, only a few resist fouling to the degree required for short-term in vivo application. However, the few materials appropriate for short-term application, when used for longer periods of time in complex media or in vivo, exhibit significant fouling or other degradation, making them unsuitable for long-term applications. Furthermore, surfaces coated with materials that resist in vivo degradation are often susceptible to a noticeable decrease in fouling resistance over time.

WO 2007/02493 describes grafting sulfobetaine and carboxybetaine from self-assembled monolayers on gold substrates or from silyl groups on glass substrates using atom transfer radical polymerization (ATRP). Gold and glass are not appropriate substrates for many medical devices used in vivo. Self-assembled monolayers, such as thiol-based monolayers, may be unstable since the thiol group is not stably bound to the substrate.

U.S. Pat. No. 6,358,557 to Wang et al. describes the graft polymerization of substrate surfaces, but not with a high density of a highly non-fouling polymeric material. A thermal initiator is used to initiate polymerization, typically at temperatures greater than 85° C. Such temperatures are generally not suitable for many medical devices, such as thin-walled polyurethane catheters. Further, the "salt out" method described is generally not suitable for grafting polymers such as zwitterionic polymers.

Jian et al., Colloids and Surfaces B: Biointerfaces 28, 1-9 (2003) describes the surface modification of segmented poly (ether urethane) by grafting sulfobetaine zwitterionic monomer, but not with a high density of non-fouling material. The resulting materials are not sufficiently non-fouling to be useful in medical device applications.

Resistance of protein fouling in biocompatible solid surfaces can play an important role in a range of technological disciplines, including biotechnology, medicine, food processing, and pharmaceutical applications, to name a few. It is well known, for example, that protein adsorption and bacterial adhesion and colonization can result in infection and subsequent failure of implanted medical devices. Incidences of protein adsorption and fouling can be minimized by changing the physical and/or chemical properties of the biomaterial surface. This may include, for example, the employment of polymeric substrate surfaces that are resistant to biomaterials.

Although advances have been made in biomolecule-resistant polymer coatings generally, various flaws can be present in the surface structure of biocompatible materials, both globally and at particular locations and regions of the surface (whether a non-polymeric substrate surface, a polymeric substrate or polymer substrate coating). Such flaws may be the result of improper handling or artifacts of the manufacturing or polymerization process, or may be present on a substrate surface prior to polymer growth and/or deposition. Regardless of their source, such flaws can substantially limit the effectiveness of conventional polymer coatings and polymeric substrate surfaces. For instance, increased or decreased protein adsorption may result from changes in one or more of the specific chemical, morphological, and physical properties of the substrate or substrate coating. In general, the present invention is directed to processes for preparing articles having improved surfaces that will serve as substrates for non-fouling grafted polymer layers.

SUMMARY OF THE INVENTION

Among the various aspects of the present invention is the provision of medical devices and other articles having a low-fouling surface on a substrate comprising a polymeric surface. The polymeric surface material may possess a range of polymeric backbones and substituents while providing the articles with a highly efficient, biocompatible, and non-fouling surface.

Among the various aspects of the present invention may be noted the provision of processes for preparing an article having a low-fouling surface on a substrate comprising a polymeric surface. Also noted are the provision of articles, such as medical devices, having a non-fouling surface comprising a grafted polymeric material.

One aspect of the present invention is directed to a process for preparing an article having a low-fouling surface on a substrate. The substrate has a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to remove the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 μg/ml fibrinogen derived from human plasma and 1.4 μg/ml I-125 radiolabeled fibrinogen. In one embodiment, the treated surface and the grafted polymer layer, in combination, constitute a low-fouling surface having a fibrinogen adsorption of less than about 90 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen. In another embodiment, the treated surface and the grafted polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen. In another embodiment, the treated surface and the grafted polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen.

Another aspect of the present invention is directed to an article of manufacture comprising a substrate having a surface and a grafted polymer layer on the substrate surface. The substrate further comprising a bulk beneath the substrate surface, and a near-surface zone lying between the substrate surface and the bulk, the substrate surface, near-surface zone and bulk containing a composite comprising a continuous phase of a first material and particles of a second material dispersed in the continuous phase, the first material being polymeric and the first and second material being different, the particles having an average particle size and a distribution such that the number density of the particles in the near-surface zone is less than the overall number density of the particles in the composite, the near-surface zone extending a distance, D, from the substrate surface and into the substrate, D having a value that does not exceed twice the average particle size, the substrate surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 μg/ml fibrinogen derived from human plasma and 1.4 μg/ml I-125 radiolabeled fibrinogen. In one embodiment, the substrate surface and the grafted polymer layer, in combination, constitute a low-fouling surface having a fibrinogen adsorption of less than about 90 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen. In another embodiment, the substrate surface and the grafted polymer layer, in combination, constitute a modified surface having a fibrinogen adsorption of less than about 70 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen. In another embodiment, the substrate surface and the grafted polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 μg/mL fibrinogen derived from human plasma and 1.4 μg/mL I-125 radiolabeled fibrinogen. In each of the foregoing aspects and embodiments of the invention, preferably the article (i) is other than a non-luminal polyurethane rod and (ii) has a length greater than 5 centimeters when the article is a double lumen catheter.

Other objects and features will be in part apparent and in part pointed out hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono or polycyclic such as fused, bridging, or spiro-fused polycyclic), or a combination thereof. Unless otherwise specified, aliphatic groups contain 1-20 carbon atoms.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety —NR$^1$R$^2$ wherein R$^1$, and R$^2$ are independently hydrogen, hydrocarbyl, substituted hydrocarbyl or heterocyclo.

Ammonium: unless otherwise indicated, the term "ammonium" as used herein alone or as part of another group denotes the moiety —N$^+$R$^1$R$^2$R$^3$ wherein R$^1$, R$^2$ and R$^3$ are independently hydrogen, hydrocarbyl, substituted hydrocarbyl or heterocyclo.

Amide or Amido: unless otherwise indicated, the "amide" or "amido" moieties represent a group of the formula —CONR$^1$R$^2$ wherein R$^1$ and R$^2$ are as defined in connection with the term "amino." "Substituted amide," for example, refers to a group of the formula —CONR$^1$R$^2$ wherein at least one of R$^1$ and R$^2$ are other than hydrogen. "Unsubstituted amido," for example, refers to a group of the formula —CONR$^1$R$^2$, wherein R$^1$ and R$^2$ are each hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing an anion or other anionic species, e.g., a group that is present in a negatively charged state or in a non-charged state, but in the non-charged state is capable of becoming negatively charged, e.g., upon removal of an electrophile (e.g., a proton (H+), for example in a pH dependent manner) or a protecting group (e.g., a carboxylic acid ester), or the addition of a nucleophile. In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, sulfonic acids, phosphates, and sulfonamides.

Anionic species or Anionic moiety: unless otherwise indicated, an "Anionic species" or an "Anionic moiety" is a group, residue or molecule that is present in a negatively charged or non-charged state, but in the non-charged state is capable of becoming negatively charged, e.g., upon removal of an electrophile (e.g., a proton (H+), for example in a pH dependent manner) or other protecting group (e.g., a carboxylic acid ester), or the addition of a nucleophile. In certain instances, the group, residue or molecule is substantially negatively charged at an approximately physiological pH but undergoes protonation and becomes substantially neutral at a weakly acidic pH.

Antibiofilm activity: unless otherwise indicated, "antibiofilm activity" may be quantified, for example, using a standard continuous flow assay. In one such assay, samples may be pre-incubated with 50% fetal bovine serum for 18-20 hours at 120 RPM at 37° C. Following preincubation, samples are then exposed to a subculture of bacteria via a modified CDC (mCDC) to make a bacterial suspension of $10^6$ Cfu/mL in 1×PBS. The reactor is run in batch mode for 2 hours at 37° C. with agitation. Thereafter, the samples are transferred to a fresh reactor a suitable growth media for where flow of the sterile media (8 mL/min) runs 20-23 hours with agitation. In one preferred embodiment, the bacterial strain is *Staphylococcus epidermidis* (*S. epidermidis*, ATCC 35984), and the growth media used is 1:10 Tryptic soy broth (TSB)+0.25 wt % glucose. In an alternate preferred embodiment, the bacterial strain is *Escherichia coli* (*E. coli*, ATCC 25922) and the growth media is M63 media supplemented with 1 mM $MgSO_4$, 0.2% glucose, and 0.5% casamino acids. After incubation, the samples are rinsed five times in 100 mL of 1×PBS to remove bacteria not tightly attached. Then, accumulated bacteria on materials are macroscopically rated for biofilm surface coverage and are removed by sonication in a new solution of PBS and the total number of bacterial cells quantified through dilution plating. Preferably at least a 1, 2, 3 or 4 log reduction in bacterial count is found on the article with the non-fouling polymer layer relative to a reference substrate, that is, the same or an otherwise functionally equivalent substrate lacking the non-fouling polymer layer. An article that has a 1 log reduction in adhered bacteria relative to a reference substrate is said to have antibiofilm activity of 1 log. An article that has a 2 log reduction in adhered bacteria relative to a reference substrate is said to have antibiofilm activity of 2 log, and so forth.

Antimicrobial: unless otherwise indicated, "antimicrobial" refers to molecules and/or compositions that kill (i.e., microbicidal), inhibit the growth of (i.e., microbistatic), and/or prevent fouling by, microorganisms including bacteria, yeast, fungi, mycoplasma, viruses or virus infected cells, and/or protozoa. Antimicrobial activity with respect to bacteria may be quantified, for example, using a standard assay. In one such assay, samples may be pre-incubated with 50% fetal bovine serum for 18-20 hours at 120 RPM at 37° C. Following pre-incubation, samples are placed in *Staphylococcus aureus* (*S. aureus*, ATCC 25923) which has been diluted from an overnight culture to a planktonic concentration of $1-3\times10^5$ CFU/mL in 1% tryptone soy broth (TSB) diluted in 1×PBS or other suitable media. Samples are incubated with bacteria for 24-26 hrs with agitation (120 rpm) at 37° C. The concentration of TSB or other media can vary with the organism being used. After incubation, the samples are placed in 3 mL PBS for 5 min at 240 RPM at 37° C. to remove bacteria not tightly attached to the material. Then, accumulated bacteria on materials are removed by sonication in a new solution of PBS and the total number of bacterial cells are quantified through dilution plating. Preferably at least a 1, 2, 3 or 4 log reduction in bacterial count occurs relative to colonization on a reference substrate, that is, the same or an otherwise functionally equivalent substrate lacking the non-fouling polymer layer. A surface that has a lower bacterial count on it than the reference substrate may be said to reduce microbial colonization.

Antimicrobial peptide (AmP): unless otherwise indicated, "antimicrobial peptide" (or "AmP") refers to oligopeptides, polypeptides, or peptidomimetics that kill (i.e., are microbicidal) or inhibit the growth of (i.e., are microbistatic) microorganisms including bacteria, yeast, fungi, mycoplasma, viruses or virus infected cells, and/or protozoa.

Anti-thrombogenic: unless otherwise indicated, "anti-thrombogenic" refers to the ability of a composition to resist thrombus formation. Anti-thrombogenic activity can be evaluated using an ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for an article containing a lumen by connecting the two ports of the article through a 2nd peristaltic pump. The size of tubing into which the article is placed and speed of the blood flow may be adjusted based on the size of the article being tested.

Aryl: unless otherwise indicated, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Attached: unless otherwise indicated, two moieties or compounds are "attached" if they are held together by any interaction including, by way of example, one or more covalent bonds, one or more non-covalent interactions (e.g., hydrogen bonds, ionic bonds, static forces, van der Waals interactions, combinations thereof, or the like), or a combination thereof.

Bioactive Agent/Active Agent/Biomolecule: unless otherwise indicated, "bioactive agent" or "active agent" or "biomolecule," used herein synonymously, refers to any organic or inorganic therapeutic, prophylactic or diagnostic agent that actively or passively influences a biological system. For example, a bioactive agent can be an amino acid, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be aptamers, proteins, glycoproteins, peptides, oligliopeptides, polypeptides, polymers, inorganic compounds, organometallic compounds, organic compounds or any synthetic or natural, chemical or biological compound.

Biocompatibility: unless otherwise indicated, "biocompatibility" is the ability of a material to perform with an appropriate host response in a specific situation. This can be evaluated using International Standard ISO 10993. Biocompatible compositions described herein are preferably substantially non-toxic.

Biological fluids: unless otherwise indicated, "biological fluids" are fluids produced by organisms containing proteins and/or cells, as well as fluids and excretions from microbes. This includes, but is not limited to, blood, saliva, urine, cerebrospinal fluid, tears, semen, lymph, ascites, sputum, bone marrow, synovial fluid, aqueous humor, cerumen, broncheoalveolar lavage fluid, prostatic fluid, cowper's fluid or pre-ejaculatory fluid, sweat, fecal matter, cyst fluid, pleural and peritoneal fluid, chyme, chyle, bile, intestinal fluid, pus, sebum, vomit, mucosal secretion, stool water, pancreatic juice, lavage fluids from sinus cavities, bronchopulmonary aspirates, or any derivative thereof (e.g., serum, plasma).

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c \ldots]_m–[X_xY_yZ_z \ldots]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: X—X—Y—Z—X—Y—Y—Z—Y—Z—Z—Z . . . . A non-limiting, exemplary alternating random configuration may have the non-limiting form: X—Y—X—Z—Y—X—Y—Z—Y—X—Z . . . , and an exemplary regular alternating configuration may have the non-limiting form: X—Y—Z—X—Y—Z—X—Y—Z . . . . An exemplary regular block configuration may have the following non-limiting configuration: . . . X—X—X—Y—Y—Y—Z—Z—Z—X—X—X . . . , while an exemplary random block configuration may have the non-limiting configuration: . . . X—X—X—Z—Z—X—X—Y—Y—Y—Y—Z—Z—Z—X—X—Z—Z—Z— . . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Branched: unless otherwise indicated, "branched" refers to a polymer structure in which a polymer chain divides into two or more polymer chains.

Brushes/Polymer Brushes: unless otherwise indicated, "brushes" or "polymer brushes" are used herein synonymously and refer to polymer chains that are bound to a surface generally through a single point of attachment using graft-from techniques. The polymers can be end-grafted (attached via a terminal group) or attached via a side chain or a position in the polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomeric residues) or polymer (e.g., >10 monomeric residues).

Carboxyammonium: unless otherwise indicated, a "carboxyammonium" moiety is a zwitterionic moiety comprising carboxylate and ammonium functionality and includes, for example, carboxyammonium monomers, carboxyammonium oligomers, carboxyammonium polymers, carboxyammonium repeat units, and other carboxyammonium-containing materials. Carboxybetaine monomers, oligomers, polymers, repeat units and other carboxybetaine materials are exemplary carboxyammonium moieties.

Cationic Monomer, Cationic Monomeric Unit or Cationic Repeat Unit: unless otherwise indicated, a "cationic monomer," "cationic monomeric unit" or "cationic repeat unit" is a monomer or a monomeric or repeat unit (the terms "monomeric unit" and "repeat unit" being used interchangeably) bearing a cation or other cationic species, e.g., a moiety capable of having a positive charge upon addition of an electrophile (e.g., a proton (H+) or an alkyl cation, for example in a pH dependent manner) or removal of a protecting group or a nucleophile).

Cationic species or Cationic Moiety: unless otherwise indicated, a "Cationic species" or a "Cationic Moiety" is a group, residue or molecule that is present in a positively charged or non-charged state, but in the non charged state is capable of becoming positively charged, e.g., upon addition of an electrophile (e.g., a proton (H+), for example in a pH dependent manner) or removal of a protecting group or a nucleophile. In certain instances, the group, residue or molecule is permanently charged, e.g., comprises a quaternary nitrogen atom.

Coating: unless otherwise indicated, "coating" refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate.

Complex Media: unless otherwise indicated, "complex media" refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

Copolymer: unless otherwise indicated, "copolymer" refers to a polymer derived from two, three or more monomeric species and includes alternating copolymers, periodic copolymers, random copolymers, statistical copolymers and block copolymers.

Cysteine: unless otherwise indicated, "cysteine" refers to the amino acid cysteine or a synthetic analogue thereof, wherein the analogue contains a free sulfhydryl group.

Degradation Products: unless otherwise indicated, "degradation products" are atoms, radicals, cations, anions, or molecules other than water formed as the result of hydrolytic, oxidative, enzymatic, or other chemical processes.

Dry Thickness: unless otherwise indicated, "Dry Thickness," as used herein in connection with a polymer layer, shall mean the thickness of the polymer layer using a scanning electron microscope (SEM). To measure dry thickness, the sample is freeze fractured for imaging by being submerged in liquid nitrogen then cracked with an ultra microtome blade. For metal substrates, they may be scored with a notch before a primer or the non-fouling polymer is applied to make freeze fracturing easier. The freeze fracturing should break the article at a plane approximately orthogonal to the polymer modified surface in order to measure the thickness of the polymer layer normal to the substrate. The samples are sputter coated in gold for 90 seconds using a sputter coater and then imaged under high vacuum at 5 kV using an SE2 detector under a Field Emission Scanning Electron Microscope (SEM). Exemplary microtome blades include the Leica Ultracut UCT Ultramicrotome, exemplary sputter coaters include the Cressington 208HR, exemplary SEMs include the Supra55VP FESEM, Zeiss. Dry thickness may be approximated by analyzing intensity of chemical signals in the grafted polymer, for instance, through the use of ATR-FTIR.

Fibrinogen Adsorption Assay: unless otherwise indicated, a "Fibrinogen Adsorption Assay" is an assay used to assess the capacity of a surface for fibrinogen. In the assay, test samples are placed in a suitable sized container, which may be a 96-well manifold, microcentrifuge tube, or other container. The volumes in the following are appropriate for a deep 96-well plate, but may be scaled to properly cover a device being tested. The samples are sterilized with 70% ethanol solution for thirty minutes and the test groups run with an n per run of 3-4. The sample container is blocked with 20 mg/mL Bovine Serum Albumin (BSA) in 1×PBS for 1 hour at 4° C., followed by three rinses with 1×PBS before samples are added. The sample is exposed to a solution containing 70 µg/mL unlabeled human fibrinogen, 1.4 µg/mL I-125 radiolabeled human fibrinogen, 35-55 µg/mL BSA in water, optionally tri-sodium citrate, and optionally sodium chloride. The BSA is a common agent co-lyophilized with the radiolabeled fibrinogen. Optionally, the BSA and radiolabeled fibrinogen may have been dissolved from a lyophilized form that contains tri-sodium citrate and sodium chloride. The samples are incubated for one hour at 37° C. on an orbital shaker at 150 RPM. The test solution is then removed and four 1-minute rinses with a 10 mM NaI and one 1-minute rinse with 1×PBS is performed. The samples are loaded into a gamma counter. The counter measures the radioactivity in I-125 counts per minute for each sample and this data is used to calculate the absolute fibrinogen adsorption or a percent reduction of the non-fouling polymer layer samples versus a reference substrate, that is, the same or an otherwise functionally equivalent substrate lacking the non-fouling polymer layer. The percent reduction is equal to: (1−non-fouling sample CPM/Average CPM of the reference substrate) *100%.

Global Average Dry Thickness: unless otherwise indicated, "Global Average Dry Thickness," as used herein in connection with a polymer layer, shall mean the mean calculated by averaging the Local Average Dry Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Dry Thickness is found by calculating the standard deviation of the Local Average Dry Thickness across at least 5, and preferably at least 10, representative locations spaced approximately evenly across the portion of the article carrying the polymer layer.

Global Average Humidified Thickness: unless otherwise indicated, "Global Average Humidified Thickness," as used herein in connection with a polymer layer, shall mean the mean calculated by averaging the Local Average Humidified Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Humidified Thickness is found by calculating the standard deviation of the Local Average Humidified Thickness across at least 5, and preferably at least 10, representative locations spaced approximately evenly across the portion of the article carrying the polymer layer.

Global Average $R_{rms}$ Surface Roughness: unless otherwise indicated, "Global Average $R_{rms}$ Surface Roughness," as used herein in connection with a polymer layer, shall mean the mean calculated by averaging the $R_{rms}$ surface roughness of at least 5, and preferably at least 10, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average $R_{rms}$ Surface Roughness is found by calculating the standard deviation of the Local Average $R_{rms}$ Surface Roughness across at least 5, and preferably at least 10, representative locations spaced approximately evenly across the portion of the article carrying the polymer layer.

Global Average $R_a$ Surface Roughness: unless otherwise indicated, "Global Average $R_a$ Surface Roughness" as used herein in connection with a polymer layer shall mean the mean calculated by averaging the $R_a$ surface roughness of at least 5, and preferably at least 10, representative locations spaced approximately evenly across the portion of the article carrying the polymer layer. $R_a$ refers to arithmetical mean roughness of a surface, which measures the vertical deviations of a real surface from its ideal form.

Graft: unless otherwise indicated, the term "graft," as used herein in connection with a polymer, means the modification of the surface of a material with a polymer by a "graft-from", "graft-through", or a "graft-to" approach, or a combination thereof to form a grafted polymer.

Graft-from method: unless otherwise indicated, the term "graft-from," as used herein in connection with a method for the modification of a material with a polymer, shall mean the in situ polymerization and growth of a polymer at the surface of, or within a material.

Graft-from polymer: unless otherwise indicated, the term "graft-from polymer," as used herein, shall mean a polymer formed by a graft-from method.

Graft-through method: unless otherwise indicated, the term "graft-through," as used herein in connection with a method for the modification of a material with a polymer, shall mean the in situ polymerization of monomers in the neighborhood of the material that may polymerize through functional groups presented from the material surface. For example, the material may have vinyl groups presented from the surface through which polymerization occurs.

Graft-through polymer: unless otherwise indicated, the term "graft-through polymer," as used herein, shall mean a polymer formed by a graft-through method.

Graft-to method: unless otherwise indicated, the term "graft-to," as used herein in connection with a method for the modification of a material with a polymer shall mean the modification of the surface of a material with a presynthesized polymer Graft-to polymer: unless otherwise indicated, the term "graft-to polymer," as used herein, shall mean a grafted polymer formed by a graft-to method.

Heteroalkyl: unless otherwise indicated, the term "heteroalkyl" means an alkyl group wherein at least one of the backbone carbon atoms is replaced with a heteroatom.

Heteroaryl: unless otherwise indicated, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as a chlorine, iodine, bromine, oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Humidified Thickness: unless otherwise indicated, "humidified thickness," as used herein in connection with a polymer layer, shall mean the thickness of the polymer layer using an environmental scanning electron microscope (ESEM and approximately 26% relative humidity). To measure humidified thickness, the sample is freeze fractured for imaging by being submerged in liquid nitrogen then cracked with an ultra microtome blade. The freeze fracturing should break the article at a plane orthogonal to the polymer modified surface in order to measure the thickness of the polymer layer normal to the substrate. After fracturing, the samples are soaked in water for at least one hour and then submerged in liquid nitrogen and fixed to a cold stage at $-8°$ C. to $-12°$ C. The samples are then imaged using a VPSE detector at the highest resolvable humidity (approximately 26% or 81 Pa) under a Scanning Electron Microscope (SEM) with an Environmental Scanning Electron Microscope (E-SEM). Exemplary microtome blades include the Leica Ultracut UCT Ultramicrotome, exemplary SEMs include the Supra55VP FESEM, Zeiss, and exemplary E-SEMs include the Zeiss EVO 55.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophilic: unless otherwise indicated, "hydrophilic" refers to solvents, molecules, compounds, polymers, mixtures, materials, or functional groups which have an affinity for water. Such materials typically include one or more hydrophilic functional groups, such as hydroxyl, zwitterionic, carboxy, amino, amide, phosphate, sulfonyl, hydrogen bond forming, and/or ether groups.

Hydrophobic: unless otherwise indicated, "hydrophobic" refers to solvents, molecules, compounds, polymers, mixtures, materials, or functional groups that are repelled by water. Such materials typically contain non-polar functional groups.

Immobilization/Immobilized: unless otherwise indicated, "immobilization" or "immobilized" refers to a material or bioactive agent that is covalently or non-covalently attached directly or indirectly to a substrate. "Co-immobilization" refers to immobilization of two or more agents.

Initiator: unless otherwise indicated, "initiator" refers to a substance or a combination of substances that can produce a radical or other species under relatively mild conditions and promote polymerization reactions. For example, redox pairs as described elsewhere herein may be an initiator.

Local Average Dry Thickness: unless otherwise indicated, "Local Average Dry Thickness" is the mean Dry Thickness calculated by averaging Dry Thickness measurements of at least 3, and preferably at least 5, representative locations spaced approximately evenly across a cross section of the article that spans approximately 10-40 micrometers. The standard deviation of the Local Average Dry Thickness is determined by calculating the standard deviation of the Dry Thickness across at least 5, and more preferably at least 10, representative locations spaced approximately evenly across a cross section of article that spans approximately 10-40 micrometers.

Local Average Humidified Thickness: unless otherwise indicated, "Local Average Humidified Thickness" is the mean Humidified Thickness calculated by averaging Humidified Thickness measurements of at least 3, and preferably at least 5, representative locations spaced approximately evenly across a cross section of the article that spans approximately 10-40 micrometers. The standard deviation of the Local Average Humidified Thickness may be determined by calculating the standard deviation of the Humidified Thickness across of at least 5, and preferably at least 10, representative locations spaced approximately evenly across a cross section of article that spans approximately 10-40 micrometers.

Membrane-Targeting Antimicrobial Agent: unless otherwise indicated, "membrane-targeting antimicrobial agent" refers to any antimicrobial agent that retains its bactericidal or bacteriostatic activity when immobilized on a substrate and can therefore be used to create an immobilized antimicrobial surface. In one embodiment, the membrane-targeting antimicrobial agent is an antimicrobial peptide, and in another embodiment it is a quaternary ammonium compound or polymer.

Non-Degradable: unless otherwise indicated, "non-degradable" refers to material compositions that do not react significantly within a biological environment either hydrolytically, reductively, enzymatically or oxidatively to cleave into smaller or simpler components.

Non-Fouling Composition/Non-Fouling Material/Non-Fouling Polymer/Non-Fouling Polymer Layer: unless otherwise indicated, a "non-fouling composition" or "non-fouling material" or "non-fouling polymer" or "Non-fouling polymer layer" as used interchangeably herein, is a composition that provides or increases the protein resistance of a surface of an article to which the composition is attached. For example, when attached to a substrate such a composition may resist the adhesion of proteins, including blood proteins, plasma, cells, tissue and/or microbes to the substrate relative to the amount of adhesion to a reference substrate, that is, the same or an otherwise functionally equivalent substrate lacking the composition. Preferably, a substrate surface will be substantially non-fouling in the presence of human blood. Preferably the amount of adhesion will be decreased 20%, 30%, 40%, 50%, 60%, 70%, 80%, or more, for example, 85%, 90%, 95%, 99%, 99.5%, 99.9%, or more, relative to the reference substrate. One particularly preferred measure of the non-fouling character or protein resistance of a surface is the amount of fibrinogen adsorbed in a Fibrinogen Adsorption Assay as described herein. Preferably, the amount of adsorbed fibrinogen using the Fibrinogen Adsorption Assay described herein is <125 $ng/cm^2$, <90 $ng/cm^2$, <70 $ng/cm^2$, <50 $ng/cm^2$, <30 $ng/cm^2$, <20 $ng/cm^2$, <15 $ng/cm^2$, <12 $ng/cm^2$, <10 $ng/cm^2$, <8 $ng/cm^2$, <6 $ng/cm^2$, <4 $ng/cm^2$, <2 $ng/cm^2$, <1 $ng/cm^2$, <0.5 $ng/cm^2$, or <0.25 $ng/cm^2$.

Non-Naturally Occurring Amino Acid: unless otherwise indicated, "non-naturally occurring amino acid" refers to any amino acid that is not found in nature. Non-natural amino acids include any D-amino acids, amino acids with side chains that are not found in nature, and peptidomimetics. Examples of peptidomimetics include, but are not limited to, b-peptides, g-peptides, and d-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, exist as the D and L forms. Nearly all of the amino acids occurring in nature are the L-forms. D-forms of the amino acids are not found in the proteins of higher organisms, but are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction. Non-naturally occurring amino acids also include residues, which have side chains that resist non-specific protein adsorption, which may be designed to enhance the presentation of the antimicrobial peptide in biological fluids, and/or polymerizable side chains, which enable the synthesis of polymer brushes using the non-natural amino acid residues within the peptides as monomeric units.

Polymer: unless otherwise indicated, "polymer" includes natural and synthetic, homopolymers and copolymers comprising multiple repeat units and, unless otherwise indicated, may be linear, branched, or dendritic. Examples of copolymers include, but are not limited to, random copolymers and block copolymers, smart polymers, temperature responsive (e.g., NIPAM), and pH responsive (e.g., pyridyl based) polymers.

Polypeptide/Peptide/Oligopeptide: unless otherwise indicated, "polypeptide," "peptide," and "oligopeptide" encompass organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e., production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

Quaternary Nitrogen: unless otherwise indicated, "quaternary nitrogen," as used herein, refers to a nitrogen atom that is a member of a quaternary ammonium cation.

$R_a$ Surface Roughness: unless otherwise indicated, "$R_a$ Surface Roughness" refers to arithmetical mean roughness of a surface, which measures the vertical deviations of a real surface from its ideal form. The roughness refers to surface micro-roughness which may be different than measurements of large scale surface variations. Preferably, this may be measured using atomic force microscopy (AFM) (MFP-3D, Asylum) across a field of approximately 1-30 μm by 1-30 μm, preferably 20 μm by 20 μm. The sample is washed with purified water to remove surface salts and then air dried. Standard silicon cantilever (Olympus AC160TS, spring constant 42 N/m) is employed for the measurement with an AC/Tapping mode. The $R_a$ surface roughness is calculated by the software (IGOR Pro) attached with the AFM machine. Alternatively, the roughness can be measured using a stylus profilometer. For example, the sample surface roughness can be measured by a Tencor P-16+ profilometer with a 60 degree, 2 μm diamond tip stylus. Preferably, an 800 μm scan length is chosen with 20 μm/second scan rate, 50 Hz scan frequency, and 2 μg loading force. At least three different sites are measured for the same sample, and the surface roughness is averaged from at least three samples. Alternatively, the $R_a$ surface roughness can be measured preferably by non-contact methods, including using optical profilometers. For example, the sample surface roughness is measured by a optical profilometer (Zeta Z20 or Olympus Lext OLS4000). Preferably a 3-D image is taken by the optical profilometer under a 50× objective lens, and the sample's surface roughness is then measured along at least three different lines cross the image. At least three different spots are measured and the surface roughness is averaged from at least three samples. In a preferred example an Olympus LEXT OLS4000 3D Laser Measuring Microscope is employed for roughness measurement and 3D imaging. A LEXT microscope utilizes low wavelength optical technology with a 408 nm laser in combination with confocal scanning. Samples to be measured are mounted on a glass slide by double-sided tape. Digital 3-D images are taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. Preferably, to measure the roughness, at least three images are taken from each sample and the $R_a$ roughness is calculated by using a 9 μm cut-off length.

$R_{rms}$ Surface Roughness: unless otherwise indicated, "$R_{rms}$ Surface Roughness" refers to root mean squared roughness of a surface, which measures the vertical deviations of a real surface from its ideal form. The roughness refers to surface micro-roughness which may be different than measurements of large scale surface variations. Preferably, this may be measured using atomic force microscopy (MFP-3D, Asylum) across a field of approximately 1-30 μm by 1-30 μm, preferably 20 μm by 20 μm. The sample is washed with purified water to remove surface salts and then air dried. Standard silicon cantilever (Olympus AC160TS, spring constant 42 N/m) is employed for the measurement with an AC/Tapping mode. The $R_{rms}$ surface roughness is calculated by the software (IGOR Pro) attached with the AFM machine. Alternatively the roughness can be measured using a stylus profilometer. For example, the sample surface roughness can be measured by a Tencor P-16+ profilometer with a 60 degree, 2 μm diamond tip stylus. Preferably, an 800 μm scan length is chosen with 20 μm/second scan rate, 50 Hz scan frequency, and 2 μg loading force. At least three different sites are measured for the same sample, and the surface roughness is averaged from at least three samples. Alternatively, the $R_{rms}$ surface roughness can be measured preferably by non-contact methods, including using optical profilometers. For example, the sample surface roughness is measured by a optical profilometer (Zeta Z20 or Olympus Lext OLS4000). Preferably a 3-D image is taken by the optical profilometer under a 50× objective lens, and the sample's surface roughness is then measured along at least three different lines cross the image. At least three different spots are measured and the surface roughness is averaged from at least three samples. In a preferred example an Olympus LEXT OLS4000 3D Laser Measuring Microscope is employed for roughness measurements and 3D imaging. A LEXT microscope utilizes low wavelength optical technology with a 408 nm laser in combination with confocal scanning can be used for the measurement. Samples to be measured are mounted on a glass slide by double-sided tape. Digital 3-D images are taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. To measure the roughness, at least three images have been taken from each sample and the $R_{rms}$ roughness is calculated by using a 9 μm cut-off length.

Solvent Extractable Polymerization Initiator: unless otherwise indicated, "Solvent Extractable Polymerization Initiator" refers to any compound capable of starting radical polymerization that has been incorporated within the article, wherein either the initiator or its degradation products may be extracted from the article using a suitable solvent. In general, extractions can use nonpolar or polar solvents. For example, extraction solvents such as water, acetone or ethanol; and/or other extraction solvents in which the solubility of the initiator and/or its degradation products is at least 1 mg/L. The extraction should be carried out for a sufficient time such that the change in concentration of the extract is not increasing more than 5% per hour. Alternatively, extraction until the amount of extracted material in a subsequent extraction is less than 10% of that detected in the initial extraction, or until there is no analytically significant increase in the cumulative extracted material levels detected. Extraction conditions include: 37° C. for 72 h; 50° C. for 72 h; 70° C. for 24 h; 121° C. for 1 h. Extraction ratio includes 6 $cm^2$/mL surface area/volume and/or 0.2 g sample/mL. In some instances, complete dissolution of the substrate may be appropriate. Materials shall be cut into small pieces before extraction to enhance submersion in the extract media, for example, for polymeric substrates approximately 10 mm×50 mm or 5 mm×25 mm are appropriate. The instrumentation used includes high-performance liquid chromatography-photo-diode array detection-mass spectrometry (HPLC-PDA-MS) for organics analysis; gas chromatography-mass spectrometry (GC-MS) for organics analysis; inductively coupled plasma-optical emission spectroscopy or mass spectrometry (ICP-OES or ICP-MS) for metals analysis; and sometimes ion chromatography (IC) for inorganics and ion analysis. Sometimes more advanced MS detectors such as time-of-flight (TOF) are used to obtain accurate mass information. Hexane and alcohol extractions are analyzed by GC-MS. Water and alcohol extractions are analyzed by HPLC. The initiator or its degradation products may be quantified and/or detected in the substrate or grafted polymer by the previously described methods. These include FTIR-ATR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometrically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

Stable: unless otherwise indicated, "stable," as used herein in reference to a material, means that the material retains functionality over extended periods of time. In one embodiment, the referenced material retains at least 90% of a referenced activity (or property) for at least 30 days at 37° C. in at least one of phosphate buffered saline containing protein, media, or serum, or in vivo. In one embodiment, the reference material retains at least 80% of a referenced activity (or property) for at least 90 days at 37° C. in at least one of phosphate buffered saline containing protein, media, or serum, or in vivo. In one embodiment, the referenced material retains at least 90% of the referenced activity (or property) for at least 30 days at 37° C. and at least 80% of the referenced activity (or property) for at least 90 days at 37° C. The referenced activity or property may include surface contact angle, non-fouling, anti-thrombogenic, and/or antimicrobial activity.

Static Contact Angle: unless otherwise indicated, "Static Contact Angle" is the angle at which a water/vapor interface meets a substrate surface at or near equilibrium conditions. The contact angle is measured by first soaking the samples with pure ethanol for 5 minutes and washing with PBS three times. The samples are then soaked within PBS (150 mM, pH 7.4) for 24 hours and washed three times with purified water. Then the samples are dried under a flow of air for 5 min before testing. A drop of purified water (e.g., 1 μL) is deposited on the test surface, the shape of the droplet is photographed by a microscope with a CCD camera using a video contact angle system (e.g., VCA 2000, AST Inc.), and the contact angle is then determined (using, for example, a VCA Optima XE). The size of the water droplet used to determine the contact angle may vary depending upon the substrate type and composition. For a 5 French device, for instance, an 0.1 µL drop of purified water may be used.

Substantially Hemocompatible: unless otherwise indicated, "substantially hemocompatible" means that the composition is substantially non-hemolytic, in addition to being non-thrombogenic and non-immunogenic, as tested by appropriately selected assays for thrombosis, coagulation, and complement activation as described in ISO 10993-4.

Substantially Non-Cytotoxic: unless otherwise indicated, "substantially non-cytotoxic" refers to a composition that does not substantially change the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

Substantially Non-Hemolytic Surface: unless otherwise indicated, "substantially non-hemolytic surface" means that the composition does not lyse 50%, preferably 20%, more preferably 10%, even more preferably 5%, most preferably 1%, of human red blood cells when the following assay is applied: a stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 cm$^2$ antimicrobial sample is incubated with 0.75 mL of 0.25% red blood cell suspension for 1 hour at 37° C. The solid sample is removed and cells are spun down at 6000 g, the supernatant is removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

Substantially Non-Toxic: unless otherwise indicated, "substantially non-toxic" means a surface that is substantially hemocompatible and substantially non-cytotoxic.

Substituted/Optionally Substituted: unless otherwise indicated, the term "substituted" and "optionally substituted" means that the referenced group is or may be substituted with one or more additional suitable group(s), which may be individually and independently selected, for example, from acetals, acyl, acyloxy, alkenoxy, alkoxy, alkylthio, alkynoxy, amido, amino, aryl, aryloxy, arylthio, azido, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfamoyl, sulfate, sulfhydryl, sulfonamido, sulfonate, sulfonyl, sulfoxido, thiocarbonyl, thiocyanato, thiol, and/or the protected derivatives thereof. It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substrate: unless otherwise indicated, "substrate" refers to the material from which a non-fouling polymer is grafted.

Sulfoammonium: unless otherwise indicated, a "sulfoammonium" moiety is a zwitterionic moiety comprising sulfate and ammonium functionality and includes, for example, sulfoammonium monomers, sulfoammonium oligomers, sulfoammonium polymers, sulfoammonium repeat units, and other sulfoammonium-containing materials. Sulfobetaine monomers, oligomers, polymers, repeat units, and other sulfobetaine materials are exemplary sulfoammonium moieties.

Tether/Tethering Agent/Linker: unless otherwise indicated, "tether" or "tethering agent" or "linker," as used herein synonymously, refers to any molecule, or set of molecules, or polymer used to covalently or non-covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

Undercoating Layer: unless otherwise indicated, "undercoating layer" refers to any coating, or combination of coatings, incorporated into a substrate from which a non-fouling polymer is grafted.

Zwitterion/Zwitterionic Material: unless otherwise indicated, "zwitterion" or "zwitterionic material" refers to a macromolecule, material, or moiety possessing both cationic and anionic groups. In most cases, these charged groups are balanced, resulting in a material with zero net charge.

Zwitterionic Polymers: unless otherwise indicated, "zwitterionic polymers" may be homopolymers or copolymers and include both polyampholytes (e.g., polymers with the charged groups on different monomer units) and polybetaine (polymers with the anionic and cationic groups on the same monomer unit). Exemplary zwitterionic polymers include alternating copolymers, statistical copolymers, random copolymers and block copolymers of two, three or more monomers.

DETAILED DESCRIPTION OF THE INVENTION

Medical devices and other articles comprise any of a wide range of materials. Certain of these materials, by virtue of their intrinsic characteristics, exhibit a greater resistance to protein adsorption and cell/microorganism adhesion; for example, hydrophilic materials tend to exhibit less protein adsorption than hydrophobic materials.

Methods of manufacture can greatly affect the surface characteristics of an article and its resistance to protein adsorption and cell/microorganism adhesion. Manufacturing methods may affect, for example, the porosity of a material, its roughness (micro-roughness and macro-roughness), incorporation of foreign-body inclusions that project from the surface of the material, and similar surface characteristics. Each of these, and other factors, may increase the degree of fouling that occurs at the article surface, independent of any further surface modification. This fouling can be cause by deposition of proteins, minerals, mammalian cells, or bacteria. In the clinical setting, deposition of biological materials leading to thrombosis and bacterial biofilm are particularly undesirable.

In general, the substrate includes a surface (i.e., one or more exposed or outer surface regions) and a bulk material or bulk positioned beneath the surface. The substrate preferably also includes a near-surface zone between the surface and the bulk. In one embodiment, the substrate surface, and the near-surface zone or region, if present, comprises a continuous phase of a first material and particles of a second material dispersed in the continuous phase. Preferably, the first material of the continuous phase is a polymeric material and the first and second materials are different (e.g., the second material is non-polymeric).

In accordance with one aspect of the present invention, therefore, the surface characteristics of the surface of a medical device or other article substrate are improved as a result of the treatments described herein. In some embodiments, for instance, the treatments reduce the surface roughness of the article substrate. In these and other embodiments, various low molecular weight species are reduced (or substantially or completely removed). Such surface characteristics may include, for example, scratches, pinholes, voids, discontinuous material phases (e.g., phase boundaries), surface contamination or other mechanical or chemical defects in the surface of the article that could potentially otherwise serve as a site for a performance failure. Such surface characteristics may be particularly acute when the substrate surface is a polymeric material. These and other treatments may be carried out before or during the formation of a grafted polymer layer on the surface of the substrate. Without being bound to any particular theory, it is believed that the surface treatments described herein provide an improved polymeric (or other) substrate surface for non-fouling grafted polymeric materials and methods.

In one aspect, the surface treatments of the present invention reduces (or even completely removes) low molecular weight species on or in the surface of the medical device or other article substrate. Such species may include, for example, discontinuous material phases (e.g., phase boundaries), surface contamination or other mechanical or chemical defects in the surface of the article that could potentially otherwise serve as a site for a performance or modification failure. In one embodiment, the low molecular weight species is an additive or a low molecular weight polymer. Additives that may be reduced or substantially or completely removed in accordance with the treatment processes described herein include, for example, inorganic and organic species. Low molecular weight polymers may be present as a result of the processing techniques and condition in the formation of the substrate and/or the underlying bulk material. In various embodiments, for example, low molecular weight species may have a molecular weight of less than about 50,000 Daltons, less than about 25,000 Daltons, less than about 15,000 Daltons, less than about 10,000 Daltons, less than about 5,000 Daltons, or less than about 1,000 Daltons. In another aspect, the surface treatments of the present invention improve (i.e., reduce) surface roughness of the substrate. Among the various surface treatments contemplated in connection with the present invention, include heat treatments (that is, heating all or a portion of the article or substrate for a period of time, resulting in a smoother, more homogeneous, or otherwise improved surface), solvent or reactant treatments that dissolve or otherwise physically and/or chemically reduce or remove material from the surface of or in the substrate, and combinations of such treatment methods. Physical agitation or sonication may also be applied during such treatments.

In general, the substrate surface regions may comprise a combination of different species, the presence of which may adversely effect the grafting process. By way of example, many substrates may include low molecular weight species, such as additives, in the form of processing aids such as waxes and oils. For instance, process aids are often present in extruded materials and may be included in the material before extrusion or added during the extrusion process. These process aids, in particular waxes, can be mobile within the substrate depending on the conditions to which the substrate is exposed, which may be a function of temperature, time, and solvent. Preferably, the processing aids that may be present in or on the substrate or substrate surface at the start of the surface modification are minimized through a treatment process. Other additives that may be present in or on the substrate surface include dispersing agents, binders, cross-linking agents, stabilizing agents, coloring agents, UV absorbent agents, charge adjusting agents, softening agents, anti-oxidants, pigments, flame retardants, scorch retarders, foaming agents, tackifiers, blowing agents, lubricants, UV-stabilizers, impact modifiers, and the like.

Additionally, or alternatively, the conditions used in the surface modification with a non-fouling modification may migrate low molecular weight species, such as additives or processing aids, to the surface of the non-fouling surface material. Representative conditions include aqueous exposure (e.g., with a treatment solution) at 22-80° C. from 2-12 hours. Other treatment methods involve a heat treatment of the substrate surface.

In one embodiment, the low molecular weight species that may be present at the start of the surface modification are sufficiently reduced through a treatment process so that they are substantially undetectable at the surface of the substrate at the start of the polymer grafting of the non-fouling layer. In a further embodiment, the additives and/or low molecular weight polymers present at the start of the surface modification are sufficiently reduced through a treatment process so that they are substantially undetectable at the surface of the non-fouling layer after the non-fouling surface modification.

In one preferred embodiment, the surface treatment and the surface modification are performed in a single step. By way of example, one or more solvents used in a surface treatment to dissolve or clean up low molecular weight species (e.g., additives, low molecular weight polymers, artifacts, and other components) may also function to introduce a polymerization initiator into and/or onto the substrate surface by physio-adsorption, allowing the substrate to swell and ultimately imbibing initiator into the substrate. This surface treatment/imbibing process may optionally be accompanied by mechanical agitation (e.g., sonication), for example, to promote dissolution or removal of the substrate surface material and/or to enhance the imbibing process. Suitable solvents include but are not limited to isopropanol and ethanol or solvent mixtures including one or both. As a result of the imbibing process, the imbibed substrate may contain about 0.001% by weight initiator. In some embodiments, the imbibed substrate will contain greater amounts of initiator, e.g., at least about 0.01% by weight. For example, in some embodiments the imbibed substrate will contain at least about 0.1% by weight. By way of further example, in some embodiments the imbibed substrate will contain about 0.05% to about 2% by weight initiator. By way of further example, in some embodiments the imbibed substrate will contain about 0.1% to about 1% by weight initiator. By way of further example, in some embodiments the imbibed substrate will contain about 0.2% to about 0.5% by weight initiator. By way of further example, in some embodiments the imbibed substrate will contain about 1% to about 10% by weight initiator. Typically, however, the imbibed substrate will contain less than about 20% by weight initiator.

In accordance with one aspect of the invention, the substrate is treated to reduce or substantially remove the presence of the material dispersed in the continuous phase (i.e., the second material) of the substrate before (or during) the formation of the grafted polymer layer on the article. These and other treatments may also have the added benefit of reducing roughness or otherwise smoothing the substrate surface. For example, in some embodiments, the surface of an article having a polymeric surface is chemically, mechanically, thermally, and/or chemomechanically treated or polished to reduce the incidence and/or the severity of surface species before the grafted polymer layer is formed. For example, the surface may be treated with a solvent, acid, base, reactant, polishing agent, chelating agent, or other moiety, or combinations thereof, that smoothes the polymeric surface of the substrate and/or reduces the incidence or severity of material discontinuities and/or contamination before the grafted polymer layer is formed on the polymeric surface of the article. By way of further example, the substrate surface may be contacted with a solution containing an acid, a base, or a chelating agent to reduce or substantially or completely remove the second material from the substrate. In other embodiments, the substrate surface treatment comprises contacting the substrate surface with a fluid or plasma to reduce or substantially or completely remove the second material from the substrate surface. In other embodiments, the substrate surface treatment involves polishing the substrate surface. In other embodiments, the substrate surface treatment comprises chemically, mechanically, or chemomechanically polishing the substrate surface Regardless of the treatment method employed, the treated surface is a polymeric surface having a relatively low surface roughness. In one embodiment, the treated surface has a global average $R_{rms}$ surface roughness of no more than 200 nm. In another embodiment, the treated surface has a global average $R_{rms}$ surface roughness of no more than 150 nm. In another embodiment, the treated surface has a global average $R_{rms}$ surface roughness of no more than 100 nm. In a preferred embodiment, the treated surface has a global average $R_{rms}$ surface roughness of no more than 50 nm. Preferably, the treated surface has a global average $R_{rms}$ surface roughness of no more than 25 nm. Preferably, the treated surface has a global average $R_{rms}$ surface roughness of no more than 10 nm. In some embodiments, the treated surface will have a global average $R_{rms}$ surface roughness of about 1 to 5.

Regardless of the treatment method employed, the treated surface is a polymeric surface also having a relatively low surface density of defects having a size, i.e., a largest dimension, greater than 0.5 micrometers. In some embodiments, the surface of the substrate from which the non-fouling material is to be grafted has a surface defect density of defects having a size greater than about 0.5 micrometers that is less than 0.1 defects/$\mu m^2$. For example, the surface of the substrate from which the non-fouling material is to be grafted may have a surface defect density of defects having a size greater than about 0.5 micrometers that is less than 0.05 defects/$\mu m^2$. By way of further example, the surface of the substrate from which the non-fouling material is to be grafted may have a surface defect density of defects having a size greater than about 0.5 micrometers that is less than 0.01 defects/$\mu m^2$. By way of further example, the surface of the substrate from which the non-fouling material is to be grafted may have a surface defect density of defects having a size greater than about 0.5 micrometers that is less than 0.002 defects/$\mu m^2$. By way of further example, the surface of the substrate from which the non-fouling material is to be grafted may have a surface defect density of defects having a size greater than about 0.5 micrometers that is less than 0.001 defects/$\mu m^2$.

In one embodiment, the treated surface is a polymeric surface also having a high degree of chemical uniformity. The chemical composition of the surface may be mapped with a variety of surface analytics including FTIR-ATR microscopy, EDAX mapping, and XPS. If an article has known heterogeneous components, such as barium sulfate crystals in polyurethane, the signals for individual components can be characterized as standards to aid in identifying the elements in the mixed composition. If a heterogeneous surface is present with distinct chemical signals, a mapping tool can be applied and the approximate fractional composition of each phase on the surface can be determined. In some embodiments, it is preferable for the highest fractional phase to account for more than 70% of the surface area. In further embodiments, it is preferable for the highest fractional phase to account for more than 80% of the surface area. In further embodiments, it is preferable for the highest fractional phase to account for more than 90% of the surface area. In further embodiments, it is preferable for the highest fractional phase to account for more than 95% of the surface area. In further embodiments, it is preferable for the highest fractional phase to account for more than 99% of the surface area. In further embodiments, it is preferable for the highest fractional phase to account for more than 99.5% of the surface area. In further embodiments, it is preferable for the highest fractional phase to account for more than 99.9% of the surface area.

In some embodiments, it may be preferable to have certain components or materials on the surface by exposing the surface to a certain environment such as vapors, solvents, stress fields, and/or electric and magnetic fields. The surface structure of a material, including atoms and molecules, is often mobile in response to the outside environment. In response to a hydrophobic environment (e.g., air), more hydrophobic (lower energy) components, for example the carbon backbone of poly(2-hydroxyethyl methacrylate), may migrate to the surface of a material—a process that reduces interfacial energy. In response to an aqueous environment, the surface may reverse its structure and point polar (hydrophilic) groups, for example the hydroxyl groups of poly(2-hydroxyethyl methacrylate), outward to interact with the polar water molecules. It is thought that energy minimization drives this process. Segmented thermoplastic elastomers may exhibit structural heterogeneity on the molecular, domain, and on large scale, e.g., spherulitic texture. Domain structures in segmented polyurethanes may change their orientation when stresses, such as elongation and annealing, are applied. In some embodiments, it may be desirable to expose the substrate to conditions that alter the groups presented from the surface before the non-fouling polymer is grafted. The surface composition can be estimated by using a combination of: contact angles, ESCA (XPS), auger electron spectroscopy, SIMS, ATR-FTIR, STM SEM, EDACS, and sum frequency generation.

Even if only a single phase is detectable on the article surface, it may be preferable to have a high purity of a single polymer on the surface. For example, a pure polyurethane surface may be preferable to one that contains both polyurethane and an extrusion wax that are well mixed. The purity of the surface can be estimated by applying ATR-FTIR microscopy of the article surface relative to the desired single surface material. Use ATR-FTIR, peak integration can be applied to assess the relative quantities of two or more materials with distinct infrared peaks. For instance, ethylene bis stearamide has a characteristic peak at 1639 cm$^{-1}$ and Tecoflex polyurethane has a characteristic peak at 1693 cm$^{-1}$. In some embodiments, it is preferable for the highest fractional component to account for more than 70% of the surface area. In further embodiments, it is preferable for the highest fractional component to account for more than 80% of the surface area. In further embodiments, it is preferable for the highest fractional component to account for more than 90% of the surface area. In further embodiments, it is preferable for the highest fractional component to account for more than 95% of the surface area. In further embodiments, it is preferable for the highest fractional component to account for more than 99% of the surface area. In further embodiments, it is preferable for the highest fractional component to account for more than 99.5% of the surface area. In further embodiments, it is preferable for the highest fractional component to account for more than 99.9% of the surface area.

In one preferred embodiment, the treated surface is a polymeric surface having relatively low surface roughness and a relatively low surface density of defects having a size greater than 0.5 micrometers. For example, in one embodiment, the treated surface is a polymeric surface having a global average $R_{rms}$ surface roughness of no more than 200 nm and a surface defect density of defects having a size greater than about 0.5 micrometers that is less than 0.1 defects/$\mu m^2$; more preferably in this embodiment; the global average $R_{rms}$ surface roughness is no more than 150 nm; still more preferably in this embodiment; the global average $R_{rms}$ surface roughness is no more than 100 nm. For example, in one embodiment, the treated surface is a polymeric surface having a global average $R_{rms}$ surface roughness of no more than 50 nm and a surface defect density of defects having a size greater than about 0.5 micrometers that is less than 0.1 defects/$\mu m^2$. By way of further example, in one embodiment, the treated surface has a global average $R_{rms}$ surface roughness of no more than 25 nm and a surface defect density of defects having a size greater than about 0.5 micrometers that is less than 0.1 defects/$\mu m^2$. By way of further example, in one embodiment, the treated surface has a global average $R_{rms}$ surface roughness of no more than 10 nm and a surface defect density of defects having a size greater than about 0.5 micrometers that is less than 0.1 defects/$\mu m^2$. By way of further example, in one embodiment, the treated surface will have a global average $R_{rms}$ surface roughness of about 1 to 5 and a surface defect density of defects having a size greater than about 0.5 micrometers that is less than 0.1 defects/$\mu m^2$. In each of the foregoing examples and embodiments of this paragraph, the defect density may be even less, e.g., is less than 0.1 defects/$\mu m^2$, less than 0.05 defects/$\mu m^2$, less than 0.01 defects/$\mu m^2$, less than 0.002 defects/$\mu m^2$, or even less than 0.001 defects/$\mu m^2$ for defects having a size greater than about 0.5 micrometers.

In one preferred embodiment, the treated surface is a polymeric surface having a relatively low surface roughness and a relatively high purity of a single polymer on the surface. For example, in one embodiment, the treated surface is a polymeric surface having a global average $R_{rms}$ surface roughness of no more than 50 nm and the highest fractional component using ATR-FTIR peak integration accounts for more than 70% of the surface area. By way of further example, in one embodiment, the treated surface has a global average $R_{rms}$ surface roughness of no more than 25 nm and the highest fractional component using ATR-FTIR peak integration accounts for more than 70% of the surface area. By way of further example, in one embodiment, the treated surface has a global average $R_{rms}$ surface roughness of no more than 10 nm and the highest fractional component using ATR-FTIR peak integration accounts for more than 90% of the surface area. By way of further example, in one embodiment, the treated surface will have a global average $R_{rms}$ surface roughness of about 1 to 5 and the highest fractional component using ATR-FTIR peak integration accounts for more than 95% of the surface area. In each of the foregoing examples and embodiments of this paragraph, the highest fractional component using ATR-FTIR peak integration accounts defect density may be even greater, e.g., more than 99% of the surface area, more than 99.5% of the surface area, or even more than 99.9% of the surface area.

In one preferred embodiment, the treated surface is a polymeric surface having a relatively low surface density of defects having a size greater than 0.5 micrometers and a relatively high purity of a single polymer on the surface. For example, in some embodiments, the surface of the substrate from which the non-fouling material is to be grafted has a surface defect density of defects having a size greater than about 0.5 micrometers that is less than 0.1 defects/$\mu m^2$ and the highest fractional component using ATR-FTIR peak integration accounts for more than 70% of the surface area. By way of further example, in one embodiment, the surface of the substrate from which the non-fouling material is to be grafted may have a surface defect density of defects having a size greater than about 0.5 micrometers that is less than 0.05 defects/$\mu m^2$ and the highest fractional component using ATR-FTIR peak integration accounts for more than 80% of the surface area. By way of further example, in one embodiment, the surface of the substrate from which the non-fouling material is to be grafted may have a surface defect density of defects having a size greater than about 0.5 micrometers that is less than 0.01 defects/$\mu m^2$ the highest fractional component using ATR-FTIR peak integration accounts for more than 90% of the surface area. By way of further example, the surface of the substrate from which the non-fouling material is to be grafted may have a surface defect density of defects having a size greater than about 0.5 micrometers that is less than 0.002 defects/$\mu m^2$ and the highest fractional component using ATR-FTIR peak integration accounts for more than 95% of the surface area. By way of further example, the surface of the substrate from which the non-fouling material is to be grafted may have a surface defect density of defects having a size greater than about 0.5 micrometers that is less than 0.001 defects/$\mu m^2$ the highest fractional component using ATR-FTIR peak integration accounts for more than 99% of the surface area. In each of the foregoing examples and embodiments of this paragraph, the highest fractional component using ATR-FTIR peak integration accounts defect density may be even greater, e.g., more than 99.5% of the surface area, or even more than 99.9% of the surface area.

In one preferred embodiment, the treated surface is a polymeric surface having relatively low surface roughness, a relatively low surface density of defects having a size greater than 0.5 micrometers, and a relatively high purity of a single polymer on the surface. For example, in one embodiment, the treated surface is a polymeric surface having a global average $R_{rms}$ surface roughness of no more than 50 nm, a surface defect density of defects having a size greater than about 0.5 micrometers that is less than 0.1 defects/$\mu m^2$ and the highest fractional component using ATR-FTIR peak integration accounts for more than 70% of the surface area. By way of further example, in one embodiment, the treated surface has a global average $R_{rms}$ surface roughness of no more than 25 nm, a surface defect density of defects having a size greater than about 0.5 micrometers that is less than 0.1 defects/$\mu m^2$ and the highest fractional component using ATR-FTIR peak integration accounts for more than 80% of the surface area. By way of further example, in one embodiment, the treated surface has a global average $R_{rms}$ surface roughness of no more than 10 nm, a surface defect density of defects having a size greater than about 0.5 micrometers that is less than 0.1 defects/$\mu m^2$ and the highest fractional component using ATR-FTIR peak integration accounts for more than 90% of the surface area. By way of further example, in one embodiment, the treated surface will have a global average $R_{rms}$ surface roughness of about 1 to 5, a surface defect density of defects having a size greater than about 0.5 micrometers that is less than 0.1 defects/μm², and the highest fractional component using ATR-FTIR peak integration accounts for more than 95% of the surface area. In each of the foregoing examples and embodiments of this paragraph, the defect density may be even less, e.g., is less than 0.1 defects/μm², less than 0.05 defects/μm², less than 0.01 defects/μm², less than 0.002 defects/μm², or even less than 0.001 defects/μm² for defects having a size greater than about 0.5 micrometers. By way of further example, in one embodiment, the treated surface has a global average $R_{rms}$ surface roughness of no more than 25 nm and a surface defect density of defects having a size greater than about 0.5 micrometers that is less than 0.1 defects/μm². Similarly, in each of the foregoing examples and embodiments of this paragraph, the highest fractional component using ATR-FTIR peak integration accounts defect density may be even greater, e.g., more than 99% of the surface area, more than 99.5% of the surface area, or even more than 99.9% of the surface area.

As noted above, in accordance with one aspect, substrates treated in accordance with the processes described herein include a substrate surface, a bulk beneath the substrate surface, and a near-surface zone lying between the substrate surface and the bulk. The substrate surface, near-surface zone and bulk contain a composite comprising a continuous phase of a first material and particles of a second material dispersed in the continuous phase, the first material being polymeric and the first and second material being a different material (e.g., a non-polymeric material). In some embodiments, the particles dispersed in the continuous phase have an average particle size and a distribution such that the number density of the particles in the near-surface zone is less than the overall number density of the particles in the composite, the near-surface zone extending a distance, D, from the substrate surface and into the substrate, D having a value that does not exceed twice the average particle size. In one embodiment, for example, after the surface is treated, the particles have an average particle size and a distribution such that the number density of the particles in the near-surface zone is less than the overall number density of the particles in the composite, the near-surface zone extends a distance, D, from the substrate surface and into the substrate, and D has a value that does not exceed twice the average particle size. In some embodiments, for example, the number density of the particles in the near-surface zone is less than 50% of the overall number density of the particles in the composite. In one embodiment, the number density of the particles in the near-surface zone is less than 25% of the overall number density of the particles in the composite; more preferably in this embodiment, less than 10%; more preferably in this embodiment, less than 5%; more preferably in this embodiment, less than 1%; more preferably in this embodiment, less than 0.5%; more preferably in this embodiment, less than 0.25%; more preferably in this embodiment less than 0.1%; more preferably in this embodiment, less than 0.05%; more preferably in this embodiment, less than 0.01%.

Advantageously, the surface treatment(s) described herein improve the surface characteristics and provide an improved polymeric surface for a non-fouling grafted polymer layer. Grafted polymer layers that are relatively uniform, that are sufficiently dense and/or branched, and/or are significantly hydrophilic can significantly increase a material's resistance to protein adsorption and/or cell/microorganism contamination.

Substrates

The article substrates that are treated in accordance with the processes described herein generally include a surface (i.e., one or more exposed or outer surface regions) and a bulk material or bulk positioned beneath the surface. The substrate preferably also includes a near-surface zone between the surface and the bulk. In one embodiment, the substrate surface, and the near-surface zone or region, if present, comprises a continuous phase of a first material and particles of a second material dispersed in the continuous phase. Preferably, the first material of the continuous phase is a polymeric material and the first and second materials are different (e.g., the second material is non-polymeric).

In general, the substrate comprises any of a wide range of materials selected from, for example, one or more metals, ceramics, glasses, polymers, biological tissues (living or dead), woven and non-woven fibers, semi-metals, and combinations thereof. In one preferred embodiment, the substrate comprises a polymer. In these and other embodiments, the substrate may be a composite of two or more materials, such as two or more polymeric materials. For example, the substrate may comprise a polymeric coating over a metallic, ceramic, glass, polymeric, woven or non-woven fiber or semi-metal core. Alternatively, the substrate may comprise a polymeric material throughout, i.e., from its surface and into its bulk. By way of further example, the substrate may comprise a polymeric coating, overlying a metallic, ceramic, glass, polymeric, woven or non-woven fiber or semi-metal core inner layer which, in turn, overlies a foam, metallic, ceramic, glass, polymeric, woven or non-woven fiber or semi-metal core. By way of another example, the substrate may comprise a first polymeric material overlaying a second polymeric material. Preferably, the substrate is at least polymeric throughout or comprises a polymeric material above a bulk of another (e.g., non-polymeric) material. In a particularly preferred embodiment, the substrate is a polymeric material through the entire substrate thickness.

Suitable polymeric materials include, but are not limited to, polyamide, polyamine, polyanhydride, polyazine, poly (carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof. Exemplary polymers include polystyrene and substituted polystyrenes, polyalkylenes, such as polyethylene and polypropylene, poly(urethane)s, polyacrylates and polymethacrylates, polyacrylamides and polymethacrylamides, polyesters, polysiloxanes, polyethers (including polyacetals), poly(orthoesters), poly(carbonates), poly(hydroxyalkanoate)s, polyfluorocarbons, PEEK, Teflon, silicones, epoxy resins, KEVLAR®, NOMEX®, DACRON®, HYTREL®, PEBAX®, SURLYN®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof. In one embodiment the substrate is a medical grade polyurethane or CARBOTHANE®, aliphatic polycarbonate-based polyurethanes, available from Lubrizol Corporation, blended with appropriate extrusion agents and plasticizers, possibly one already approved by the FDA or other appropriate regulatory agency for use in vivo. In one preferred embodiment, the first material comprises a polyurethane polymer or copolymer thereof. Preferred substrates are elastollan, pearlthane, desmopan, estane, pellethane, irogan, exelast EC, laripur, carbothane, carbothane, isoplast, tecoflex, tecophilic, tecoplast, tecothane, biomer (Ethicon), biospan, cardiothane 51 (avothane), cardiomat, chronoflex AL, chronoflex AR, chronoflex C, corplex, corethane, mitrathane, rimplast, toyobo TMS, vialon, enka PUR, comfeel ulcus, viasorb, bioclusive, blisterfilm, opsite, tegaderm, epigard, lyofoam, omiderm, microthane, and surethane.

In the embodiments in which a metallic bulk material is coated or covered with a polymeric coat or overlay, for example, suitable metallic materials include, but are not limited to, metals and alloys based on titanium, such as unalloyed titanium (ASTM F67) and titanium alloys, such as ASTM F1108, Ti-6Al-4V ELI (ASTM F136), Nitinol (ASTM F2063), nickel titanium alloys, and thermo-memory alloy materials; stainless steel (ASTM F138 and F139), tantalum (ASTM F560), palladium, zirconium, niobium, molybdenum, nickel-chrome, or certain cobalt alloys including Stellite, cobalt-chromium (Vitallium, ASTM F75 and Wrought cobalt-chromium (ASTM F90)), and cobalt-chromium-nickel alloys such as ELGILOY®, PHYNOX®, and HASTELLOY®.

In the embodiments in which a ceramic bulk material is coated or covered with a polymeric coat or overlay, for example, suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

As noted above, the second material dispersed within the continuous phase is different from the first material. The second material may include, for example, one or more radiopacifiers, colorants, and/or materials for enhancing the mechanical or structural properties of the substrate, or combinations thereof. In one embodiment, the second material is an inorganic material. In another embodiment, the second material comprises a metal, a ceramic, a glass, or a second polymeric material, and the second polymeric material has a chemical composition that differs from the first material.

In a particular embodiment, the second material dispersed within the continuous phase is a radiopaque material, for example, to aid in radiographic imaging. Illustrative examples of radiopaque materials include, but are not limited to, gold, barium salts (e.g., barium sulfate), bismuth salts (e.g., bismuth subcarbonate), gold or gold foil, tantalum, ferritic particles, platinum, platinum-tungsten, platinum-iridium, palladium, rhodium, and ionic or non-ionic contrasting agents such as diatrizoates, iodipamide, iohexyl, iopamidol, iothalamate, ioversol, ioxaglate, and metrizamide, and combinations thereof. In certain preferred embodiments, the radiopaque material is barium sulfate.

In another particular embodiment, the second material dispersed within the continuous phase comprises a colorant material, that is, a material that provides an optical or visual effect, tint, or color to a material. Suitable colorant materials include, but are not limited to, dyes and pigments. Where the colorant is a dye, for example, the colorant may be generally soluble in a solvent or carrier material dispersed within the continuous phase. Where the colorant is a pigment, on the other hand, the pigment material is typically an organic or inorganic, colored, white, or black material that is usually substantially insoluble in a solvent or carrier system, and is likewise insoluble in the continuous phase.

Suitable dye colorant materials include direct dyes, vat dyes, sulfur dyes, organic pigments, reactive dyes, disperse dyes, acid dyes, azoic dyes, synthetic dyes, basic dyes, fluorescent dyes, and phosphorescent dyes. Suitable pigment colorant materials include, by way of non-limiting example, pearlescent, metallic flake, cholesteric liquid crystal (CLC) pigments, ultramarine pigments, effect pigments, fluorescent pigments, phosphorescent pigments, inorganic pigments, carbon black pigments, natural pigments, organic pigments, mixed metal oxide pigments, iron oxide pigments, titanium dioxide pigments, zinc oxide pigments, titanium oxide pigments, organic azo pigments (such as azo lake pigments, insoluble azo pigments, condensed azo pigments, and chelate azo pigments), organic polycyclic pigments (such as phthalocyanine based pigments, anthraquinone based pigments, perylene based pigments, perinone based pigments, indigo based pigments, quinacridone based pigments, dioxazine based pigments, isoindolinone based pigments, quinophthalone based pigments, and diketopyrrolopyrrole (DPP) based pigments), dyeing lake pigments (such as lake pigments of acid or basic dyes), azine pigments; and the like.

In certain aspects, the first material (e.g., the polymeric substrate) or the second material may include polymeric colorant materials, which in some embodiments may additionally serve as a structural material of the substrate. One suitable and non-limiting example is the class of poly(aryleneethynylene) (PAE) polymers, which are conjugated and stable solid polymers that can fluoresce in orange, yellow, green, and blue ranges, for example. Suitable examples of PAE fluorescent polymers include poly(p-phenylene), poly(p-phenyleneethynylene) (PPE) or poly(p-phenylenevinylene) and derivatives thereof, including those derivates having alkyl, alkyl phenyl, and alkoxy groups such as grafted PPE and dioctyl-PPE, or ternary benzothiadiazole-co-alkyne-co-alkyne substituted backbones. Other suitable conjugated polymers include polythiophene and polyaniline, by way of example.

In another particular embodiment, the first material (e.g., the polymeric substrate) or the second material includes one or more structure- and/or density-enhancing agents including, for example, metals, ceramics, carbon fibers, nanoclays and other particles, glass (e.g., glass beads, and polymers (i.e., a second polymeric material having a chemical composition that differs from the first material), among others. Other additional additives that may be included within the continuous phase of the first material include, but are not limited to, dispersing agents, binders, cross-linking agents, stabilizing agents, coloring agents, UV absorbent agents, charge adjusting agents, softening agents, anti-oxidants, pigments, flame retardants, scorch retarders, foaming agents, tackifiers, blowing agents, lubricants, UV-stabilizers, impact modifiers, and the like.

The substrate may be in the form of, or form part of, gels, liquids, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), blood storage bags, surgical, medical or dental instruments, blood oxygenators, ventilators, pumps, drug delivery devices, tubing, wiring, electrodes, contraceptive devices, feminine hygiene products, endoscopes, grafts (including small diameter <6 mm), stents (including coronary, ureteral, renal, biliary, colorectal, esophageal, pulmonary, urethral, vascular, peripheral, neurovascular), stent grafts (including abdominal, thoracic, neurovascular and peripheral vascular), pacemakers, implantable cardioverter-defibrillators, cardiac resynchronization therapy devices, cardiovascular device leads, ventricular assist devices and drivelines, heart valves, vena cava filters, endovascular coils, catheters (including central venous, peripheral central, midline, peripheral, tunneled, dialysis access, urinary, neurological, peritoneal, intra-aortic balloon pump, angioplasty balloon, diagnostic, interventional, drug delivery, etc.), catheter connectors and valves (including needleless connectors), intravenous delivery lines and manifolds, shunts (including cardiac, cerebral, lumbar-peritoneal, pulmonary, portosystemic, portacaval, etc.), wound drains (internal or external including ventricular, ventriculoperitoneal, and lumboperitoneal), dialysis membranes, protein separation membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal, intracranial, glucose sensors), diagnostic devices (e.g., microfluidic, microelectromechanical, and optical), ophthalmic devices including contact lenses, intraocular lenses and phacoemulsification devices, orthopedic devices (including hip implants, knee implants, shoulder implants, spinal implants (including cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, breast implants, penile implants, maxillofacial implants, cosmetic implants, valves, appliances, scaffolding, suturing material, needles, hernia repair meshes, tension-free vaginal tape and vaginal slings, prosthetic neurological devices, tissue regeneration or cell culture devices, dialyzer, cranial implants, syringes, blood collection containers, scrotal implants, calve implants, buttock implants, extraocular implants, horn implants, subdermal implants, transdermal implants, magnetic implants, medical devices containing microfluidics, blood based sensors used outside of the body, nanoparticles used as sensors, IV catheter sheath, or other medical devices used within or in contact with the body or any portion of any of these.

The substrate may be in the form of, or form part of, gels, liquids, films, coatings, particles (nanoparticles, microparticles, or millimeter diameter beads), fibers (including woven and non-woven sponges and fabrics), marine and underwater coatings (including coatings for ships, submarines, marine and hydrokinetic devices, aquariums, underwater infrastructures, sewage pipes, and aqueduct tubes), packaging materials (including packaging for foods, beverages, cosmetics, and consumer products), desalination and water treatment systems (including condensers, spacers, pipelines, and membranes), separation membranes (including membranes for macrofiltration, microfiltration, ultrafiltration, nanofiltration, and reversed osmosis filtration), lab appliances and consumer products including containers (e.g., petri dishes, cell culture dishes, flasks, beakers), valves, needles, tapes, sealants, pipes, and tubes, earrings, body rings, contact lenses, cookware, gears (external/internal, spur, helical, double helical, bevel, hypoid, crown, worm, non-circular, etc.), turbomachinery (turbines and compressors), pumps (direct lift, displacement, velocity, buoyancy, and gravity), propellers, blades, knives, windshields, and glassware.

In one embodiment, the substrate is a vascularly inserted catheter such as a peripherally inserted central catheter (PICC), central venous catheter (CVC), or hemodialysis catheter, venous valves, punctual plugs, and intra-ocular devices and implants. In another embodiment, the substrate is a vascularly inserted catheter formed from a medical grade polyurethane or CARBOTHANE® or formed from a material coated with a medical grade polyurethane or CARBOTHANE®. In another embodiment, the substrate is a vascularly inserted catheter formed from a medical grade polyurethane or CARBOTHANE® containing a radiopaque additive, such as barium sulfate or bismuth salts to aid in radiographic imaging, or formed from a material coated with a medical grade polyurethane or CARBOTHANE® containing a radiopaque additive, such as barium sulfate or bismuth salts to aid in radiographic imaging.

In another embodiment, the substrate is a vascularly inserted catheter formed from a medical grade polyurethane or Tecothane® or formed from a material coated with a medical grade polyurethane or Tecothane®. In another embodiment, the substrate is a vascularly inserted catheter formed from a medical grade polyurethane or Tecothane® containing a radiopaque additive, such as barium sulfate or bismuth salts to aid in radiographic imaging, or formed from a material coated with a medical grade polyurethane or Tecothane® containing a radiopaque additive, such as barium sulfate or bismuth salts, to aid in radiographic imaging. In another embodiment, the substrate is a vascularly inserted catheter formed from a medical grade polyurethane or Pellethane® or formed from a material coated with a medical grade polyurethane or Pellethane®. In another embodiment, the substrate is a vascularly inserted catheter formed from a medical grade polyurethane or Pellethane® containing a radiopaque additive, such as barium sulfate or bismuth salts, to aid in radiographic imaging, or formed from a material coated with a medical grade polyurethane or Pellethane® containing a radiopaque additive, such as barium sulfate or bismuth salts, to aid in radiographic imaging.

Medical device substrates are often composed of multiple different materials, each with its own surface properties. Even devices composed primarily of a single polymer may be made up of material blends and can include plasticizers, radio-opacity agents, and other additives all of which will affect substrate surface properties.

Surface Treatments

As noted above, various flaws can be present in the surface structure of biocompatible materials. The quality of the surface of the substrate prior to surface modification can influence the quality of subsequent surface modifications described elsewhere herein, such as graft to and graft from modifications. Substrate surface flaws may be the result of low molecular weight species, such as additives and processing aids (e.g., waxes and/or oils), or physical characteristics, such as surface roughness (e.g., micro-roughness and macro-roughness), intentionally introduced to the substrate surface or material, or may be unintentionally present as artifacts of the manufacturing process or subsequent handling. For example, the surface may be contaminated with various particles, waxes, oils and other compositions that remain on the surface of the substrate. In one embodiment, for example, the low molecular weight species comprises a wax or a oil. In another embodiment, for example, the low molecular weight species comprises an additive. In another embodiment, for example, the low molecular weight species comprises a low molecular weight polymer. Surface improvements according to the methods described herein may involve various treatment or polishing techniques, and combinations thereof, which serve to remove, reduce, or diminish the concentration of various defects, resulting a relatively smooth substrate surface. Moreover, surface pre-treatments can assist in establishing a substantially uniform chemical composition throughout the surface; that is, the resulting treated substrate surface is relatively chemically homogeneous or at least with reduced heterogeneity relative to the surface prior to the treatment.

In general, substrate surface flaws may be of a chemical and/or physical nature; that is, the surface may include chemical defects (e.g., low molecular weight species), physical defects (e.g., roughness), or both chemical and physical defects. Reducing such flaws or defects can substantially improve performance of the resulting article.

Irrespective of the type of substrate (i.e., polymeric or non-polymeric), the substrate surface may include any number of physical defects in the form of scratches, ridges, pinholes, voids, waves, grooves, cracks, hills, pores, pillars, and the like, which contribute to an overall surface roughness. In addition to physical defects, the substrate surface may include chemical defects, such as the presence of undesirable or extraneous substances in or on the surface of the substrate. One example of a defect that may be considered both a chemical and a physical defect are particle(s) of barium sulfate (typically added to provide radio pacificity) that are only partially contained within the substrate. For example, substrates containing barium sulfate typically have some barium sulfate particles that are partially contained within the substrate and partially exposed; the exposed portions of such barium sulfate particles may extend from the surface of a substrate to a height of as much as 1 micrometer (as measured from the surface of the substrate). Some or all of the exposed or partially exposed barium sulfate particles protruding from a generally planar surface of the substrate may further include a polymer layer (e.g., a layer or oligomers or low(er) molecular weight polymers), which generally contributes to vertical deviations of the surface from its ideal form (that is, a rougher or less smooth surface). Another example of a defect that may be considered a chemical defect are process aids including waxes and oils.

Depending on the type of substrate and/or the particular species, flaw, or other component that is wished to be removed from, or reduced on or in the substrate, for example, the surface may be treated in a number of ways to affect the desired smoothing, homogenizing, and/or improved result. In one embodiment, for example, the surface treatment may involve a heat treatment; that is, the substrate, the underling bulk, and/or particular portions thereof, may be heated for a sufficient time and temperature to conceal, reduce, or substantially or completely remove the presence of chemical species, flaws, or other components. By way of example, heating all or a portion of the substrate surface or bulk may push processing materials, surface materials, artifacts, and other components towards a cooler region of the substrate or bulk, thus resulting in smoother and/or more homogeneous surface. By way of further example, heating all or a portion of the substrate may allow heterogeneous regions of stress in the substrate to relax producing a more uniform substrate. In another embodiment, the surface treatment may involve treating the surface with one or more reactants (e.g., acids, bases, solvents, chelating agents, etc.) that are capable of washing away or dissolving processing materials, artifacts, and other components, thus resulting in smoother and/or more homogeneous surface. Combinations of various surface treatments may also be employed, either serially or concurrently (e.g., a combination of a solvent treatment and a heat treatment).

In accordance with one embodiment, therefore, the substrate surface is subjected to a treatment stage (i.e., is pre-treated) prior to the formation of the grafted polymer layer on the substrate. This surface pre-treatment serves to reduce the incidence (i.e., surface density) or the severity (e.g., the size) of chemical and/or physical defects, thus providing a substrate surface that is at least substantially improved, if not substantially free of defects, prior to formation of the grafted polymer layer.

In accordance with another particular embodiment, the surface pre-treatment stage and the formation of the grafted polymer layer occur in a single step. As noted above, in some embodiments the solvent(s) or other reactants employed as part of the surface treatment (for example, to dissolve material from the surface) may have additional functionality in the surface modification process. For instance, in one embodiment, the surface treatment solvent also functions to introduce a polymerization initiator into and/or onto the substrate surface by physio-adsorption, allowing the substrate to swell and ultimately imbibing initiator into the substrate. Optionally, the surface treatment/imbibing process may be accompanied by mechanical agitation (e.g., sonication) in order to promote dissolution or removal of the substrate surface material and/or to enhance the imbibing process.

The type and method of treatment may generally depend on the type of substrate surface. For non-polymeric substrate surfaces, for example, the non-polymeric surface may be mechanically, chemically, thermally, or chemomechanically treated or polished to reduce surface roughness and/or the incidence and/or severity of cracks, pinholes and other structural defects in the substrate surface. This may involve exposing the surface to a solvent or a chemically reactive species to dissolve or chemically react with the material in the discontinuous material phase. In one embodiment, treating the substrate surface comprises contacting the substrate surface with a fluid or plasma to reduce (or even completely remove) the second material from the substrate surface. This may involve, for example, exposing the surface to, or contacting the surface with, a solution containing an acid, a base, a chelating agent, a solvent, or a chemically reactive species to effect the removal of the second material, and/or to dissolve or chemically react with the second material to reduce (or even completely remove) the second material from the substrate surface. In another embodiment, treating the substrate surface comprises polishing the substrate surface. For example, the substrate surface may be mechanically polished. By way of another example, the substrate may be solvent polished by exposing the substrate to a vapor of a solvent such as chloroform, dioxane or tetrahydrofuran. Where the substrate surface is a polymeric substrate surface, for instance, treatment may involve chemical or solvent treatment methods, the formation of a polymeric primer coating on the substrate surface, or a combination thereof. Additionally, or alternatively, the substrate surface treatment may involve heat treatment.

Methods of treatment of the substrate surface, therefore, may include both mechanical, chemical, and thermal treatment steps, including combinations of mechanical, chemical, and thermal treatments. For example, the substrate surface may be treated using water, solvents, surfactant solutions, or other cleaning solutions or gases, or polished, or subjected to a heat treatment, to reduce or substantially or completely remove particles, waxes or other foreign compositions that may be on the surface of the substrate. In some embodiments, a heat treatment may be employed. Representative mechanical surface treatments for use alone or in combination with another surface treatment include sonication, vibration, vortexing, shaking solutions, surface polishing, and microwave.

In one embodiment, the substrate is treated prior to or during formation of the grafted polymer layer with a composition or treatment such as an acid, base, chelator, solvent, surfactant, sonication, heat, freezing, reactant (or mixtures thereof) that dissolves, physically or chemically reacts with and reduces or completely or substantially removes any compositions that are included as chemical and/or physical defects. In one embodiment, the treatment comprises contacting the substrate with a treatment solution. In some embodiments, the treatment solution comprises one or more of water, an acid, a base, a chelator, a surfactant, or other reactant. In some embodiments, the acid, base, chelator or reactant (or mixture thereof) may dissolve or chemically react with additional or extraneous substrate material (i.e., polymer) that contributes to the surface roughness and/or heterogeneity of the substrate. In some embodiments, organic solvents, heat, freezing, sonication, vibration or combinations thereof are applied on the substrate materials to reduce (or even completely remove) the second phase. In general, these treatments can reduce or remove the second phase from the surface by increasing its solubility in the solution or debond it from the surface. In one embodiment, the substrate is treated prior to or during formation of the grafted polymer layer with a composition such as an acid, base, chelator or reactant (or mixtures thereof) that dissolves a portion or chemically reacts with a portion and reduces or substantially or completely removes any compositions that are included as chemical and/or physical defects. In some embodiments, the acid, base, chelator or reactant (or mixture thereof) may dissolve or chemically react with additional or extraneous substrate material (i.e., polymer) that contributes to the surface roughness and/or heterogeneity of the substrate. For example, exposed portions of barium sulfate particles may be removed or their presence reduced, e.g., partially or completely dissolved, using a mineral or organic acid and optionally, a chelator. In one such exemplary embodiment, polyurethane comprising particles of barium sulfate may be treated with an acid (e.g., 1N hydrochloric acid) or a base (e.g., 1N sodium hydroxide) to at least partially remove exposed barium sulfate particles. Alternatively, a chelator solution such as 1 N ethylenedioxy-diethylene-dinitrilo-tetraacetic acid (EDTA) may be applied on the polyurethane. Acid, base, and/or chelator treatment times may be in the range of 1 hour to 24 hours, or longer; more preferably about 2 hours. Without being bound by any particular theory, acid, base, and/or chelator treatment can reduce or at least partially remove the particles from the surface by increasing their solubility in the solution, and/or by decreasing the particle's adherence to the substrate. Representative acids include, for example, hydrochloric acid, sulfuric acid, nitric acid, phosphoric acid, boric acid, hydrofluoric acid, hydrobromic acid, lactic acid, acetic acid, carbonic acid, formic acid, citric acid, oxalic acid, uric acid, carboxylic acids, sulfonic acids, sulfamic acid, chlorous acid, and the like. Representative bases include, for example, sodium hydroxide, potassium hydroxide, ammonia solution, sodium chlorite, and the like. Representative chelators include, for example, water, carbohydrates, including polysaccharides, organic acids with more than one coordination group, lipids, steroids, amino acids and related compounds, peptides, phosphates, nucleotides, tetrapyrrols, ferrioxamines, ionophores, such as gramicidin, monensin, valinomycin, phenolics, 2,2'-bipyridyl, dimercaptopropanol, ethylenediaminotetraacetic acid, EDTA, ethylenedioxy-diethylene-dinitrilo-tetraacetic acid, EGTA, ethylene glycol-bis-(2-aminoethyl)-N,N,N',N'-tetraacetic acid, nitrilotriacetic acid, NTA, ortho-phenanthroline, salicylic acid, triethanolamine, TEA, 5-sulfosalicylic acid, oxalic acid, citric acid, tartaric acid, ethylene glycol-bis(2-aminoethylether)-N,N,N',N'-tetraacetic acid, enterobactin, ethylenediaminetetra(methylenephosphonic acid) and corresponding salts, and the like. Certain preferred chelators are polyamino carboxylic acids, e.g., glycine, beta-alanine, iminodiacetic acid (IDA), nitrilotriacetic acid (NTA), ethylenediaminetetraacetic acid, (EDTA), diethylene triamine pentaacetic acid (DTPA), 1,2-bis(o-aminophenoxy)ethane-N,N,N',N'-tetraacetic acid (BAPTA), 1,4,7,10-tetraazacyclododecane-1,4,7,10-tetraacetic acid (DOTA), and the like.

In another embodiment, the substrate is treated prior to or during formation of the grafted polymer layer with a composition such as a solvent that dissolves or chemically reacts with and reduces or substantially or completely removes any compositions that are included as chemical and/or physical defects. In one embodiment, the substrate is treated with a treatment solution comprising a solvent. In some embodiments, a solvent or mixture of solvents may dissolve or chemically react with additional or extraneous substrate material (i.e., polymer) that can contribute to the surface roughness and/or non-homogeneity of the substrate. Preferred solvents include acetone, ethanol, isopropanol, heptane, and methanol. Mixtures of these solvents (and those discussed elsewhere herein) with each other or with water may also be applied. Preferred temperatures for the treatment may be at or above room temperature, for example, 30° C., 40° C., 50° C., 60° C., or 80° C. Treatment times may be in the range of 1 hour to 24 hours, or longer; more preferably about 2 hours.

In another embodiment, the substrate is subjected to a heat treatment. In general, the temperature of the heat treatment is sufficient to achieve the desired result (i.e., providing an improved substrate surface) without negatively affecting (e.g., melting or disassociating) the substrate or the underlying bulk. It will be understood that the desired temperature of the heat treatment will generally depend on the particular polymeric material(s) employed in the substrate and/or bulk. Preferably, the thermal treatment is carried out at a temperature below the softening point of the substrate material. Typically, heat treatment is carried out at a temperature of from 20° C. to 100° C. for a period of about 30 seconds to about 2 hours. In one embodiment, for example, the surface treatment involves heating all or a portion of the substrate surface at a temperature of about 30° C., 40° C., 50° C., 60° C., 80° C., or 100° C. In another embodiment, the surface treatment involves heating all or a portion of the substrate surface at a temperature of from about 25° C. to about 60° C. In another embodiment, the surface treatment involves heating all or a portion of the substrate surface to a temperature of from about 30° C. to about 50° C. In another embodiment, the surface treatment involves heating all or a portion of the substrate surface to a temperature of from about 40° C. to about 80° C. Various devices and methods for supplying the thermal energy involved in the heat treatment may be used, including conventional ovens, microwave ovens, convection ovens, infrared heaters, induction-type heaters, water baths, and the like.

In one preferred embodiment, a treatment solution, such as a solvent or a solution comprising a solvent, is applied to reduce process aids. The treatment solution (e.g., solvent) may be applied such that it is stationary relative to the substrate. In these embodiments, the solvent is generally disposed atop or surrounding the substrate for a period of time. In other embodiments, at least one of the substrate and treatment solution moves relative to the another—as examples, the solution may be sprayed on to the substrate, or the substrate may be conveyed through a falling curtain of fluid or conveyed through a pool or bath of treatment solution material. Treatment solution can also be flowed, bubbled, sprayed, spin cast, dipped, painted on, brushed on, immersed, and the like. Vapors of solvents may also be employed. Treatment solution(s) may be applied under ambient (e.g., static) conditions, but may also be applied under heating, cooling, increased or reduced pressure, agitation (e.g., vibration, sonication), increased or decreased humidity, and the like. Additionally, or alternatively, the substrate and treatment solution can be subjected to a soxhlet extraction (using, for example, ethanol or isopropanol) for a period of time (e.g., 1-3 days).

Solvents that may be used in the treatment processes described herein include various kinds of organic solvents such as polar protic solvents, polar aprotic solvents and non-polar solvents. Mixtures of two or more of these or representative examples thereof may also be employed. More specific examples of solvents include aromatic hydrocarbons, chlorinated hydrocarbons, ethers, aliphatic hydrocarbons, alcohols, esters, ketones, amides, and mixtures thereof. Exemplary polar protic solvents include, but are not limited to, acetic acid, formic acid, n-butanol, ethanol, isopropanol, methanol, n-propanol, and water. In one embodiment, the solvent is a polar protic solvent selected from methanol, ethanol, isopropanol, and combinations thereof. Exemplary aprotic polar solvents include, but are not limited to, acetone, acetonitrile, cyclohexanone, cyclopentanone, dichloromethane, diglycol methyl ether, dimethylacetamide, dimethylformamide, dimethyl sulfoxide, hexamethylphosphoramide (HMPA), methylethylketone, N-methylpyrrolidone (NMP), sulfolane, and tetrahydrofuran (THF). In one embodiment, the solvent is an aprotic polar solvent selected from acetone, acetonitrile, cyclohexanone, cyclopentanone, dimethylacetamide, dimethylformamide, methylethylketone, and combinations thereof. Exemplary non-polar solvents include, but are not limited to, benzene, carbon disulfide, carbon tetrachloride, chloroform, cyclohexane, cyclopentane, diethyl ether, diisopropylether, 1,4-dioxane, hexane, heptane, mineral oil, pentane, and toluene. In one embodiment, the solvent is a non-polar solvent selected from cyclohexane, diethyl ether, hexane, heptane, toluene, and combinations thereof. In a particularly preferred embodiment, the solvent is selected from the group consisting of acetone, methanol, ethanol, isopropanol, heptane, and combinations thereof.

As noted above, mixtures of one or more organic solvents (i.e., a solvent system) may also be employed. For example, the solvent may be a mixture of polar protic solvent and a polar aprotic solvent (e.g., methanol:dimethylacetamide), a mixture of a polar protic solvent and a non-polar solvent (e.g., ethanol:heptane), and/or a mixture of a polar aprotic solvent and a non-polar solvent (e.g., acetonitrile:benzene). Mixtures of one or more organic solvents and water may also be applied.

Inorganic and/or aqueous solvents may also be employed in the treatment processes described herein. Exemplary aqueous solvents include water, saline, acids (e.g., 1N hydrochloric acid), bases (e.g., 1N sodium hydroxide), and surfactants (e.g., SDS, Tween®, and the like).

Surfactants and solutions of surfactants may be used in the treatment processes. Some preferred surfactants include anionic surfactants, such as alkyl sulfates: ammonium lauryl sulfate, sodium lauryl sulfate (SDS, sodium dodecyl sulfate, another name for the compound); alkyl ether sulfates: sodium laureth sulfate, also known as sodium lauryl ether sulfate (SLES), sodium myreth sulfate; sulfonates: for example docusates: dioctyl sodium sulfosuccinate; sulfonate fluorosurfactants: perfluorooctanesulfonate (PFOS), perfluorobutanesulfonate; alkyl benzene sulfonates; phosphates: for example alkyl aryl ether phosphate, alkyl ether phosphate; carboxylates: for example alkyl carboxylates: fatty acid salts (soaps): sodium stearate; sodium lauroyl sarcosinate; carboxylate fluorosurfactants: perfluorononanoate, perfluorooctanoate (PFOA or PFO).

Some preferred surfactants also include cationic surfactants, such as octenidine dihydrochloride; alkyltrimethylammonium salts: cetyl trimethylammonium bromide (CTAB) (as known as hexadecyl trimethyl ammonium bromide); cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; and dioctadecyldimethylammonium bromide (DODAB). Some preferred surfactants also include zwitterionic (amphoteric) surfactants: such as CHAPS (3-[(3-Cholamidopropyl)dimethylammonio]-1-propanesulfonate); cocamidopropyl hydroxysultaine; amino acids; Imino acids; cocamidopropyl betaine; and lecithin. Some preferred surfactants also include nonionic surfactants such as fatty alcohols: cetyl alcohol, stearyl alcohol, cetostearyl alcohol (consisting predominantly of cetyl and stearyl alcohols), oleyl alcohol; polyoxyethylene glycol alkyl ethers (Brij): $CH_3—(CH_2)10$-$16$-$(O—C_2H_4)1$-$25$-$OH$: octaethylene glycol monododecyl ether, pentaethylene glycol monododecyl ether; Polyoxypropylene glycol alkyl ethers: $CH_3—(CH_2)10$-$16$-$(O—C_3H_6)1$-$25$-$OH$; Glucoside alkyl ethers: $CH_3—(CH_2)10$-$16$-$(O$-Glucoside$)1$-$3$-$OH$; Decyl glucoside, Lauryl glucoside, Octyl glucoside; Polyoxyethylene glycol octylphenol ethers: $C_8H_{17}—(C_6H_4)—(O—C_2H_4)1$-$25$-$OH$; Triton X-100; Polyoxyethylene glycol alkylphenol ethers: $C_9H_{19}—(C_6H_4)—(O—C_2H_4)1$-$25$-$OH$: Nonoxynol-9; Glycerol alkyl esters: Glyceryl laurate; Polyoxyethylene glycol sorbitan alkyl esters: Polysorbates; Sorbitan alkyl esters: Spans; Cocamide MEA, cocamide DEA; Dodecyldimethylamine oxide; and Block copolymers of polyethylene glycol and polypropylene glycol: Poloxamers In one embodiment, treating the substrate surface comprises contacting the substrate surface with a plasma to reduce or substantially or completely remove the second material from the substrate surface. In another preferred embodiment, the substrate surface is treated with a corona, ozone, flame, high vacuum, to reduce or substantially or completely remove the second material from the substrate. Exemplary plasmas include, but are not limited to, helium, nitrogen, argon, oxygen, and water vapor. In one preferred embodiment, mixtures such as air and hydrogen/nitrogen are used.

In one embodiment, treating the substrate surface comprises contacting the substrate surface with a super critical fluid to reduce or substantially or completely remove the second material from the substrate surface. Exemplary super critical fluids include, but are not limited to, carbon dioxide, nitrous oxide, ethylene, propylene, propane, n-pentane, ethanol, ammonia, and water.

In one embodiment, treating the substrate surface comprises contacting the substrate surface with ion beams, etching or implantation, to reduce or substantially or completely remove the second material from the substrate surface. Exemplary ion beams include, but are not limited to, argon, xenon, and nitrogen.

In another embodiment, treating the substrate surface comprises contacting the substrate surface with a solution containing an acid, a base, or a chelating agent to reduce or substantially or completely remove the second material from the substrate surface. Exemplary acids for use in the treatment solution include, but are not limited to, hydrochloric acid, acetic acid, and citric acid. Exemplary bases for use in the treatment solution include, but are not limited to, sodium hydroxide, potassium hydroxide, and the like. Exemplary chelating agents for use in the treatment solution include, but are not limited to, ethylenediamine tetra-acetic acid ("EDTA"), diethylenetriaminepentaacetic acid ("DTPA"), and nitrilotriacetic acid ("NTA"). In one preferred embodiment, a combination of EDTA and potassium hydroxide. In another preferred embodiment, the treatment comprises contacting the substrate surface with a solution comprising a combination of EDTA and sodium hydroxide.

This interaction between the substrate surface and the treatment material and/or method advantageously reduces (or even completely removes) particles of a second material dispersed in or on the continuous phase of the substrate. In general, the substrate may be treated for a period of time to reduce at least some or substantially all of the undesirable chemical species at or near the substrate surface, including in the near-surface zone. In certain embodiments, for example, the substrate surface is treated for a period of time of at least about 1 hour. Typically, however, greater treatment times will be employed. For example, in some embodiments, the substrate surface is treated for a period of time of at least about 2 hours; at least about 4 hours; at least about 6 hours; at least about 8 hours; at least about 10 hours; at least about 12 hours; at least about 14 hours; at least about 16 hours; at least about 18 hours; at least about 20 hours; at least about 22 hours; or at least about 24 hours. By way of further example, in some embodiments; the substrate surface is treated for a period of time of about 2 hours to about 4 hours; about 2 hours to about 8 hours; about 2 hours to about 12 hours; about 2 hours to about 16 hours; about 2 hours to about 20 hours; or about 2 hours to about 24 hours. In one particular embodiment, the substrate surface is treated for a period of time of at least about 2 hours. In another particular embodiment, the substrate surface is treated for a period of time of about 2 hours to about 120 hours. In another particular embodiment, the substrate surface is treated for a period of time of about 2 hours to about 96 hours. In another particular embodiment, the substrate surface is treated for a period of time of about 2 hours to about 72 hours. In another particular embodiment, the substrate surface is treated for a period of time of about 2 hours to about 48 hours. In another particular embodiment, the substrate surface is treated for a period of time of about 2 hours to about 24 hours. In one preferred embodiment, the substrate surface is treated for a period of time of about 1 hour to about 3 hours. In such embodiments, the treatment temperature may be in the range of 22 to 60° C., more preferably in the range of 22 to 37° C., with about 25° C. being preferred in certain embodiments.

In certain preferred embodiments, the substrate and treatment composition or solution are subjected to mechanical agitation during the treatment. For example, the substrate and solvent may be flowed, bubbled, swirled, mixed, shaken, or sonicated in order to promote dissolution or removal of undesirable or less desirable chemical species (e.g., processing aids such as waxes) present on the surface of or in the substrate. Optionally, but preferably, the substrate and solvent are sonicated during the treatment. Additionally or alternatively, the treatment step may involve the use of energy such as shear or compression forces, or the like, to reduce the concentration of chemical species on the surface of or in the substrate. In one embodiment, the substrate can be suspended, immersed, or otherwise contacted with a solvent and then subjected to sonication. The substrate and solvent may be agitated for a time period effective to reduce the concentration of chemical species on the surface of or in the substrate to an acceptable level. The substrate may then be dried in alternative embodiments.

Thus, for example, the substrate surface may be subjected to a one or more mechanical, chemical, thermal, chemomechanical, chemothermal treatments, and combinations thereof. Among other things, these treatments can assist transmittance (imbibing) of molecules into a substrate, reduce the incidence and/or the severity of physical defects and chemical species, and/or selectively or non-selectively remove molecules from the substrate or modified surface. For instance, ultra-sonication between 40 and 50 Khz may be used to assist in permeation of initiators into substrates. Ultra-sonication in combination with specific solvents and varied thermal conditions, for instance, assists the imbibing process by maximizing penetration and distribution of molecular entities while minimizing exposure for each individual energy. Ultra-sonication can also be used to remove processing aids and may be applied in conjunction with solvent exposure and thermal conditioning. Ultra-sonication baths and wands may be used for either of these applications. Preferred powers include 100 to 600 watts. In one preferred embodiment, catheters are exposed to an alcohol while placed in a sonication bath. Temperature is controlled to less than 37° C. for varied specified periods, depending, for example, on the ultrasonic bath power, device loading, and transducer generating frequency, to facilitate the imbibing process or chemical species removal. If lumens within devices are being treated, a solvent may be drawn into the lumen before ultra-sonication is applied to prevent air exposure to ultrasonic power in the imbibing and/or species removal process. Solvents may also be periodically or continually drawn through the lumen during ultra-sonication processing, alone or in combination with thermal conditioning, for both imbibing and/or species removal.

It will be understood that the particular of surface treatment(s) selected, and the corresponding parameters thereof (e.g., the choice of solvent, acid, base, or other reactant for the treatment (if any); the choice of polishing technique; the temperature and duration of the treatment, and so on) will generally depend on the species being removed or reduced from the substrate surface and the composition of the substrate and/or bulk. Preferably, the solvent or reactant and corresponding treatment conditions will not substantially dissolve the substrate. Additionally, the solvent or reactant is preferably substantially inert (i.e., will not react with) when interacting with the substrate. It is also preferred to select a solvent or reactant that will not substantially swell the substrate; for example, swelling of less than 25%, more preferably less than 10%, more preferably less than 5%, and still more preferably less than 1%, is generally desired. The choice of solvent or reactant should also be capable of dissolving, solubilizing, or otherwise affecting the undesired, extraneous, or other components or materials at the surface of the substrate that contribute to the surface roughness or heterogeneity. Solvents or reactants that can be relatively easily removed from the substrate once the treatment is complete, e.g., by low boiling or extraction, are also preferred.

The particular acids, bases, solvent(s), chelating agents, or other reactants that are selected for use in the treatments described herein are preferably those in which the process aids or other low molecular weight species are soluble, but in which the substrate is not substantially soluble or insoluble. Preferably, process aids such as amide wax will have solubility in the solvents chosen for treatment above. In some embodiments, for example, the processing aids will have a solubility of at least 0.5 wt. % in the treatment solvent at the temperature applied. More preferably, the processing aids will have a solubility of at least 1 wt. %; at least 2.5 wt. %; or at least 5 wt. %. Further, the substrate components that are not intended to be removed, such as large molecular weight polyurethane in a catheter, have a solubility in the treatment solvent below 1 wt. % at the temperature applied. More preferably, the substrate components will have a solubility of less than 0.5 wt. %; less than 0.2 wt. %; or less than 0.1 wt. %. By applying mechanical treatment, process aids may be removed above their solubility limit in the treating solvent as they may come off the substrate in the form of particles or non-dissolved materials.

In one embodiment, the substrate surface is treated for a time period of at least about 2 hours with a solvent selected from the group consisting of acetone, methanol, ethanol, isopropanol, heptane, and combinations thereof. For example, the substrate surface may be treated with the solvent for a period of time of about 2 hours to about 120 hours. By way of another example, the substrate surface may be treated with the solvent for a period of time of about 2 hours to about 96 hours. By way of another example, the substrate surface may be treated with the solvent for a period of time of about 2 hours to about 72 hours. For example, the substrate surface may be treated with the solvent for a period of time of about 2 hours to about 48 hours. In one preferred embodiment, the substrate surface is treated with the solvent for a period of time of about 1 hour to about 3 hours. In another preferred embodiment, the substrate surface is treated for a time period of about 2 hours with a solvent selected from the group consisting of acetone, methanol, ethanol, isopropanol, heptane, and combinations thereof, wherein the substrate and solvent are subjected to sonication during at least a portion (e.g., about 5 minutes, about 15 minutes, about 30 minutes, about 1 hour, about 1 hour 15 minutes, about 1 hour 30 minutes, about 1 hour 45 minutes, or about 2 hours) of the surface treatment. In some of these embodiments, for example, a surface treatment is applied resulting in a substrate having a process aid concentration of less than about 0.1%; more preferably in this embodiment, the process aid concentration is less than about 0.05%; still more preferably in this embodiment, the process aid concentration is less than about 0.01%. In some of these embodiments, for example, a surface treatment is applied resulting in a substrate having a barium sulfate concentration of less than about 0.1%; more preferably in this embodiment, the process aid concentration is less than about 0.05%; still more preferably in this embodiment, the process aid concentration is less than about 0.01%. In some embodiments described above, the process aid is a wax or oil, and the substrate is a polyurethane.

In one embodiment, the substrate surface is treated for a time period of at least about 2 hours with a solution containing an acid, a base, or a chelating agent to reduce or substantially or completely remove the second material from the substrate surface. For example, the substrate surface may be treated with the acid, base, or chelating agent for a period of time of about 2 hours to about 120 hours. By way of another example, the substrate surface may be treated with the acid, base, or chelating agent for a period of time of about 2 hours to about 96 hours. By way of another example, the substrate surface may be treated with the acid, base, or chelating agent for a period of time of about 2 hours to about 72 hours. For example, the substrate surface may be treated with the acid, base, or chelating agent for a period of time of about 2 hours to about 48 hours. In one preferred embodiment, the substrate surface is treated with the acid, base, or chelating agent for a period of time of about 1 hour to about 3 hours. In another embodiment, the substrate surface is treated for a time period of about 2 hours with a solution containing an acid, a base, or a chelating agent, wherein the substrate and solution are subjected to sonication during at least a portion (e.g., about 5 minutes, about 15 minutes, about 30 minutes, about 1 hour, about 1 hour 15 minutes, about 1 hour 30 minutes, about 1 hour 45 minutes, or about 2 hours) of the surface treatment, to reduce or substantially or completely remove the second material from the substrate surface. In some of these embodiments, for example, a surface treatment is applied resulting in a substrate having a process aid concentration of less than about 0.1%; more preferably in this embodiment, the process aid concentration is less than about 0.05%; still more preferably in this embodiment, the process aid concentration is less than about 0.01%. In some of these embodiments, for example, a surface treatment is applied resulting in a substrate having a barium sulfate concentration of less than about 0.1%; more preferably in this embodiment, the process aid concentration is less than about 0.05%; still more preferably in this embodiment, the process aid concentration is less than about 0.01%. In some embodiments described above, the process aid is a wax or oil, and the substrate is a polyurethane.

In one embodiment, the substrate surface is treated for a time period of at least about 5 minutes with a fluid or plasma to reduce or substantially or completely remove the second material from the substrate surface. For example, the substrate surface may be treated with the fluid or plasma for a period of time of at least about 10 minutes, 15 minutes, 30 minutes, 45 minutes, 1 hour, or longer. Longer fluid or plasma treatment times include 2 hours, 4 hours, 6 hours, 12 hours, 24 hours, 48 hours, or longer. For example, the substrate surface may be treated with the fluid or plasma for a time period of about 1 hour to about 24 hours. In one preferred embodiment, the substrate surface is treated with the fluid or plasma for a period of time of less than about 1 hour. In another preferred embodiment, the substrate surface is treated with the fluid or plasma for a period of time of less than about 3 hours. In another embodiment, the substrate surface is treated for a time period of less than about 2 hours with a fluid or plasma, wherein the substrate and fluid or plasma are subjected to sonication during at least a portion (e.g., about 5 minutes, about 15 minutes, about 30 minutes, about 1 hour, about 1 hour 15 minutes, about 1 hour 30 minutes, about 1 hour 45 minutes, or about 2 hours) of the surface treatment, to reduce or substantially or completely remove the second material from the substrate surface. In some of these embodiments, for example, a surface treatment is applied resulting in a substrate having a process aid concentration of less than about 0.1%; more preferably in this embodiment, the process aid concentration is less than about 0.05%; still more preferably in this embodiment, the process aid concentration is less than about 0.01%. In some of these embodiments, for example, a surface treatment is applied resulting in a substrate having a barium sulfate concentration of less than about 0.1%; more preferably in this embodiment, the process aid concentration is less than about 0.05%; still more preferably in this embodiment, the process aid concentration is less than about 0.01%. In some embodiments described above, the process aid is a wax or oil, and the substrate is a polyurethane.

In one embodiment, the substrate surface is polished for a time period of at least about 5 minutes to reduce or substantially or completely remove the second material from the substrate surface. For example, the substrate surface may be polished for a period of time of at least about 10 minutes, 15 minutes, 30 minutes, 45 minutes, 1 hour, or longer. Longer polishing times include 2 hours, 4 hours, 6 hours, 12 hours, 24 hours, 48 hours, or longer. For example, the substrate surface may be polished for a time period of about 1 hour to about 24 hours. In one preferred embodiment, the substrate surface is polished for a period of time of less than about 1 hour. In another preferred embodiment, the substrate surface is polished for a period of time of less than about 3 hours. In some of these embodiments, for example, a surface treatment is applied resulting in a substrate having a process aid concentration of less than about 0.1%; more preferably in this embodiment, the process aid concentration is less than about 0.05%; still more preferably in this embodiment, the process aid concentration is less than about 0.01%. In some of these embodiments, for example, a surface treatment is applied resulting in a substrate having a barium sulfate concentration of less than about 0.1%; more preferably in this embodiment, the process aid concentration is less than about 0.05%; still more preferably in this embodiment, the process aid concentration is less than about 0.01%. In some embodiments described above, the process aid is a wax or oil, and the substrate is a polyurethane.

In one embodiment, the substrate surface is mechanically, chemically, or chemomechanically polished for a time period of at least about 5 minutes to reduce or substantially or completely remove the second material from the substrate surface. For example, the substrate surface may be mechanically, chemically, or chemomechanically polished for a period of time of at least about 10 minutes, 15 minutes, 30 minutes, 45 minutes, 1 hour, or longer. Longer mechanical, chemical, or chemomechanical polishing times include 2 hours, 4 hours, 6 hours, 12 hours, 24 hours, 48 hours, or longer. For example, the substrate surface may be mechanically, chemically, or chemomechanically polished for a time period of about 1 hour to about 24 hours. In one preferred embodiment, the substrate surface is mechanically, chemically, or chemomechanically polished for a period of time of less than about 1 hour. In another preferred embodiment, the substrate surface is mechanically, chemically, or chemomechanically polished for a period of time of less than about 3 hours. In some of these embodiments, for example, a surface treatment is applied resulting in a substrate having a process aid concentration of less than about 0.1%; more preferably in this embodiment, the process aid concentration is less than about 0.05%; still more preferably in this embodiment, the process aid concentration is less than about 0.01%. In some of these embodiments, for example, a surface treatment is applied resulting in a substrate having a barium sulfate concentration of less than about 0.1%; more preferably in this embodiment, the process aid concentration is less than about 0.05%; still more preferably in this embodiment, the process aid concentration is less than about 0.01%. In some embodiments described above, the process aid is a wax or oil, and the substrate is a polyurethane.

In addition to the surface treatments described herein, a range of other, different surface treatments may be employed in accordance with the processes disclosed herein. Electrolytic process can be used to increase the thickness of the natural oxide layer on the surface of metals. Electrochemical methods include, for example, anodization and cathodization. For example, aluminium, titanium, zinc, magnesium, niobium, and tantalum treatment with anodization yields oxide layers. Electroplating with other metal(s) may also be performed. In one embodiment, for example, mechanical and physical treatments include sonication, Ion beam etching (e.g., argon, xenon), Plasma etching (e.g., nitrogen, argon, oxygen, water vapor), Corona discharge, UV irradiation, Mechanical polishing, Solvent washing to smooth polymer surfaces, Flame treatment, physical vapor deposition (e.g., surface coating with diamond membrane). The surface may additionally or alternatively be oxidized; for instance oxidation including high voltage cornea treatment in the presence of oxygen may be employed. Oxidation methods may also include treatment of the substrate with oxidants such as, for example, hydrogen peroxide, chromic acid, nitrous acid, sulfuric acid/hydrogen peroxide solution, and combinations thereof. For example, in addition to removing organic contamination, titanium treatment with sulfuric acid/hydrogen peroxide is thought to result in an increased surface hydroxyl function.

Exemplary chemical polishing techniques include, chemical vapor deposition (CVD), acid and base treatments (including, for example, sodium hydroxide treatment of glass and polyester surfaces), and glass treatment with hydrogen fluoride. In one preferred embodiment, hydrochloric acid is particularly effective for the removal of barium sulfate particles on the surface of polymers. Chelators may also be employed to reduce or substantially or completely remove surface minerals. By way of example, mineral deposit and scale may be partially or substantially removed using ethylenediaminetetraacetic acid and bisphosphonates.

Surface modified to mask defects, including: over-coating, solvent coating, grafted or adsorbed surface modification, interpenetrating network modification, surface active bulk modification, polyelectrolyte multilayer films, metallization, sprayed hydroxyapatite (for e.g., orthopedic applications).

Other exemplary treatments include:

(1) coaxial compositions with homogeneous surfaces, for example, from the co-extrusion or co-injection of purified polymer over polymers with additives;

(2) surface crosslinking, for example using surface silanization for metals glass and Kevlar fibers;

(3) UV;

(4) electrochemical methods including anodization and cathodization. For example, aluminum protect aluminium, titanium, zinc, magnesium, niobium, and tantalum with anodization;

(5) oxidation including high voltage cornea treatment in the presence of oxygen. Oxidation also including treatment of the substrate with oxidants, for example, hydrogen peroxide, chromic acid, nitrous acid, sulfuric acid/hydrogen peroxide solution. For example, titanium treatment an oxidant.

(6) Aluminum treatment with sulfuric acid;

(7) Base treatments;

(8) Flame treatment; and (9) Sonication.

After treatment, the substrate surface preferably has a $R_{rms}$ surface roughness that is less than the $R_{rms}$ surface roughness of the untreated substrate. By way of further example, in one embodiment the treated substrate surface has a $R_{rms}$ surface roughness that is no more than 90% of the $R_{rms}$ surface roughness of the untreated substrate surface. By way of further example, in one embodiment the treated substrate surface has a $R_{rms}$ surface roughness that is no more than 75% of the $R_{rms}$ surface roughness of the untreated substrate surface. By way of further example, in one embodiment the treated substrate surface has a $R_{rms}$ surface roughness that is no more than 50% of the $R_{rms}$ surface roughness of the untreated substrate surface.

In certain embodiments, the substrate may contain a radiopaque agent, such as $BaSO_4$ or bismuth, to aid in radiographic imaging of the substrate. In one embodiment the polymer is Tecoflex-93A, Carbothane 85A, Pellethane 2363, Tecothane 97A, or PVC optionally containing 0 to 40% by weight $BaSO_4$. In one embodiment, the substrate comprises a polymer that does not contain extrusion or release waxes, which may be referred to as solvent grade. In a further embodiment, the substrate is a solvent grade polyurethane. In one embodiment, the substrate comprises a polyurethane that is substantially free of barium sulfate or other radiopaque crystals. In a further embodiment, the substrate is a solvent grade polyurethane that is substantially free of radiopaque crystals. In a further embodiment, the polymeric substrate is a solvent grade Carbothane. In a further embodiment, the polymeric substrate is a solvent grade Tecoflex. In a further embodiment, the polymeric substrate is a copolymer of silicone copolymer. In a further embodiment, the polymeric substrate is a copolymer of silicone and polyurethane. In a further embodiment, the polymeric substrate is Biomer.

The substrate can also include, but is not limited to, polymers such as polystyrene and substituted polystyrenes, polyethylene, polypropylene, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK, Teflon, silicones, epoxy resins, KEVLAR®, NOMEX®, DACRON®, HYTREL®, PEBAX®, SURLYN®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof.

Regardless of the pre-treatment steps, or even whether pre-treatment steps are employed, the surface of the substrate preferably has a $R_{rms}$ surface roughness that is no more than 200 nm. In one embodiment, for example, the surface of the substrate has a $R_{rms}$ surface roughness of no more than 150 nm; more preferably in this embodiment, the surface of the substrate has a $R_{rms}$ surface roughness of no more than 100 nm. In certain embodiments, the surface is even smoother. For example, the surface may have a $R_{rms}$ surface roughness of less than 50 nm. In some embodiments, the surface may have a $R_{rms}$ surface roughness of less than 20 nm.

Additionally, or alternatively, and regardless of the pre-treatment steps, or even whether pre-treatment steps are employed, the surface of the substrate to be subjected to further surface modifications has a surface defect density of defects having a size greater than about 0.5 micrometers that is less than 0.1 defects/$\mu m^2$ For example, the surface of the substrate to be subjected to further surface modifications may have a surface defect density of defects having a size greater than about 0.5 micrometers that is less than 0.05 defects/$\mu m^2$. By way of further example, the surface of the substrate to be subjected to further surface modifications may have a surface defect density of defects having a size greater than about 0.5 micrometers that is less than 0.01 defects/$\mu m^2$. By way of further example, the surface of the substrate to be subjected to further surface modifications may have a surface defect density of defects having a size greater than about 0.5 micrometers that is less than 0.002 defects/$\mu m^2$. By way of further example, the surface of the substrate to be subjected to further surface modifications may have a surface defect density of defects having a size greater than about 0.5 micrometers that is less than 0.001 defects/$\mu m^2$. In one particular embodiment, the treated surface has a $R_{rms}$ surface roughness of no more than 100 nm and a surface defect density of less than 0.1 defects/$\mu m^2$ of defects having a size greater than 0.5 micrometers.

Additionally, or alternatively, and regardless of the pre-treatment steps, in one embodiment, after the surface is treated, the particles dispersed in the continuous phase have an average particle size and a distribution such that the number density of the particles in the near-surface zone is less than the overall number density of the particles in the composite, the near-surface zone extends a distance, D, from the substrate surface and into the substrate, and D has a value that does not exceed twice the average particle size. In some embodiments, for example, the number density of the particles in the near-surface zone is less than 50% of the overall number density of the particles in the composite. In one embodiment, the number density of the particles in the near-surface zone is less 25% of the overall number density of the particles in the composite; more preferably in this embodiment, less than 10%; more preferably in this embodiment, less than 10%; more preferably in this embodiment, less than 5%; more preferably in this embodiment, less than 1%; more preferably in this embodiment, less than 0.5%; more preferably in this embodiment, less than 0.25%; more preferably in this embodiment less than 0.1%; more preferably in this embodiment, less than 0.05%; more preferably in this embodiment, less than 0.01%.

Surface Modifications

In accordance with the methods described herein, the treated substrate layers are subjected to surface modification; that is, a graft polymeric material layer is formed on a treated polymeric substrate surface layer having the characteristics described above.

In general, a non-fouling polymeric material is grafted from or to a polymeric substrate using, for example, conventional grafting techniques.

In one preferred embodiment, a graft-from approach is employed in which one or more polymerization initiators have been incorporated. In one embodiment, a non-fouling polymeric material is grafted from a substrate that is a composite of two or more materials, e.g., an underlying material such as a metal, ceramic, glass, semi-metal, polymer or other material with a polymeric or other material coating thereon (e.g., a primer coat as previously described herein). For example, in one embodiment, a non-fouling polymeric material is grafted from a polymeric primer coat, such as a polyurethane layer which overlies a metal or ceramic bulk. By way of further example, in one embodiment the non-fouling polymeric material is grafted from a polymeric primer layer, such as a polyurethane layer which overlies a polymeric bulk, such as polyurethane.

In one embodiment, the non-fouling polymeric material that is grafted from the substrate comprises a chain-growth polymer (that is, a polymer or polymer block formed by addition polymerization), or a combination thereof. The chain-growth polymer may be, for example, an addition polymer derived from monomer(s) incorporating double or triple bonds, e.g., an olefin. By way of further example, the chain-growth polymer may comprise an addition polymer derived from a cyclic monomer by means of a ring-opening polymerization reaction. Thus, the polymer may be a chain-growth homopolymer or copolymer. In a preferred embodiment, the polymer is a chain growth addition homopolymer or a chain growth addition copolymer comprising the residue of two or more monomers.

In accordance with one aspect of the present invention, it is generally preferred that the non-fouling polymeric material be prepared without inordinate use of a polyfunctional crosslinking agent. For example, it is generally preferred that the non-fouling polymeric material contain less than 50 mole % of the residue of a polyvalent crosslinker. In one such embodiment, the non-fouling polymeric material contains less than 25 mole % of the residue of a polyvalent crosslinker. In one such embodiment, non-fouling polymeric material contain less than 10 mole % of a polyvalent crosslinker. In one such embodiment, the non-fouling polymeric material contains less than 5 mole % of the residue of a polyvalent crosslinker. In one such embodiment, non-fouling polymeric material contain less than 3 mole % of a polyvalent crosslinker. In one such embodiment, the non-fouling polymeric material contains less than 0.1 mole % of the residue of a polyvalent crosslinker. In one such embodiment, the non-fouling polymeric material contains no residue of a polyvalent crosslinker.

Through grafting, step-growth or chain-growth techniques, the non-fouling polymeric material may comprise any of a range of polymer types or combinations thereof. The polymer backbone may be neutral (e.g., polyalkylene or polyether) or contain permanently charged moieties (e.g., cyclic or acyclic quaternized nitrogen atoms), or even zwitterionic backbones (e.g., phosphorylcholine backbones). In one embodiment, therefore, the non-fouling polymeric material comprises a polymer or copolymer selected from the group consisting of polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, hydrocarbon, etherester, ether-amide or ionized polyethylene and combinations thereof.

The polymer may also contain a wide range of pendant (side-chain) groups, hydrophilic and hydrophobic, neutral, anionic, cationic, or mixed charged. For example, the pendant groups may include neutral hydrophilic groups such as hydroxy, oligo(ethylene glycol) and/or poly(ethylene glycol) moieties, or it may include charged groups such as anionic moieties, cationic moieties, and zwitterionic moieties.

Zwitterionic Groups

Zwitterions are molecules that carry formal positive and negative charges on non-adjacent atoms within the same molecule and molecules that may be ionized by addition or removal of an electrophile or a nucleophile, or by removal of a protecting group. Both natural and synthetic polymers, containing zwitterion functionality, have been shown to resist protein adhesion. In one embodiment, the zwitterionic monomer contains a phosphorylcholine moiety, a carboxyammonium moiety, a sulfoammonium moiety, derivatives thereof, or combinations thereof. In one embodiment, the zwitterionic monomer contains a carboxyammonium moiety, a sulfoammonium moiety, derivatives thereof, or combinations thereof. In one embodiment, the zwitterionic monomer contains a sulfobetaine moiety or a carboxybetaine moiety. The zwitterionic polymer may be formed by initiating polymerization with radicals present in the polymeric substrate, in the presence of one or more monomers, such as sulfobetaine methacrylate or carboxybetaine methacrylate monomers.

Polysulfoammonium polymers such as polysulfobetaines, polycarboxyammonium polymers such as polycarboxybetaines and other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxybetaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

Materials containing, or composed of, these natural or synthetic zwitterions, can be grafted from surfaces, particularly the surfaces of medical devices, in order to improve biocompatibility, reduce thrombogenesis (such as on the surface of stents or venous valves), and reduce fouling by proteins or bacteria present in solution. This is particularly applicable for surfaces where non-specific binding of proteins in solution could negatively impact the desired or necessary mechanics of a device.

In one embodiment, the non-fouling polymer contains zwitterionic pendant groups covalently attached, directly or indirectly to the polymer back bone. The zwitterionic pendant groups may have an overall net charge, for instance, by having a divalent center of anionic charge and monovalent center of cationic charge or vice versa, or by having two centers of cationic charge and one center of anionic charge or vice versa. Preferably, however, the zwitterion has no overall net charge and most preferably has a center of monovalent cationic charge and a center of monovalent anionic charge. Additionally, the center(s) of cationic charge are preferably permanent; that is, it is preferably a quaternary nitrogen, quaternary phosphonium or tertiary sulfonium group. Additionally, the center(s) of anionic charge are also permanent; that is, they are completely ionized at physiological pH and are preferably carboxylate, phosphate, phosphonic, phosphonate, sulfate, sulfinic, or sulfonate.

In another embodiment, the polymer contains zwitterionic pendant groups covalently attached, directly or indirectly, to the polymer back bone, and the zwitterion corresponds to Formula ZI-3:

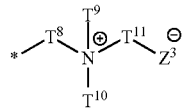

Formula ZI-3 wherein $T^8$ is a bond, hydrocarbylene, substituted hydrocarbylene, heterocyclo, or in combination with $T^9$ and $T^{10}$ and the nitrogen atom to which they are attached form a nitrogen-containing heteroaromatic ring, $T^9$ and $T^{10}$ are independently hydrogen, hydrocarbyl, substituted hydrocarbyl or heterocyclo, or, $T^9$ and $T^{10}$, in combination with $T^8$ and the nitrogen atom to which they are attached form a nitrogen-containing heteroaromatic ring, $T^{11}$ is hydrocarbylene, substituted hydrocarbylene, ether, or oxylated alkylene, $Z^3$ is carboxylate, phosphate, phosphonic, phosphonate, sulfate, sulfinic, or sulfonate, and

* designates the point of covalent attachment, direct or indirect, of the zwitterion of Formula ZI-3 to the polymer backbone.

In certain preferred embodiments in which the polymer contains zwitterionic pendant group corresponding to Formula ZI-3, $T^8$, $T^9$, $T^{10}$, and $T^{11}$ are selected from a more narrow range of substituents, $Z^3$ is carboxylate or sulfate, and the zwitterion corresponds to Formula ZI-4:

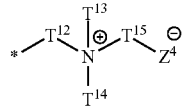

Formula ZI-4 wherein * designates the point of covalent attachment, direct or indirect, of the zwitterion of Formula ZI-4 to the polymer backbone; $T^{12}$ is a bond or —$(CH_2)_m$— with m being 1 to 3; $T^{13}$ and $T^{14}$ are independently hydrogen, alkyl, or substituted alkyl; $T^{15}$ is optionally substituted alkylene, phenylene, ether, or oxylated alkylene; and $Z^4$ is carboxylate or sulfate. For example, in this embodiment, $T^{13}$ and $T^{14}$ may independently be hydrogen or lower alkyl, e.g., methyl, ethyl, or propyl. By way of further example, in this embodiment, $T^{13}$ and $T^{14}$ may independently be hydrogen or lower alkyl, e.g., methyl, ethyl, or propyl. By way of further example, in this embodiment, $T^{15}$ may be —$(CH_2)_n$— with n being 1-8. By way of further example, in this embodiment, $T^{15}$ may be —$(CH_2)_2$— or —$(CH_2)_3$— and $T^{13}$ and $T^{14}$ may be methyl. By way of further example, in this embodiment, $T^{15}$ may be —$(CH_2)_2$— or —$(CH_2)_3$—, $T^{13}$ and $T^{14}$ may be hydrogen or alkyl. By way of further example, in this embodiment, $T^{12}$ may be —$(CH_2)_2$—, $T^{13}$ and $T^{14}$ may be methyl, $T^{15}$ may be —$(CH_2)_2$— and $Z^4$ may be carboxylate. By way of further example, in this embodiment, $T^{12}$ may be —$(CH_2)_2$—, $T^{13}$ and $T^{14}$ may be methyl, $T^{15}$ may be —$(CH_2)_3$— and $Z^4$ may be sulfate.

In certain preferred embodiments in which the polymer contains zwitterionic pendant group corresponding to Formula ZI-3, $T^8$, $T^9$ and $T^{10}$ and the nitrogen atom to which they are attached form a nitrogen-containing heteroaromatic ring. For example, $T^8$, $T^9$ and $T^{10}$ and the nitrogen atom to which they are attached may form an optionally substituted heterocycle, containing a quaternary nitrogen atom. One such embodiment corresponds to Formula ZI-5:

Formula ZI-5 wherein * designates the point of covalent attachment, direct or indirect, of the zwitterion of Formula ZI-5 to the polymer backbone; HET is a heterocycle containing a quaternary nitrogen atom, $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate. Exemplary zwitterions corresponding to Formula ZI-5 include zwitterions corresponding to Formulae ZI-6A and ZI-6B:

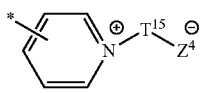

Formula ZI-6A

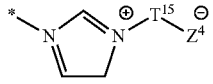

Formula ZI-6B wherein * designates the point of covalent attachment, direct or indirect, of the zwitterion of Formulae ZI-6A and ZI-6B to the polymer backbone; $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate.

In one embodiment, the polymer contains zwitterionic pendant groups covalently attached, directly or indirectly, to the polymer back bone, and the zwitterion corresponds to Formula ZI-7

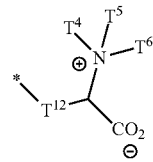

Formula ZI-7 wherein $T^4$, $T^5$ and $T^6$ are independently hydrogen, hydrocarbyl, substituted hydrocarbyl or heterocyclo; $T^{12}$ is a bond, hydrocarbylene, substituted hydrocarbylene, or heterocyclo, and * designates the point of covalent attachment, direct or indirect, of the zwitterion of Formula ZI-7 to the polymer backbone.

In one embodiment, the polymer contains zwitterionic pendant groups covalently attached, directly or indirectly, to the polymer back bone, and the zwitterion corresponds to Formula ZI-1:

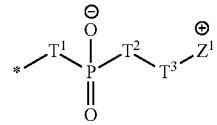

Formula ZI-1 wherein
$T^1$ and $T^2$ are independently oxygen, sulfur, NH or a bond,
$T^3$ is hydrocarbylene, substituted hydrocarbylene, ether, or oxylated alkylene,
$Z^1$ is a moiety comprising a quaternary nitrogen, phosphonium or sulfonium cationic group, and
* designates the point of covalent attachment, direct or indirect, of the zwitterion of Formula ZI-1 to the polymer backbone.

In certain preferred embodiments in which the polymer contains zwitterionic pendant group corresponding to Formula ZI-1, $T^1$ and $T^2$ are oxygen, $Z^1$ is quaternary nitrogen, and the zwitterion corresponds to Formula ZI-2:

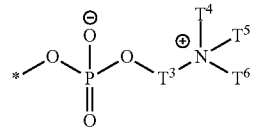

Formula ZI-2 wherein * designates the point of covalent attachment of the zwitterion of Formula ZI-2 to the polymer backbone, $T^3$ is hydrocarbylene, substituted hydrocarbylene, or oxylated alkylene, and $T^4$, $T^5$ and $T^6$ are independently hydrogen, hydrocarbyl, substituted hydrocarbyl or heterocyclo. For example, in this embodiment, $T^3$ may be —$(CH_2)_n$— with n being 1-8. By way of further example, in this embodiment, $T^4$, $T^5$ and $T^6$ may independently be lower alkyl, e.g., methyl, ethyl or propyl. By way of further example, in this embodiment, $T^3$ may be —$(CH_2)_n$— with n being 1-3, and $T^4$, $T^5$ and $T^6$ may independently be lower alkyl, e.g., methyl, ethyl or propyl. By way of further example, in this embodiment, $T^3$ may be —$(CH_2)_n$— with n being 1-3, and one or more of $T^4$, $T^5$ and $T^6$ may be substituted hydrocarbyl such as oligomeric phosphorylcholine (e.g., Formula 9).

Neutral Hydrophilic Pendant Groups

In one embodiment, the polymer contains neutral hydrophilic pendant groups covalently attached, directly or indirectly, to the polymer backbone. Exemplary neutral hydrophilic groups include hydroxy, thiol, oxylated alkyls (e.g., oligoethylene glycol, polyethylene glycol and/or polypropylene glycol), ether, thioether, and the like. In one such specific embodiment, the polymer contains pendant groups comprising alkoxylated moieties corresponding to Formula POA-1:

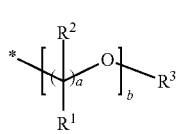

Formula POA-1 wherein a is 1-3, b is 1-8, each $R^1$ and $R^2$ is independently selected from the group consisting of hydrogen, halogen, and optionally substituted lower alkyl, $R^3$ is hydrocarbyl, substituted hydrocarbyl or heterocyclo, and * designates the point of attachment of the moieties corresponding to Formula POA-1 to the remainder of the pendant group and the backbone. By way of example, in one such embodiment, each $R^1$ and $R^2$ are hydrogen, n is 2 or 3. By way of further example, in one such embodiment, each $R^1$ and $R^2$ is hydrogen, n is 2 or 3, and b is 3-5. By way of further example, in one such embodiment, each $R^1$ and $R^2$ is hydrogen, n is 2 or 3, b is 3-5, and $R^3$ is alkyl. In one embodiment, the repeat units are derived from macromonomers containing 2-20 alkylene oxide units.

Repeat Units

In general, homopolymers or copolymers comprising zwitterionic pendant groups, neutral hydrophilic pendant groups, cationic pendant groups and/or anionic pendant groups may be prepared by polymerization of any of a wide range of monomers. In one preferred embodiment, the non-fouling polymeric material is a homopolymer or copolymer comprising repeat units derived from an olefinic monomer. Thus, for example, in one embodiment the non-fouling polymeric material comprises repeat units derived from an olefinic monomer and corresponding to Formula 1:

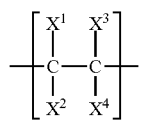

Formula 1 wherein $X^1$ and $X^2$ are independently hydrogen, hydrocarbyl, substituted hydrocarbyl, heterocyclo, or substituted carbonyl, provided, however, $X^1$ and $X^2$ are not each selected from the group consisting of aryl, heteroaryl, and heterosubstituted carbonyl, $X^3$ is hydrogen, alkyl or substituted alkyl, and $X^4$ is $-OX^{40}$, $-NX^{41}X^{42}$, $-N^+X^{41}X^{42}X^{43}$, $-SX^{40}$, aryl, heteroaryl or acyl, $X^{40}$ is hydrogen, hydrocarbyl, substituted hydrocarbyl, heterocyclo or acyl, and $X^{41}$, $X^{42}$ and $X^{43}$ are independently hydrogen, hydrocarbyl, substituted hydrocarbyl or heterocyclo.

In certain embodiments in which the non-fouling polymeric material comprises repeat units corresponding to Formula 1, it is preferred that $X^4$ of at least a fraction of the repeat units comprise alkoxylated moieties, zwitterionic moieties, anionic moieties, or cationic moieties. In such embodiments, for example, $X^1$ and $X^2$ may be hydrogen, and the polymer comprises repeat units corresponding to Formula 2:

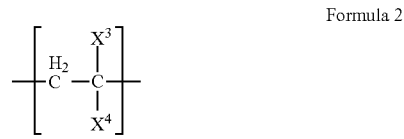

Formula 2 wherein $X^3$ is hydrogen, alkyl or substituted alkyl, and $X^4$ is a pendant group comprising an oxylated alkylene moiety, a zwitterionic moiety, an anionic moiety, or a cationic moiety. For example, $X^3$ may be hydrogen or lower alkyl. By way of further example, $X^4$ may be a pendant group comprising an oxylated alkylene moiety corresponding to Formula POA-1. By way of further example, the repeat unit of Formula 2 may be zwitterionic repeat unit comprising a zwitterionic moiety corresponding to Formula ZI-1, ZI-2, ZI-3, ZI-4, ZI-5, ZI-6A, ZI-6B, or ZI-7. By way of further example, the repeat unit of Formula 2 may be a cationic repeat unit. By way of further example, the repeat unit of Formula 2 may be an anionic repeat unit. By way of further example, $X^3$ may be hydrogen or methyl and $X^4$ may be a pendant group comprising an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7.

In one presently preferred embodiment, the non-fouling polymeric material comprises repeat units corresponding to Formula 2 wherein $X^4$ is acyl and the repeat units correspond to Formula 3:

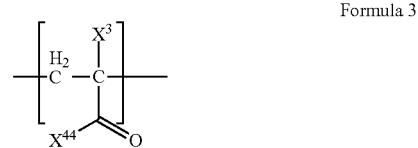

Formula 3 wherein $X^{44}$ comprises an oxylated alkylene moiety, a zwitterionic moiety, an anionic moiety, or a cationic moiety. For example, $X^{44}$ may be $-OX^{45}$, $-NX^{45}X^{46}$ or $-SX^{45}$, wherein $X^{45}$ is a substituted hydrocarbyl or heterocyclo moiety comprising an oxylated alkylene moiety, a zwitterionic moiety, an anionic moiety, or a cationic moiety, and $X^{46}$ is hydrogen, hydrocarbyl, substituted hydrocarbyl or heterocyclo. For example, $X^3$ may be hydrogen or lower alkyl. By way of further example, $X^{44}$ may be $-OX^{45}$, or $-NHX^{45}$. By way of further example, $X^{44}$ may be $-OX^{45}$, or $-NHX^{45}$ wherein $X^{45}$ comprises an oxylated alkylene moiety corresponding to Formula POA-1. By way of further example, $X^{44}$ may be $-OX^{45}$, or $-NHX^{45}$ wherein $X^{45}$ comprises a zwitterionic moiety corresponding to Formula ZI-1, ZI-2, ZI-3, ZI-4, ZI-5, ZI-6A, ZI-6B, or ZI-7. By way of further example, the repeat unit of Formula 3 may be a cationic repeat unit. By way of further example, the repeat unit of Formula 3 may be an anionic repeat unit. By way of further example, $X^3$ may be hydrogen or methyl and $X^{44}$ may comprise an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7. In one particularly preferred embodiment, the polymer contains repeat units corresponding to Formula 3 and $X^{44}$ is —O(CH$_2$)$_2$N$^+$(CH$_3$)$_2$(CH$_2$)$_n$ SO$_3^-$, —O(CH$_2$)$_2$N$^+$(CH$_3$)$_2$(CH$_2$)$_n$CO$_2^-$, —NH(CH$_2$)$_3$N$^+$ (CH$_3$)$_2$(CH$_2$)$_n$CO$_2^-$, or —NH(CH$_2$)$_3$N$^+$(CH$_3$)$_2$(CH$_2$)$_n$SO$_3^-$, wherein n is 1-8. In one embodiment, the polymer contains repeat units corresponding to Formula 3 and $X^{44}$ is —NH (CH$_2$)$_m$N(CH$_2$)$_n$CH$_3$(CH$_2$)$_p$SO$_3$, —NH(CH$_2$)$_m$N(CH$_2$)$_n$ CH$_3$(CH$_2$)$_p$CO$_2$, —NH(CH$_2$)$_m$N$^+$[(CH$_2$)$_n$CH$_3$]$_2$(CH$_2$)$_p$SO$_3$, —NH(CH$_2$)N$^+$[(CH$_2$)$_n$CH$_3$]$_2$(CH$_2$)$_p$CO$_2$, —NH(CH$_2$)$_m$N-cyclo-(CH$_2$)$_p$CO$_2$, or —NH(CH$_2$)$_m$Ncyclo-(CH$_2$)$_p$SO$_3$, (Ncyclo is a heterocyclic structure or a heterocyclic derivative containing at least one nitrogen element), wherein m is 1-8; n is 0-5; and p is 1-8. In one embodiment, the polymer contains repeat units corresponding to Formula 3 and $X^{44}$ is —O(CH$_2$)$_m$ N(CH$_2$)$_n$CH$_3$(CH$_2$)$_p$SO$_3$, —O(CH$_2$)$_m$N(CH$_2$)$_n$ CH$_3$(CH$_2$)$_p$CO$_2$, —O(CH$_2$)$_m$N$^+$[(CH$_2$)$_n$CH$_3$]$_2$(CH$_2$)$_p$SO$_3$, —O(CH$_2$)N$^+$[(CH$_2$)$_n$CH$_3$]$_2$(CH$_2$)$_p$CO$_2$, —O(CH$_2$)$_m$Ncyclo-(CH$_2$)$_p$CO$_2$, or —O(CH$_2$)$_m$Ncyclo-(CH$_2$)$_p$SO$_3$ wherein m is 1-8; n is 0-5; and p is 1-8. In one embodiment, the polymer contains repeat units corresponding to Formula 3 and $X^{44}$ is —O(CH$_2$)$_2$N$^+$(CH$_3$)$_2$(CH$_2$)$_3$SO$_3$, —O(CH$_2$)$_2$N$^+$(CH$_3$)$_2$ (CH$_2$)$_2$CO$_2$, —NH(CH$_2$)$_2$N$^+$(CH$_3$)$_2$(CH$_2$)$_3$SO$_3$, —NH (CH$_2$)$_2$N$^+$(CH$_3$)$_2$(CH$_2$)$_2$CO$_2$, —NH(CH$_2$)$_3$N$^+$(CH$_3$)$_2$(CH$_2$)$_3$ SO$_3$, —NH(CH$_2$)$_3$N$^+$(CH$_3$)$_2$(CH$_2$)$_2$ CO$_2$, —O(CH$_2$)$_2$N$^+$ (CH$_2$CH$_3$)$_2$(CH$_2$)$_3$SO$_3$, —O(CH$_2$)$_2$N$^+$(CH$_2$CH$_3$)$_2$(CH$_2$)$_2$ CO$_2$, —O(CH$_2$)$_2$N$^+$(CH$_2$CH$_2$CH$_2$CH$_3$)$_2$(CH$_2$)$_3$SO$_3$, —O(CH$_2$)$_2$N$^+$(CH$_2$CH$_2$CH$_2$CH$_3$)$_2$(CH$_2$)$_2$CO$_2$ or —NH (CH$_2$)$_3$Ncyclo-(CH$_2$)$_3$SO$_3$.

In one preferred embodiment, the non-fouling polymeric material is a zwitterionic polymer or copolymer. For example, the non-fouling polymeric material may comprise carboxybetaine repeat units and/or sulfobetaine repeat units. Alternatively, the non-fouling polymeric material may be a polyampholyte, containing anionic and cationic repeat units. Optionally, the non-fouling polymer may contain poly(ethylene oxide) repeat units and/or other neutral olefinic repeat units. Thus, for example, in one preferred embodiment, the non-fouling polymeric material is a zwitterionic polymer or copolymer comprising the repeat units of Formula 4:

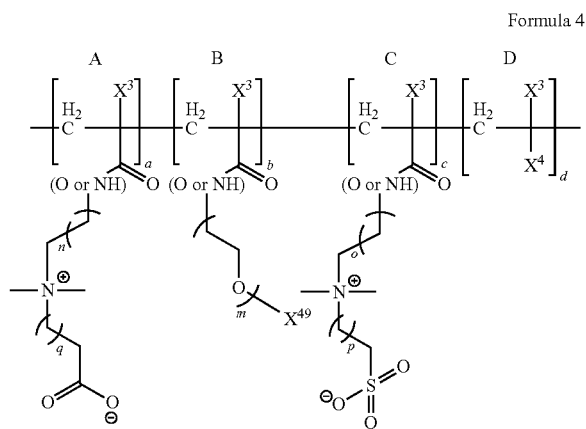

Formula 4 a is 0-1; b is 0-1; c is 0-1; d is 0-1; m is 1-20; n and o are independently 0-11; p and q are independently 0-11; $X^3$ is hydrogen, alkyl or substituted alkyl, $X^4$ is —OX$^{40}$, NX$^{41}$X$^{42}$, —SX$^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, provided the sum of a, b, c and d is greater than 0 and $X^4$ of repeat unit D differs from the corresponding pendant group of repeat units A, B and C. In one such embodiment, $X^3$ is hydroxy-substituted alkyl such as hydroxypropyl.

In one embodiment, it is preferred that the non-fouling polymeric material is a zwitterionic polymer comprising repeat units corresponding to the A and/or the C repeat units. For example, in one embodiment the sum of a and c is at least 0.1. By way of further example, in one embodiment the sum of a and c is at least 0.2. By way of further example, in one embodiment the sum of a and c is at least 0.3. By way of further example, in one embodiment the sum of a and c is at least 0.4. By way of further example, in one embodiment the sum of a and c is at least 0.5. By way of further example, in one embodiment the sum of a and c is at least 0.6. By way of further example, in one embodiment the sum of a and c is at least 0.7. By way of further example, in one embodiment the sum of a and c is at least 0.8. By way of further example, in one embodiment the sum of a and c is at least 0.9. By way of further example, in one embodiment the sum of a and c is at least 0.1 and b is at least 0.1. By way of further example, in one embodiment the sum of a and c is at least 0.2 and b is at least 0.1. By way of further example, in one embodiment the sum of a and c is at least 0.3 and b is at least 0.1. By way of further example, in one embodiment the sum of a and c is at least 0.4 and b is at least 0.1. By way of further example, in one embodiment the sum of a and c is at least 0.5 and b is at least 0.1. By way of further example, in one embodiment the sum of a and c is at least 0.6 and b is at least 0.1. By way of further example, in one embodiment the sum of a and c is at least 0.7 and b is at least 0.1. By way of further example, in one embodiment the sum of a and c is at least 0.8 and b is at least 0.1. By way of further example, in one embodiment the sum of a and c is at least 0.9 and b is at least 0.1. By way of further example, in one embodiment the sum of a and c is at least 0.1 and d is at least 0.1. By way of further example, in one embodiment the sum of a and c is at least 0.2 and d is at least 0.1. By way of further example, in one embodiment the sum of a and c is at least 0.3 and d is at least 0.1. By way of further example, in one embodiment the sum of a and c is at least 0.4 and d is at least 0.1. By way of further example, in one embodiment the sum of a and c is at least 0.5 and d is at least 0.1. By way of further example, in one embodiment the sum of a and c is at least 0.6 and d is at least 0.1. By way of further example, in one embodiment the sum of a and c is at least 0.7 and d is at least 0.1. By way of further example, in one embodiment the sum of a and c is at least 0.8 and d is at least 0.1. By way of further example, in one embodiment the sum of a and c is at least 0.9 and d is at least 0.1. By way of further example, in one embodiment the sum of a and c is at least 0.1, b is at least 0.1 and d is at least 0.1. By way of further example, in one embodiment the sum of a and c is at least 0.2, b is at least 0.1 and d is at least 0.1. By way of further example, in one embodiment the sum of a and c is at least 0.3, b is at least 0.1 and d is at least 0.1. By way of further example, in one embodiment the sum of a and c is at least 0.4, b is at least 0.1 and d is at least 0.1. By way of further example, in one embodiment the sum of a and c is at least 0.5, b is at least 0.1 and d is at least 0.1. By way of further example, in one embodiment the sum of a and c is at least 0.6, b is at least 0.1, and d is at least 0.1. By way of further example, in one embodiment the sum of a and c is at least 0.7, b is at least 0.1 and d is at least 0.1. By way of further example, in one embodiment the sum of a and c is at least 0.8, b is at least 0.1 and d is at least 0.1. By way of further example, in one embodiment the sum of a and c is at least 0.9, b is at least 0.1 and d is at least 0.1. In each of these exemplary embodiments, a may be 0, c may be 0, or a and c may each be greater than 0.

In one preferred embodiment, the non-fouling polymeric material is a zwitterionic polymer or copolymer comprising the repeat units of Formula 4, m is 1-8; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, with the proviso that $X^4$ of the D repeat differs from the corresponding pendant groups of the A, B or C repeat units and a, b, c, and d, in combination, are selected from one of the sets of combinations appearing in Table I:

TABLE I

| Combination | a | b | c | d |
|---|---|---|---|---|
| 1 | 0.1-1.0 | 0.1-0.5 | 0.1-1.0 | 0.1-1.0 |
| 2a | >0 | >0.1 | 0 | 0 |
| 2b | >0 | 0 | 0 | >0.1 |
| 2c | >0 | >0.1 | 0 | >0.1 |
| 3a | >0.1 | >0.1 | 0 | 0 |
| 3b | >0.1 | 0 | 0 | >0.1 |
| 3c | >0.1 | >0.1 | 0 | >0.1 |
| 4a | >0.2 | >0.1 | 0 | 0 |
| 4b | >0.2 | 0 | 0 | >0.1 |
| 4c | >0.2 | >0.1 | 0 | >0.1 |
| 5a | >0.3 | >0.1 | 0 | 0 |
| 5b | >0.3 | 0 | 0 | >0.1 |
| 5c | >0.3 | >0.1 | 0 | >0.1 |
| 6a | >0.4 | >0.1 | 0 | 0 |
| 6b | >0.4 | 0 | 0 | >0.1 |
| 6c | >0.4 | >0.1 | 0 | >0.1 |
| 7a | >0.5 | >0.1 | 0 | 0 |
| 7b | >0.5 | >0 | 0 | >0.1 |
| 7c | >0.5 | >0.1 | 0 | >0.1 |
| 8a | >0.6 | >0.1 | 0 | 0 |
| 8b | >0.6 | 0 | 0 | >0.1 |
| 8c | >0.6 | >0.1 | 0 | >0.1 |
| 9a | >0.7 | >0.1 | 0 | 0 |
| 9b | >0.7 | >0.1 | 0 | >0.1 |
| 9c | >0.7 | 0 | 0 | >0.1 |
| 10a | >0.8 | >0.1 | 0 | 0 |
| 10b | >0.8 | 0 | 0 | >0.1 |
| 10c | >0.8 | >0.1 | 0 | >0.1 |
| 11a | >0.9 | >0.1 | 0 | 0 |
| 11b | >0.9 | 0 | 0 | >0.1 |
| 11c | >0.9 | >0.1 | 0 | >0.1 |
| 12a | 0 | >0.1 | >0 | 0 |
| 12b | 0 | 0 | >0 | >0.1 |
| 12c | 0 | >0.1 | >0 | >0.1 |
| 13a | 0 | >0.1 | >0.1 | 0 |
| 13b | 0 | 0 | >0.1 | >0.1 |
| 13c | 0 | >0.1 | >0.1 | >0.1 |
| 14a | 0 | >0.1 | >0.2 | 0 |
| 14b | 0 | 0 | >0.2 | >0.1 |
| 14c | 0 | >0.1 | >0.2 | >0.1 |
| 15a | 0 | >0.1 | >0.3 | 0 |
| 15b | 0 | 0 | >0.3 | >0.1 |
| 15c | 0 | >0.1 | >0.3 | >0.1 |
| 16a | 0 | >0.1 | >0.4 | 0 |
| 16b | 0 | 0 | >0.4 | >0.1 |
| 16c | 0 | >0.1 | >0.4 | >0.1 |
| 17a | 0 | >0.1 | >0.5 | 0 |
| 17b | 0 | >0 | >0.5 | >0.1 |
| 17c | 0 | >0.1 | >0.5 | >0.1 |
| 18a | 0 | >0.1 | >0.6 | 0 |
| 18b | 0 | 0 | >0.6 | >0.1 |
| 18c | 0 | >0.1 | >0.6 | >0.1 |
| 19a | 0 | >0.1 | >0.7 | 0 |
| 19b | 0 | >0.1 | >0.7 | >0.1 |
| 19c | 0 | 0 | >0.7 | >0.1 |
| 20a | 0 | >0.1 | >0.8 | 0 |
| 20b | 0 | 0 | >0.8 | >0.1 |
| 20c | 0 | >0.1 | >0.8 | >0.1 |
| 21a | 0 | >0.1 | >0.9 | 0 |
| 21b | 0 | 0 | >0.9 | >0.1 |
| 21c | 0 | >0.1 | >0.9 | >0.1 |
| 22a | >0 | >0.1 | >0.7 | 0 |
| 22b | >0 | 0 | >0.7 | >0.1 |
| 22c | >0 | >0.1 | >0.7 | >0.1 |
| 23a | >0.1 | >0.1 | >0.6 | 0 |
| 23b | >0.1 | 0 | >0.6 | >0.1 |
| 23c | >0.1 | >0.1 | >0.6 | >0.1 |
| 24a | >0.2 | >0.1 | >0.5 | 0 |
| 24b | >0.2 | 0 | >0.5 | >0.1 |
| 24c | >0.2 | >0.1 | >0.5 | >0.1 |
| 25a | >0.3 | >0.1 | >0.4 | 0 |
| 25b | >0.3 | 0 | >0.4 | >0.1 |
| 25c | >0.3 | >0.1 | >0.4 | >0.1 |
| 26a | >0.4 | >0.1 | >0.3 | 0 |
| 26b | >0.4 | 0 | >0.3 | >0.1 |
| 26c | >0.4 | >0.1 | >0.3 | >0.1 |
| 27a | >0.5 | >0.1 | >0.2 | 0 |
| 27b | >0.5 | >0 | >0.2 | >0.1 |
| 27c | >0.5 | >0.1 | >0.2 | >0.1 |
| 28a | >0.6 | >0.1 | >0.1 | 0 |
| 28b | >0.6 | 0 | >0.1 | >0.1 |
| 28c | >0.6 | >0.1 | >0.1 | >0.1 |
| 29a | >0.7 | >0.1 | >0 | 0 |
| 29b | >0.7 | >0.1 | >0 | >0.1 |
| 29c | >0.7 | 0 | >0 | >0.1 |

In one embodiment, the non-fouling polymeric material is a polyampholyte zwitterionic polymer or copolymer comprising repeat units corresponding to repeat unit D of Formula 4. That is, d is greater than 0 and a fraction of the repeat units corresponding to repeat unit D are anionic repeat units ($X^4$ for such units is an anionic pendant group) and a fraction of the repeat units corresponding of Formula 4 are cationic repeat units ($X^4$ for such units is a cationic pendant group). For example, in one such embodiment, d is at least 0.1 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.2 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.3 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.4 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.5 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.6 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.7 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.8 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.9 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in each of said examples in this paragraph, the remaining repeat units may correspond to repeat unit A. By way of further example, in each of said examples in this paragraph, the remaining repeat units may correspond to repeat unit B. By way of further example, in each of said examples in this paragraph, the remaining repeat units may correspond to repeat unit C.

More preferably, the non-fouling polymeric material is a zwitterionic polymer or copolymer comprising repeat units corresponding to repeat unit A and/or repeat unit C of Formula 4.

In certain embodiments, the non-fouling polymeric material is a homopolymer or copolymer comprising repeat units corresponding to Formula 5, Formula 6, Formula 7, Formula 8, or Formula 9:

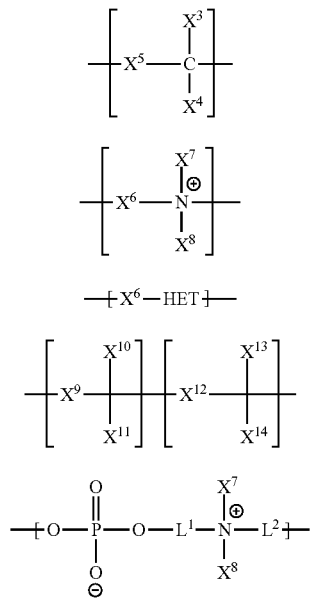

HET is part of a heterocyclic structure,
$X^3$ is hydrogen, alkyl or substituted alkyl,
$X^4$ is —$OX^{40}$, —$NX^{41}X^{42}$, —$SX^{40}$, aryl, heteroaryl or acyl,
$X^5$ is ester, anhydride, imide, amide, ether, thioether, thioester, hydrocarbylene, substituted hydrocarbylene, heterocyclo, urethane, or urea;

$X^6$ is hydrocarbylene, substituted hydrocarbylene, heterocyclo, amide, anhydride, ester, imide, thioester, thioether, urethane, or urea;
$X^7$ is hydrogen, alkyl or substituted alkyl;
$X^8$ is an anionic moiety;
$X^9$ is hydrocarbylene, substituted hydrocarbylene, heterocyclo, amide, anhydride, ester, imide, thioester, thioether, urethane, or urea;
$X^{10}$ is hydrogen, alkyl or substituted alkyl;
$X^{11}$ is a cationic moiety;
$X^{12}$ is hydrocarbylene, substituted hydrocarbylene, heterocyclo, amide, anhydride, ester, imide, thioester, thioether, urethane, or urea;
$X^{13}$ is hydrogen, alkyl or substituted alkyl;
$X^{14}$ is an anionic moiety;
$L^1$ and $L^2$ are independently hydrocarbylene, substituted hydrocarbylene, heterocyclo, amide, anhydride, ester, imide, thioester, thioether, urethane, or urea; and
$X^{40}$ is hydrogen, hydrocarbyl, substituted hydrocarbyl, heterocyclo or acyl, and
$X^{41}$ and $X^{42}$ are independently hydrogen, hydrocarbyl, substituted hydrocarbyl or heterocyclo.

In one embodiment, the non-fouling polymeric material comprises repeat units corresponding to Formula 7 wherein the heterocycle, HET corresponds to Formulae 10, 11 or 12:

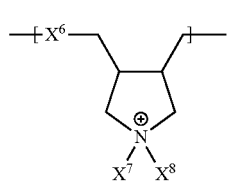

Formula 10

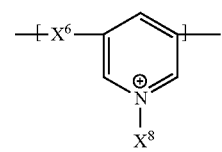

Formula 11

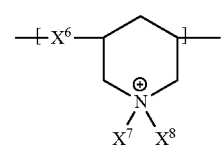

Formula 12 wherein $X^6$ is hydrocarbylene, substituted hydrocarbylene, heterocyclo, amide, anhydride, ester, imide, thioester, thioether, urethane, or urea; $X^7$ is hydrogen, alkyl or substituted alkyl; and $X^8$ is an anionic moiety.

Suitable comonomers include, but are not limited to, acrylates, acrylamides, vinyl compounds, multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams, and combination thereof. In the interests of brevity, exemplary methacrylate monomers are listed below (but it should be understood that analogous acrylate, acrylamide and methacrylamide monomers may be similarly listed and are similarly included):

Charged methacrylates or methacrylates with primary, secondary or tertiary amine groups, such as, 3-sulfopropyl methacrylate potassium salt, (2-dimethylamino)ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino)ethyl methacrylate, 2-(tert-butylamino)ethyl methacrylate, and 2-(tert-butylamino-ethyl methacrylate.

Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

Reactive or crosslinkable methacrylates, such as 2-(trimethylsilyloxy)ethyl methacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate 3-(dimethylchlorosilyl)propyl methacrylate 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Multifunctional monomers, such as di, tri, or tetraacrylates and di, tri, or tetraacrylamides can be used to form highly branched structures which can provide a higher concentration of non-fouling groups on the surface. As previously noted, the non-fouling polymeric material may contain a non-zwitterionic non-fouling material, alone or in combination with a zwitterionic material. These non-fouling groups may have varying degrees of non-fouling performance in a range of environments. Suitable non-zwitterionic materials include, but are not limited to, polyethers, such as polyethylene glycol, poly(ethylene oxide-co-propylene oxide) (PEO-PPO) block copolymers, polysaccharides such as dextran, hydrophilic polymers such as polyvinylpyrrolidone (PVP) and hydroxyethyl-methacrylate (HEMA), acrylonitrile-acrylamide copolymers, heparin, heparin fragments, derivatized heparin fragments, hyaluronic acid, mixed charge materials, and materials containing hydrogen bond accepting groups, such as those described in U.S. Pat. No. 7,276,286. Suitable polymer structures included, but are not limited to, polymers or copolymers containing monomers of Formula I wherein ZI is replaced by a non-zwitterionic, non-fouling head group.

In one embodiment, the non-fouling material is a polymer containing repeat units derived from sulfobetaine-containing and/or carboxybetaine-containing monomers. Examples of monomers include sulfobetaine methacrylate (SBMA), sulfobetaine acrylamide, sulfobetaine methacrylamide, carboxybetaine methacrylate (CBMA), carboxybetaine acrylamide and carboxybetaine methacrylamide. Examples of such polymers include, but are not limited to, poly(carboxy betaine methacrylate) (polyCBMA), poly(carboxybetaine acrylamide), poly(carboxybetaine methacrylamide) poly(sulfobetaine methacrylate) (polySBMA), poly(sulfobetaine acrylamide), and poly(sulfobetaine methacrylamide). In another embodiment, the non-fouling material polymer is a polymer containing the residue of CBMA or SBMA and one or more additional monomers. The additional monomers can be zwitterionic or non-zwitterionic monomers.

In some embodiments, it is preferred to have use zwitterionic polymers that possess permanently charged groups, which, without being bound by any theory, may improve non-fouling performance because the charged groups are ionically solvated with water. The presence of commonly used groups which can have permanent charges in the zwitterionic polymers can be detected by using XPS to analyze the elements present in the top approximately 1-50 nm of the surface. One representative group commonly used in zwitterions is nitrogen in quaternary amine groups. In sulfobetaine, elemental signal of nitrogen may be approximately equivalent to a signal for sulfur. Further, techniques such as TOF—SIMS may be used to identify zwitterionic groups in the grafted polymer layer. In some preferred embodiments, the grafted polymer layer contains XPS signals of nitrogen, and optionally sulfur.

The polymeric surface modifications of the present invention may be formed by synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical initiated polymerization. In a preferred embodiment, the polymer is formed using an oxidizing agent and a reducing agent, in combination, i.e., a redox pair, as the polymerization initiator in a redox free radical polymerization.

In some embodiments, it is preferable that initiators and ligands often used in ATRP such as bromine-containing initiators and ligands such as bipyridine are not used in the process as they may be non-biocompatible at certain levels. In further embodiments, it is preferred not to have a detectable level of bipyridine in the polymer modified article or in aqueous or organic extractions of the polymer modified article. In further embodiments, it is preferred not to have a detectable level of bromine in the polymer modified article or in aqueous or organic extractions of the polymer modified article. Bipyridine and bromine can be detected with one or a combination of HPLC, HPLC-MS, UV, ion chromatography, combustion analysis, ICP-MS, EDS, and XPS analysis.

The general procedure described herein can be modified as necessary to accommodate different substrate materials, initiators systems, and/or monomer compositions and to incorporate high concentrations of the initiator into and/or onto the substrate or undercoating layer. High initiator concentrations may result in highly densely coated surfaces which improves the non-fouling activity of the composition. For example, highly densely coated surfaces contain polymer chains that reduce penetration of fouling molecules into the coating. Without being bound to any particular theory it is presently theorized that a reservoir of initiator incorporated in the substrate may enhance re-initiation and branching of non-fouling polymer from the surface and near the surface of the substrate.

This re-initiation, in turn, may increase the thickness of the non-fouling polymer (in other words, the distance the non-fouling polymer stretches above the substrate in a direction normal to the substrate surface) as well as the degree of branching.

As described in greater detail elsewhere herein, incorporation of initiator into the substrate enables polymeric material to be grafted from the surface and from within the near-surface zone. In general, however, it is preferred that polymeric material not extend too far into the substrate; thus, in one embodiment polymeric material is present in the near-surface zone but not at greater depths, i.e., not in the bulk. The maximum depth to which near-surface zone extends, i.e., the distance of the lower boundary from the surface is, at least in part, a function of the initiator and the technique used to incorporate initiator in the substrate. Typically, however, it is generally preferred that the lower boundary not be greater than 20 micrometers from the surface. By way of example, the lower boundary may not be greater than 15 micrometers from the surface. By way of further example, the lower boundary may not be greater than 10 micrometers from the surface. Similarly, the minimum depth of the near-surface zone, i.e., the distance of the upper boundary from the surface is, at least in part, also a function of the initiator and the technique used to incorporate initiator in the substrate. Typically, however, the upper boundary will be at least 0.1 micrometers from the surface. By way of example, the upper boundary may be at least 0.2 micrometers from the surface. By way of further example, the upper boundary may be at least 0.3 micrometers from the surface.

The quality of the surface modification formed in the polymerization process is, at least in part, influenced by the quality of the surface of the substrate prior to polymerization. For example, prior to polymerization, the surface may be contaminated, intentionally or otherwise, with particles, waxes and other compositions that may remain on the surface of the substrate as an artifact of the manufacturing process, subsequent handling of the substrate, and/or as part of the intended substrate composition. The substrate surface may also include significant surface roughness, physical defects such as scratches, pinholes, or voids, and chemical defects, such as particle(s) of radiopacifing agents (such as barium sulfate, bismuth oxychloride, bismuth subcarbonate, bismuth trioxide, lanthanum oxide, tantalum pentoxide, and metallic gold, silver, platinum, palladium, tungsten, and tantalum) that are only partially contained within the substrate. For example, substrates containing barium sulfate typically have some barium sulfate particles that are partially contained within the substrate and partially exposed; the exposed portions of such barium sulfate particles may extend from the surface of a substrate to a height of as much as 1 micrometer (as measured from the surface of the substrate using SEM).

In accordance with one embodiment, the substrate surface is preferably pre-treated prior to polymerization as discussed in detail above. For example, the substrate surface may be treated using water, solvents, surfactant solutions, enzymes, or other cleaning solutions or gases to reduce or substantially or completely remove particles, waxes or other foreign compositions that may be on or near the surface of the substrate. Alternatively, or additionally, the substrate surface may be mechanically, chemically, thermally, or chemomechanically treated to reduce the incidence and/or the severity of physical and chemical defects.

In one embodiment, the substrate is treated prior to polymerization with a composition such as an acid, base, chelator or reactant that dissolves or chemically reacts with and reduces the concentration of any compositions that are included as chemical defects, or even swells the substrate allowing the particles to be released from the substrate. For example, exposed portions of barium sulfate particles may be partially or completely dissolved using a mineral or organic acid and optionally, a chelator. In one such exemplary embodiment, polyurethane comprising particles of barium sulfate may be treated with hydrochloric acid to at least partially remove exposed barium sulfate particles. Representative acids include, for example, hydrochloric acid, sulfuric acid, nitric acid, phosphoric acid, boric acid, hydrofluoric acid, hydrobromic acid, lactic acid, acetic acid, carbonic acid, formic acid, citric acid, oxalic acid, uric acid, carboxylic acids, sulfonic acids, chlorous acid, and the like. Representative bases include, for example, sodium hydroxide, potassium hydroxide, ammonia solution, sodium chlorite, and the like. Representative chelators include, for example, water, carbohydrates, including polysaccharides, organic acids with more than one coordination group, lipids, steroids, amino acids and related compounds, peptides, phosphates, nucleotides, tetrapyrrols, ferrioxamines, ionophores, such as gramicidin, monensin, valinomycin, phenolics, 2,2'-bipyridyl, dimercaptopropanol, ethylenediaminotetraacetic acid, EDTA, ethylenedioxy-diethylene-dinitrilo-tetraacetic acid, EGTA, ethylene glycol-bis-(2-aminoethyl)-N,N,N', N'-tetraacetic acid, nitrilotriacetic acid, NTA, ortho-phenanthroline, salicylic acid, triethanolamine, TEA, 5-sulfosalicylic acid, oxalic acid, citric acid, tartaric acid, ethylene glycol-bis (2-aminoethylether)-N,N,N',N'-tetraacetic acid, enterobactin, ethylenediaminetetra(methylenephosphonic acid) and corresponding salts, and the like. Certain preferred chelators are polyamino carboxylic acids, e.g., glycine, beta-alanine, iminodiacetic acid (IDA), nitrilotriacetic acid (NTA), ethylenediaminetetraacetic acid, (EDTA), diethylene triamine pentaacetic acid (DTPA), 1,2-bis(o-aminophenoxy)ethane-N,N,N',N'-tetraacetic acid (BAPTA), 1,4,7,10-tetraazacyclododecane-1,4,7,10-tetraacetic acid (DOTA), and the like.

Alternatively, or additionally, the substrate may be chemically, mechanically, thermally, or chemomechanically polished prior to polymerization to reduce surface roughness, reduce the incidence and/or severity of cracks, pinholes and other structural defects in the substrate surface. For example, the substrate may be solvent polished by exposing the substrate to a vapor of a solvent such as chloroform, dioxane or tetrahydrofuran. After polishing the substrate surface preferably has a global average $R_{rms}$ surface roughness that is less than the global average $R_{rms}$ surface roughness of the unpolished substrate. By way of further example, in one embodiment the polished substrate surface has a global average $R_{rms}$ surface roughness that is no more than 90% of the global average $R_{rms}$ surface roughness of the unpolished substrate surface. By way of further example, in one embodiment the polished substrate surface has a global average $R_{rms}$ surface roughness that is no more than 75% of the global average $R_{rms}$ surface roughness of the unpolished substrate surface. By way of further example, in one embodiment the polished substrate surface has a global average $R_{rms}$ surface roughness that is no more than 50% of the global average $R_{rms}$ surface roughness of the unpolished substrate surface.

Regardless of the pre-treatment steps, or even whether pre-treatment steps are employed, the surface of the substrate from which the non-fouling material is to be grafted has a global average $R_{rms}$ surface roughness that is no more than 200 nm. In one embodiment, for example, the surface of the substrate from which the non-fouling material is to be grafted has a global average $R_{rms}$ surface roughness of no more than 150 nm; more preferably in this embodiment, the surface has a global average $R_{rms}$ surface roughness of no more than 100 nm. In certain embodiments, the surface is even smoother. For example, the surface may have a global average $R_{rms}$ surface roughness of less than 50 nm. In some embodiments, the surface may have a global average $R_{rms}$ surface roughness of less than 20 nm.

Additionally, or alternatively, and regardless of the pre-treatment steps, or even whether pre-treatment steps are employed, the surface of the substrate from which the non-fouling material is to be grafted has a visually observable surface defect density (i.e., visually observable number over a field size of 20×20 micrometers) of defects having a size (i.e., a longest dimension) greater than about 0.5 micrometers that is less than 0.1 defects/$\mu m^2$. For example, the surface of the substrate from which the non-fouling material is to be grafted may have a surface defect density of defects having a size greater than about 0.5 micrometers that is less than 0.05 defects/$\mu m^2$. By way of further example, the surface of the substrate from which the non-fouling material is to be grafted may have a surface defect density of defects having a size greater than about 0.5 micrometers that is less than 0.01 defects/$\mu m^2$. By way of further example, the surface of the substrate from which the non-fouling material is to be grafted may have a surface defect density of defects having a size greater than about 0.5 micrometers that is less than 0.002 defects/$\mu m^2$. By way of further example, the surface of the substrate from which the non-fouling material is to be grafted may have a surface defect density of defects having a size greater than about 0.5 micrometers that is less than 0.001 defects/$\mu m^2$.

The average thickness of a polymeric surface modification or coating on a substrate can be approximated using attenuated total reflectance (ATR) infrared spectrometry if the infrared spectra and refractive indices of the typical polymeric surface material and the typical substrate material can be determined independently and if the range of the modification or coating thickness is between 10 nm and 5000 nm. A matrix of synthetic infrared absorbance spectra can be constructed using the principal component spectra (those of the coating material and the substrate material) and Beer's law ($A=\epsilon bC$) where b, the optical path length, is replaced by the exponentially decaying and wavelength dependent depth of penetration of the ATR evanescent wave. An empirically measured sample is then compared across all the synthetic spectra in the matrix and the closest match, determined by the minimum n-dimensional cosine statistical distance, is the one of the sample's polymeric surface modification or coating thickness.

For example, the average thickness of a homopolymeric SBMA (N-(3-sulfpropyl)-n-methacryloxyethyl-n,n-dimethylammonium betaine) hydrogel surface modification or coating on a polyetherurethane plus 10% to 50% $BaSO_4$ substrate can be approximated using attenuated total reflectance (ATR) infrared spectrometry if the range of the modification or coating thickness is between 10 nm and 5000 nm and the $BaSO_4$ content of the substrate is constant to within +/−5%. The value of the absorbance of the vibrational SO3 stretch at 1037.0 $cm^{-1}$ (point baseline corrected by subtracting the absorbance value at 994.7 $cm^{-1}$) divided by the value of the absorbance of the urethane peak at 1309.5 $cm^{-1}$ (point baseline corrected by subtracting the absorbance value at 1340.0 $cm^{-1}$) equals a value relative to the concentration of SBMA present.

To induce small polymerization initiator molecules to concentrate at or near the substrate surface, where polymerization is initiated and propagated, polymerization mixture solvent systems with surface tensions of a magnitude differing from the surface energy of the substrate and one or more polymerization initiators having limited solubility in the polymerization mixture solvent system are selected. The surfaces of the substrate from which the non-fouling material is to be grafted surfaces may be hydrophobic or hydrophilic, and the polymerization mixture solvent system may be aqueous, comprise polar organic solvents, aqueous mixtures of polar organic solvents, or aqueous mixtures of any organic compound designed to modify the surface tension of aqueous solutions. Optionally, for hydrophobic substrates, hydrophobic initiator(s) and hydrophilic solvent systems, e.g., aqueous media are selected. Preferably, if the substrate is hydrophilic, at least one hydrophilic initiator and a non-polar organic solvent system is selected.

Preferably, the substrate (or at least the portion of the substrate into which the polymerization initiator is incorporated) is not significantly swelled by the polymerization mixture (e.g., by the polymerization mixture solvent system, the polymerization monomers, or both) and the initiator(s) incorporated into the substrate has/have limited solubility in the solvent system. As a result, the interface between substrate surface and the polymerization mixture can have a relatively high local concentration of initiator(s) to initiate non-fouling polymer growth from or near the substrate surface and to (re)initiate polymer growth from the grafted non-fouling polymer. Without being bound to any particular theory, it is presently believed that this approach leads to the grafting of a relatively highly branched non-fouling polymer from the substrate.

In a preferred embodiment, the substrate polymer from which the non-fouling polymer will be grafted will not swell more than 30% by volume at 25° C. under equilibrium conditions in the polymerization mixture solvent system. In certain embodiments, the substrate polymer from which the non-fouling polymer will be grafted will not swell more than 15% by volume at 25° C. under equilibrium conditions in the polymerization mixture solvent system. In certain embodiments, the substrate polymer from which the non-fouling polymer will be grafted will not swell more than 5% by volume at 25° C. under equilibrium conditions in the polymerization mixture solvent system. In certain embodiments, the substrate polymer from which the non-fouling polymer will be grafted will not swell or may even shrink at 25° C. under equilibrium conditions in the polymerization mixture solvent system. As previously noted, the substrate may be a composite of materials. In such instances, it is preferred that the near-surface region of the substrate into which the polymerization initiator is incorporated satisfy the swelling criteria recited herein. For example, in those embodiments in which the substrate comprises a coating of a precoat material overlying a metal, ceramic, glass or semi-metallic material, it is preferred that the coating of the precoat material not swell more than 30% by volume at 25° C. under equilibrium conditions in the polymerization mixture solvent system.

The initiator(s) incorporated into the substrate preferably have limited solubility in the solvent system comprised by the polymerization mixture and include any of the initiators identified herein. In general, it is preferred that the incorporated initiator(s) have a 10 hour T1/2 decomposition temperature of 25-175° C. In one particular embodiment, the incorporated initiator(s) have a 10 hour T1/2 decomposition temperature of 70-130° C. Advantageously, having a 10 hour T1/2 decomposition temperature of 70-130° C. tends to increase the density of interfacial initiation events from the redox reaction and effectively outcompete thermal initiation.

As described elsewhere herein, the initiator may comprise a redox pair; in such embodiments, at least one member of such pair have such a limited solubility in the polymerization mixture solvent system. In one embodiment, both members of the redox pair have limited solubility in the polymerization mixture solvent system. In an alternative embodiment, one member of the pair is soluble in the polymerization mixture solvent system but the other has limited solubility in the polymerization mixture solvent system. Without being bound to any particular theory, it is presently believed that when one member of a redox pair is soluble in the polymerization mixture solvent system and the other has limited solubility in the polymerization mixture solvent system, the two are phase separated and initiation is enhanced at the interface of the two phases which tends to decrease solution polymerization and increase grafting at or near the substrate surface. Thus, for example, either member of the redox pair may be hydrophobic and either member of the pair may be hydrophilic, provided at least one of the members has limited solubility in the polymerization mixture solvent system. In one preferred embodiment, a hydrophobic oxidizer is paired with a hydrophilic reducing agent. In another preferred embodiment, a hydrophilic oxidizer is paired with a hydrophobic reducing agent. For example, in one embodiment, the redox pair comprises a peroxide and a reducing agent wherein the peroxide has limited solubility in the polymerization solvent system and the reducing agent has high solubility in the polymerization solvent system. By way of further example, in certain embodiments, the peroxide has a log P partition coefficient greater than or equal to 3 for hydrophobic substrates and phases and a log P partition coefficient less than 3 for hydrophilic substrates and phases. By way of further example, in certain embodiments, the peroxide has a log P partition coefficient greater than or equal to 5 for hydrophobic substrates and phases and a log P partition coefficient less than 1 for hydrophilic substrates and phases. By way of further example, in certain embodiments, the peroxide has a log P partition coefficient greater than or equal to 7 for hydrophobic substrates and phases and a log P partition coefficient less than −1 for hydrophilic substrates and phases. By way of further example, in certain embodiments, the peroxide has a log P partition coefficient greater than or equal to 9 for hydrophobic substrates and phases and a log P partition coefficient less than −3 for hydrophilic substrates and phases.

In one embodiment, an initiator is incorporated into the substrate by initially incorporating an initiator-precursor into the substrate and activating the initiator-precursor to an initiator.

In accordance with one aspect of the present invention, the polymerization initiator(s) may be incorporated into and/or onto the substrate by various techniques. In one such method, the substrate (including substrates having precoat or undercoat as previously described) is imbibed with the polymerization initiator; that is, the polymerization initiator is absorbed into the substrate. In one embodiment, the initiator(s), i.e., an initiator or a mixture of different initiators, is introduced into and/or onto the substrate's surface by physio-adsorption, wherein the initiator is dissolved in a solvent or combination of solvents and the substrate (with or without an undercoating layer) is submerged in the mixture for a time and at a temperature to achieve sufficient absorption by the substrate. The substrate is allowed to swell ultimately imbibing initiator into the substrate. In general, the amount of initiator incorporated into a substrate during the soak will, at least in part, be a function of the, solubility of the initiator in the solvent system, solubility of the initiator in the substrate as well as the soak time, temperature and concentration of the initiator in the solution, as well as the chemical composition of the substrate and the initiator.

In a preferred embodiment, the surface of the substrate to be imbibed with the polymerization initiator(s) comprises a polymer, natural or synthetic. In an alternative embodiment, the substrate is an imbibable material selected from among polymers, natural or synthetic, biological tissues, living or dead, woven non-woven fibers, and combinations thereof. Certain (uncoated) substrates such as a metal, ceramic, glass, and semi-metallic substrates lack the capacity to absorb sufficient initiator. In general, therefore, for these substrates it is preferred to precoat the surface of the metal, ceramic, glass or semi-metallic substrate with an undercoating or precoating, from which the polymeric material may be grafted. For example, metal, ceramic, glass, and semi-metallic substrates may be precoated with a polymer selected from polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof, and the precoated substrate is then imbibed as previously described.

The quantity of initiator introduced to the substrate can be controlled by changing the concentration of the initiator in the solvent solution and/or by changing the amount of time the substrate is allowed to soak in the initiator solution during one initiator imbibing period or by repeating any number of initiator imbibing periods as required. Temperature is not narrowly critical, with temperatures in the range of room temperature to elevated temperatures being typical. When utilizing multiple periods of initiator imbibing, the initiator used in the subsequent imbibing periods can be the same as, different from, or a mixture with the initiator used in the previous initiator imbibing period. In general, the substrate is immersed in the initiator-containing solution for at least several seconds before polymerization is initiated. In some embodiments, the substrate is immersed in the initiator-containing solution for longer times. For example, the substrate may be immersed in the initiator-containing solution for at least several minutes. By way of further example, the substrate may be immersed in the initiator-containing solution for at least about 15 minutes before polymerization is initiated. In some embodiments, the substrate will be immersed in the initiator-containing solution for at least 1 hour at room temperature or elevated temperatures for initiators having a 10 hour T1/2 decomposition temperature of 70-130° C. before polymerization is initiated. In further embodiments, the substrate will be immersed in the initiator-containing solution for at least 2 hour before polymerization is initiated. In yet further embodiments, the substrate will be immersed in the initiator-containing solution for at least 16 hour before polymerization is initiated. Depending upon the time, temperature and concentration of initiator in the initiator-containing solution, a concentration gradient of initiator in the substrate may be established. In some embodiments, it may be preferable to have a higher concentration of initiator in the substrate nearer to the surface. As noted, the initiator may be present in a range of concentrations in the initiator-containing solution. For example, in some embodiments, the concentration of the initiator will generally be at least 0.1% by weight. In some embodiments, the concentration will be even greater, e.g., at least 0.5% by weight. In some embodiments, the concentration will be even greater, e.g., at least 1% by weight. In some embodiments, the concentration will be even greater, e.g., at least 10% by weight. In each of these embodiments, the initiator is preferably one of the UV, thermal or redox initiators described elsewhere herein.

The solvent used to imbibe the substrate with initiator may have the capacity to swell the substrate (or at least the portion of the substrate to be imbibed with initiator) to various degrees. Typically, the imbibing solvent swells the substrate (or at least the portion of the substrate to be imbibed with initiator) less than 900% by volume at room temperature and ambient pressure. For example, in one such embodiment, the imbibing solvent swells the substrate (or at least the portion of the substrate to be imbibed with initiator) less than 100% by volume. By way of further example, in one such embodiment, the imbibing solvent swells the substrate (or at least the portion of the substrate to be imbibed with initiator) less than 100% by volume. By way of further example, in one such embodiment, the imbibing solvent swells the substrate (or at least the portion of the substrate to be imbibed with initiator) less than 25% by volume. In a preferred embodiment, the imbibed substrate is preferably washed using a solvent, optionally with a solvent that swells that substrate, and optionally dried. In other embodiments, the substrate is washed with solvents, which may be the same or different from the imbibing solvents, or the substrate may not be washed. For example, the wash solvent may swell the substrate, shrink the substrate, or neither. In one embodiment, the substrate is dried, partially dried or not dried. Optionally, there may be a solvent exchange.

In an alternative method, the initiator(s) is/are incorporated into the substrate by co-deposition of the initiator(s) as a component of a coating, i.e., a precoating or undercoating as described herein, on the surface of the substrate. For example, a thin film of polymer and initiator are deposited onto the substrate by dipping the substrate in a solution of initiator(s) and polymer. Alternatively, a precoat layer of a flowable mixture of the initiator(s) and a second material such as a polymeric material are deposited onto the surface of the substrate. The precoating may thus be applied to any of the substrates described herein, including metals, ceramics, glasses, polymers, biological tissues, living or dead, woven and non-woven fibers, semi-metals such as silicon. For example, the metal, ceramic, glass, polymer, biological tissue, fiber, or semi-metal may be precoated with a polymer and initiator mixture wherein the polymer is selected from polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof.

In some embodiments, one or more solvents or other reactants used in a surface treatment to dissolve or clean up processing materials, surface materials, artifacts, and other components as described above, may also introduce a polymerization initiator to the substrate. Thus, the surface treatment/imbibing process may optionally be accompanied by mechanical agitation (e.g., sonication) and/or elevated temperatures, for example, to promote dissolution or removal of the low molecular weight species (e.g., substrate surface materials or processing materials) and other flaws (e.g., surface roughness) and/or to enhance the imbibing process.

In one embodiment, the amount of initiator co-deposited with the polymer is relatively great. In certain embodiments, for example, the weight ratio of initiator to polymer co-deposited will be at least 1:1000, respectively. In some embodiments, the weight ratio of initiator to polymer co-deposited will be even greater, e.g., at least 1:100, 1:10, 1:1, 10:1, 100:1, or 1000:1 respectively. Typically, the ratio of initiator to polymer will be in the range of about 1:1 to about 20:1. In addition, the co-deposited layers (i.e., the layers containing co-deposited initiator and polymer) will have a thickness of at least 100 nm. For example, in one embodiment, the co-deposited layer will have a thickness of about 100 nm to about 500 micrometers. In each of these embodiments, the initiator is preferably one of the UV, thermal or redox initiators described elsewhere herein.

Monomers can be selected such that their reactivity ratios give alternating copolymers, periodic copolymers with a pre-specified ratio of each monomer, random copolymers, block copolymers or homopolymers. Inclusion of more than two reactive groups on each monomer unit allows for the formation of star polymers, dendrimers, regularly branched polymers, randomly branched polymers, and brush polymers. In general, the monomer may be selected from any of the monomers disclosed herein. Thus, for example, the monomers may contain any of the pendant groups corresponding to Formulae ZI-1 to ZI-7. By way of further example, upon polymerization the monomers may provide the polymer with repeat units corresponding to any of Formula 1-12. In a preferred embodiment, the monomers are miscible with the polymerization mixture solvent system.

In processes for modification of the surface of a hydrophobic substrate, a hydrophilic solvent system preferably is employed. Aqueous solutions preferably are used as the solvent system, optionally containing ions or buffers, such as sodium, ammonium, potassium, chloride, phosphate, or acetate. In processes for modifying hydrophilic substrates, a hydrophobic solvent system preferably is used. In such processes, the preferred media is an organic solvent, typically a non-polar organic solvent, or a mixture thereof. Exemplary organic solvents include one or more of toluene, hexane, cyclohexane, benzene, xylene, tetrahydrofuran, and aliphatic alcohols. In a preferred embodiment, the solvent system does not swell the substrate (or at least that portion of the substrate from which the polymer will be grafted) by more than 25% by volume. For example, in one such embodiment, the solvent system does not swell the substrate (or at least that portion of the substrate from which the polymer will be grafted) by more than 10% by volume. In a preferred embodiment, the solvent system does not swell the substrate (or at least that portion of the substrate from which the polymer will be grafted) by more than 5% by volume. In one embodiment, the solvent system may even shrink the substrate (or at least that portion of the substrate from which the polymer will be grafted).

In one particularly preferred embodiment, the non-fouling polymeric materials are grafted from the substrate by chain growth addition polymerization. The polymerization conditions described herein are generally mild compared to other methods of polymerization and thus do not significantly alter the mechanical properties, flexibility, or dimensional properties of the underlying substrate. In one preferred embodiment, for example, polymerization is carried out at a temperature not in excess of 60° C. The polymerization may be carried out over a relatively wide pH range, e.g., about 0-10. In one embodiment, the polymerization reaction is carried out at a pH of about 2-8. For example, when DCP and ferrous gluconate are used as redox pair, the polymerization reaction may be carried out at a pH of about 6-8. By way of further example, when benzoyl peroxide and ferrous gluconate are used as redox pair, the polymerization reaction may be carried out at a pH of about 4-6. By way of further example, when TBEC and ferrous gluconate are used as redox pair, the polymerization reaction may be carried out at a pH of about 5-7.

Examples of radical polymerization processes include, but are not limited to, UV, thermal, and redox initiated processes. In particular embodiments, the polymer is grafted from the substrate, by first incorporating one or more initiators, such as an ultraviolet (UV), thermal, or redox initiator into the substrate and initiating polymerization of one or more monomers from the surface. Preferably, the initiator is incorporated into the substrate by imbibing the substrate with initiator or coating the substrate with a layer, e.g., an undercoating layer (sometimes referred to herein as the co-deposited layer), comprising the initiator. The polymerization is typically initiated by exposing the initiator-imbibed substrate with a solution or suspension of the monomer or monomers to be polymerized. The quantity of polymer introduced to the substrate can be controlled by changing the concentration of the polymer in the solvent solution, surface tension of the polymer solution, polymerization temperature, pH of the polymer solution, polymerization solution agitation or flow conditions, by changing the amount of time the substrate is allowed to be in the polymer solution during one polymerization period, and/or by repeating any number of polymerization periods as required. When utilizing multiple polymerization periods, the polymer(s) used in the subsequent polymerization periods can be the same as, different from, or a mixture with the polymer(s) used in the previous polymerization period.

Chain transfer agents can be added to the monomer solution to mediate the graft from radical polymerization reaction kinetics. Chain transfer agents include, but are not limited to, molecules containing halocarbons, thiols, dithiocarbamates, trithiocarbonates, dithioesters, xanthates, primary or secondary alcohols. Examples of chain transfer agents are bromotrichloromethane, 4-methylbenzenethiol, benzyl alcohol, methanol, ethanol, ethyleneglycol, glycerol, and isopropanol. In one embodiment the radical polymerization graftings are mediated using 2,2,6,6-tetramethylpiperidinie-1-oxyl (TEMPO). In one embodiment the radical polymerization graftings are mediated using reversible addition fragmentation transfer (RAFT) agents. Examples of RAFT agents include 2-(Dodecylthiocarbonothioylthio)-2-methylpropionic acid, 2-Cyano-2-propyl benzodithioate, 2-Cyano-2-propyl dodecyl trithiocarbonate, 4-Cyano-4-(phenylcarbonothioylthio)pentanoic acid, 4-Cyano-4-[(dodecylsulfanylthiocarbonyl)sulfanyl]pentanoic acid, Bis(dodecylsulfanylthiocarbonyl)disulfide, Bis(thiobenzoyl)disulfide, Cyanomethyl dodecyl trithiocarbonate, Cyanomethyl methyl(phenyl)carbamodithioate, and their analogues and derivatives Oxygen can act as an inhibitor in free radical polymerization as it can react quickly with the free radicals generated by the initiator to form stable radical species, which in turn can react with other radical species to form unreactive species which terminate the polymerization. Therefore, creating an oxygen-free environment by degassing with nitrogen or argon or vacuum is typically used to remove oxygen before and during polymerization. However, for certain embodiments, it would preferable not to require such degassing steps in commercial production. In one preferred embodiment, the polymerization method is other than ATRP, which typically requires stringent control of oxygen levels that may be difficult to achieve during manufacturing.

Alternatively, oxygen in the system can be minimized by filling the reactor with the reaction mixtures thus physically displacing the oxygen in the reactor. In another embodiment, reagents which scavenge oxygen can be added to the reaction mixture. Suitable oxygen-scavenging reagents include, but are not limited to, sodium (meta) periodate, riboflavin, and ascorbic acid. These agents may improve the efficacy of the resulting polymer if the polymerization does not employ an inert atmosphere.

In addition to monomer and a solvent system, the polymerization mixture may optionally contain a free radical inhibitor to encourage surface grafting. Without being bound to any particular theory, it is presently believed that the addition of a free radical inhibitor, including, hydroquinone, hydroquinone monomethyl ether, phenothiazine, 3,7-bis(dimethylamino)phenazathionium chloride, triethylene diamine, t-butylcatechol, butylated hydroxytoluene, and 4-t-butylphenol to the grafting solution decreases solution polymerization, thereby allowing more monomer to be available for grafting at or near the substrate surface/polymerization mixture interface.

Plasticizers can be incorporated into the grafted polymer at any time during and/or subsequent to surface polymerization. In the preferred embodiment, a hydrophilic plasticizer (such as citrated esters, ethylene glycol, propylene glycol, and/or polyethylene glycol (<2000 $M_w$]) is incorporated into the grafted polymer in a post-polymerization aqueous wash period.

i. UV Initiators

In one embodiment, the initiator is an ultraviolet (UV) initiator. The substrate and initiator are typically placed into an aqueous, degassed, solution containing a zwitterionic monomer and exposed to UV light, initiating the radical polymerization. In one exemplary embodiment, the UV light has a peak wavelength of 365 nm, generated by a 100 W UV.

Examples of UV radical initiators include, but are not limited to, 1-Hydroxycyclohexyl phenyl ketone, 2,2-Diethoxyacetophenone, 2-Benzyl-2-(dimethylamino)-4'-morpholinobutyrophenone, 2-Hydroxy-2-methylpropiophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 4,4'-Dimethylbenzil, Benzoin ethyl ether, Benzoin isobutyl ether, Benzoin methyl ether, Benzoin, 2-Methylbenzophenone, 3,4-Dimethylbenzophenone, 3-Hydroxybenzophenone, 3-Methylbenzophenone, 4,4'-Bis(diethylamino)benzophenone, 4,4'-Dihydroxybenzophenone, 4,4'-Bis[2-(1-propenyl)phenoxy]benzophenone, 4-(Diethylamino)benzophenone, 4-Benzoylbiphenyl, 4-Hydroxybenzophenone, 4-Methylbenzophenone, Benzophenone-3,3',4,4'-tetracarboxylic dianhydride, Benzophenone, Methyl benzoylformate, Michler's ketone, Sulfoniums, iodiums, 2-(4-Methoxystyryl)-4,6-bis(trichloromethyl)-1,3,5-triazine, Diphenyliodonium p-toluenesulfonate, N-Hydroxy-5-norbornene-2,3-dicarboximide perfluoro-1-butanesulfonate, N-Hydroxynaphthalimide triflate, 2-tert-Butylanthraquinone, 9,10-Phenanthrenequinone, Anthraquinone-2-sulfonic acid sodium salt monohydrate, Camphorquinone, Diphenyl(2,4,6-trimethylbenzoyl)phosphine oxide, 10-Methylphenothiazine, thioxanthones, and IRGRCURE 2959.

ii. Thermal Initiators

In another embodiment a heat activated (thermal) initiator is used, in place of the UV initiator described above, and the graft from polymerization is initiated by heating the aqueous monomer solution temperature to a desired temperature and holding the temperature constant until the desired degree of polymerization is achieved.

Suitable thermal initiators include, but are not limited to, tert-Amyl peroxybenzoate, 4,4-Azobis(4-cyanovaleric acid), 2,2'-Azobis[(2-carboxyethyl)-2-methylpropionamidine], 2,2'-Azobis(4-methoxy-2,3,-dimethylvaleronitrile), 1,1'-

Azobis(cyclohexanecarbonitrile), 2,2'-Azobisisobutyronitrile (AIBN), Benzoyl peroxide, 2,2-Bis(tert-butylperoxy) butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, Potassium persulfate.

The temperature to which the solution is heated is dependent, among other things, on the monomer and/or the initiator, and/or the substrate. Examples of thermal radical initiators include, but are not limited to, azo-compounds such as azobisisobutyronitrile (AIBN) and 1,1'-Azobis(cyclohexanecarbonitrile) (ABCN). Preferable grafting temperatures are near the 10 hour T1/2 of the initiator selected. The graft from radical polymerization reaction can be thermally quenched by heating beyond the initiators half life.

iii. Redox Initiators

In another embodiment, a redox initiator system is used to initiate polymerization from the surface of the substrate. The redox initiator system typically includes a pair of initiators: an oxidant and a reducing agent. The redox chemistry described herein can be modified to prepare non-fouling polymeric materials, for example, such as zwitterionic polymeric materials. Redox initiation is regarded as a one-electron transfer reaction to effectively generate free radicals under mild conditions. Suitable oxidants include, but are not limited to, peroxide, hydroperoxide, persulfates, peroxycarbonates, peroxydisulfates, peroxydiphosphate, permanganate, salts of metals such as Mn(III), Ce(IV), V(V), Co(III), Cr(VI) and Fe(III).

Suitable reducing agents include, but are not limited to, metal salts such as Fe(II), Cr(II), V(II), Ti(III), Cu(II), and Ag(I) salts, and oxyacids of sulfur, hydroxyacids, alcohols, thiols, ketones, aldehydes, amine, and amides. For example, in some embodiments, the reducing agent is an iron(II) salt, such as iron(II) L-ascorbate, ferrous sulfate, iron(II) acetate, iron(II) acetylacetonate, iron(II) ethylenediammonium sulfate, iron(II) gluconate, iron(II) lactate, iron(II) oxalate, or iron(II) sulfate.

Polymerization can be initiated by radicals formed directly from the redox reaction and/or by macroradicals formed by the abstraction of a hydrogen atom from the substrate by the transient radicals formed during the redox reaction.

In one embodiment, the substrate is coated with a undercoating coating and the non-fouling material is grafted from the undercoating layer by redox polymerization. The undercoating coating contains oxidants or reducing agents. In a preferred embodiment, the undercoating layer contains one or more reducing agents, such as acids, alcohol, thiols, ketones, aldehydes, amines and amides. An oxidant is used to react with one or more functional groups of the undercoating layer to form radicals which initiate the graft from polymerization.

In a particular embodiment, the undercoating layer is a copolymer with pendant groups of aliphatic chains containing silanol and/or hydroxyl groups. Such materials can be used to form a undercoating layer on polymeric substrates, such as polyurethane (PU). An oxidant, such as a salt of Ce(IV), reacts with the hydroxyl group under mild conditions to form hydroxyl radicals in the undercoating layer to grow the zwitterionic polymers.

In still another embodiment, a pair of peroxides and metal salts (such as Fe(II) as used in the Fenton Reaction) is used in the redox polymerization to graft zwitterionic polymers from polymers such as polyurethane. Peroxides for use in the redox polymerization include diacyl peroxides, dialkyl peroxides, diperoxyketals, hydroperoxides, ketone peroxides, peroxydicarbonates, and peroxyesters. Exemplary diacyl peroxides include decanoyl peroxide, lauroyl peroxide, succinic acid peroxide, and benzoyl peroxide. Exemplary dialkyl peroxides include dicumyl peroxide, 2,5-di(t-butylperoxy)-2,5-dimethylhexane, t-butyl cumyl peroxide, a,a'-bis(t-butylperoxy)diisopropylbenzene mixture of isomers, di(t-amyl) peroxide, di(t-butyl)peroxide and 2,5-di(t-butylperoxy)-2,5-dimethyl-3-hexyne. Exemplary diperoxyketals include 1,1-di(t-butylperoxy)-3,3,5-trimethylcyclohexane, 1,1-di(t-butylperoxy)cyclohexane, 1,1-di(t-amylperoxy) cyclohexane, n-butyl 4,4-di(t-butylperoxy)valerate, ethyl 3,3-di-(t-amylperoxy)butanoate and ethyl 3,3-di-(t-butylperoxy)butyrate. Exemplary hydroperoxides include cumene hydroperoxide and t-butyl hydroperoxide. Exemplary ketone peroxides include methyl ethyl ketone peroxide mixture and 2,4-pentanedione peroxide. Exemplary peroxydicarbonates include di(n-propyl)peroxydicarbonate, di(sec-butyl)peroxydicarbonate, and di(2-ethylhexyl)peroxydicarbonate. Exemplary peroxyesters include 3-hydroxy-1,1-dimethylbutyl peroxyneodecanoate alpha-cumyl peroxyneodecanoate, t-amyl peroxyneodecanoate, t-butyl peroxyneodecanoate, t-amyl peroxypivalate, t-butyl peroxypivalate, 2,5-di(2-ethyl hexanoylperoxy)-2,5-dimethylhexane, t-amyl peroxy-2-ethyl hexanoate, t-butyl peroxy-2-ethyl hexanoate, t-amyl peroxyacetate, t-butyl peroxyacetate, t-butyl peroxyacetate, t-butyl peroxybenzoate, OO-(t-amyl) O-(2-ethylhexyl) monoperoxycarbonate, OO-(t-butyl)-O-isopropyl monoperoxycarbonate, OO-(t-butyl)-O-(2-ethylhexyl)monoperoxycarbonate, polyether poly-t-butylperoxy carbonate, and t-butyl peroxy-3,5,5-trimethylhexanoate.

Any of the aforementioned peroxides such as benzoyl peroxide, lauroyl peroxide, hydrogen peroxide, or dicumyl peroxide are imbibed into the polymer such as polyurethane by dipping the polymer into a peroxide solution in an organic solvent for a predetermined period of time and dried. The peroxide containing polymer is put into a solution of monomer. The redox polymerization is initiated by the addition of a reducing agent, for example salts of Fe(II), such as Fe(II) chloride, Fe(II) sulfate, ammonium Fe(II) sulfate, or Fe(II) gluconate, at room temperature or elevated temperature, to the monomer solution.

For modifying the surface of an article and/or surface graft polymerization, it has been found particularly useful to use hydrophobic-hydrophilic redox initiator pairs. For example, in one embodiment the hydrophobic member of a hydrophobic-hydrophilic redox initiator pair is incorporated into a hydrophobic substrate as previously described. The substrate surface is then treated with an aqueous polymerization mixture containing monomers, typically hydrophilic monomers, and the hydrophilic member of the redox pair. This method offers particular advantages when polymers are being grafted from components having exposed external and internal surfaces to be modified (such as catheters) and any substrate that cannot readily be exposed to light. Additionally, such a system tends to minimize the extent of non graft polymerization in the bulk polymerization mixture away from the polymerization mixture/substrate surface interface.

In a preferred embodiment, the hydrophilic-hydrophobic redox pair is a hydrophobic oxidizing agent/hydrophilic reducing agent pair wherein (i) the hydrophobic oxidizing agent is tert-amyl peroxybenzoate, O,O-t-Butyl-O-(2-ethylhexyl)mono-peroxycarbonate, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-Bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, 4,4-azobis(4-cyanovaleric acid), or 1,1'-Azobis(cyclohexanecarbonitrile), 2,2'-Azobisisobutyronitrile (AIBN) and (ii) the hydrophilic reducing agent is $Fe^{2+}$, $Cr^{2+}$, $V^{2+}$, $Ti^{3+}$, $Co^{2+}$, $Cu^+$, or an amine; transition metal ion complexes, e.g., copper (II) acetylacetonate, $HSO^{3-}$, $SO_3^{2-}$, $S_2O_3^{2-}$, or $S_2O_5^{2-}$. Exemplary combinations include any of the aforementioned peroxides and $Fe^{2+}$. In some preferred embodiments, benzoyl peroxide, dicumyl peroxide, or O,O-t-Butyl-O-(2-ethylhexyl)mono-peroxycarbonate are used in combination with $Fe^{2+}$.

In an alternative embodiment, the hydrophilic-hydrophobic redox pair is a hydrophilic oxidizing agent/hydrophobic reducing agent pair wherein (i) the hydrophilic oxidizing agent is peracetic acid, a persulfate such as potassium persulfate, $Fe^{3+}$, $ClO^{3-}$, $H_2O_2$, $Ce^{4+}$, $V^{5+}$, $Cr^{6+}$, or $Mn^{3+}$, or their combinations; and (ii) the hydrophobic reducing agent is an alcohol, carboxylic acid, amine, or a boronalkyl or their combinations.

Other suitable redox systems include (1) organic-inorganic redox pairs, such as oxidation of an alcohol by $Ce^{4+}$, $V^{5+}$, $Cr^{6+}$, $Mn^{3+}$; (2) monomers which can act as a component of the redox pair, such as thiosulfate plus acrylamide, thiosulfate plus methacrylic acid, and N,N-dimethylaniline plus methyl methacrylate, and (3) boronalkyl-oxygen systems.

iv. Exemplary Initiators

Exemplary initiators include, but are not limited to, diacyl peroxides such as benzoyl peroxide, dichlorobenzoyl peroxide, dilauroyl peroxide, didecanoyl peroxide, diacetyl peroxide succinic acid peroxide, disuccinic peroxide and di(3,5,5-trimethylhexanoyl)peroxide. In a preferred embodiment, the diacyl peroxide is an aromatic diacyl peroxide, such as benzoyl peroxide.

Other exemplary initiators include, but are not limited to, peroxydicarbonates such as diethyl peroxydicarbonate, di-n-butyl peroxydicarbonate, diisobutyl peroxydicarbonate, di-4-tert-butylcyclohexyl peroxydicarbonate, di-sec-butyl peroxydicarbonate, di-2-ethylhexyl peroxydicarbonate, di-n-propyl peroxydicarbonate and diisopropyl peroxydicarbonate; peroxyesters, such as t-butyl perneodecanoate, t-butyl and t-amyl peroxy 2-ethyl hexanoate, and t-butyl peroxybenzoate; monoperoxycarbonates based on t-butyl and t-amyl monoperoxy 2-ethylhexyl carbonates; persulfates, such as potassium persulfate, ammonium persulfate, and sodium persulfate; cumene hydroxide, tert-butyl hydroperoxide, di(tert-amyl) peroxide, tert-butyl peroxide, 2,5-Bis(tert-butylperoxy)-2,5-dimethylhexane, 1,1-Bis(tert-butylperoxy)-3,3,5-trimethylcyclohexane; 1,1-Bis(tert-amylperoxy)cyclohexane, 1,1-Bis(tert-butylperoxy)-3,3,5-trimethylcyclohexane, 1,1-Bis(tert-butylperoxy)cyclohexane, 2,2-Bis(tert-butylperoxy)butane, 2,4-Pentanedione peroxide, 2,5-Bis(tert-butylperoxy)-2,5-dimethylhexane, 2,5-Di(tert-butylperoxy)-2,5-dimethyl-3-hexyne, 2-Butanone peroxide, cumene hydroperoxide, di-tert-amyl peroxide, dicumyl peroxide, lauroyl peroxide, tert-butyl peracetate, tert-butyl peroxide, tert-butyl peroxybenzoate, tert-butylperoxy 2-ethylhexyl carbonate, tert-Butylperoxy isopropyl carbonate, 4-nitro-benzenecarboperoxoic acid t-butyl ester, cyclohexanone peroxide, [(methylperoxy)(diphenyl)methyl]benzene, bis(t-butylcyclohexyl)peroxydicarbonate, and 2, 4, 6-triphenylphenoxyl dimer. For substrates requiring coating on both internal and external surfaces, additional considerations are required for initiating polymerization. Thermal initiators can be used; however, the elevated temperature typically required can adversely affect the substrate material. UV based approaches must be designed such that they can penetrate through the material or can be applied intralumenally, for instance from a fiber optic source threaded into the lumen. This may be achieved by selecting a photoactive initiator which is labile at a UV wavelength not absorbed by the substrate polymer. Generally, lower wavelength UV irradiation is less absorbed and penetrates more readily than higher wavelength UV.

In contrast, redox chemistries generally do not require a direct line of sight to a light source to initiate polymerization since polymerization is not initiated photolytically and therefore may be advantageous for coating substrates that have one or more surfaces that are difficult to expose to the UV source, such as catheter lumens. Further, redox polymerization typically can be done at low temperatures, for example less than 60° C., less than 55° C., less than 50° C., less than 45° C., less than 40° C., less than 35° C., or less than 30° C.

The graft from polymerization can propagate through a cationic or anionic reaction, where the substrate surface acts as the cation or anion initiator or a cationic or anionic initiator is immobilized on the substrate and the monomer contains a reactive olefin. Examples of anionic polymerization are anionic ring opening, as in the case of synthesizing polycaprolactone or polycaprolactam, where the polymerization proceeds through a lactone or lactam moiety in a ring structure containing a pendant zwitterion group. Alternatively, an organic ring containing one or more units of unsaturation and a pendant zwitterionic group are polymerized. In one embodiment a pendant olefin is included in the monomer unit and is used for crosslinking, such as in ring opening metathesis polymerization (ROMP).

Bioactive Agents

Therapeutics, diagnostic, and/or prophylactic agents can be immobilized on or otherwise incorporated into an article of the present invention. When optionally included, such bioactive agents may be leachable or non-leachable. For example, the bioactive agent may be dissolved or otherwise contained within the substrate, or covalently or non-covalently associated with the grafted polymer layer, and leached or otherwise disassociated with the article in a controlled or uncontrolled manner (e.g., by leaching). These agents can interact passively or actively with the surrounding in vivo environment. The agents can also be used to alter the surrounding in vivo chemistry or environment. Two or more agents can be immobilized to a substrate surface, wherein the activity of the two agents is greater than either of the agents alone. A substance, material or agent that is not considered active, can become active if an active agent is immobilized on the substance, material or agent. Active agents include, but are not limited to inorganic compounds, organometallic compounds, organic compounds or any synthetic or natural, chemical or biological compounds of known or unknown therapeutic effect.

In general, a bioactive agent can be immobilized covalently or non-covalently directly on the substrate, on the undercoating layer, on the grafted polymer layer, or combinations thereof. In one embodiment, the bioactive agent is immobilized covalently by reacting one or more functional groups on the active agent with one or more functional groups on the substrate, undercoating layer, and/or grafted polymer layer.

Covalent bonds can be formed by a variety of reaction mechanisms including, but not limited to, substitution, addition, and condensation reactions.

Typically, the bioactive agent will typically be immobilized on the grafted polymer layer after the grafted polymer layer has been grown from the surface. In an alternative embodiment, the bioactive agent can be co-immobilized with the grafted polymer layer in a side by side structure. In the graft from methods, a tether can be grown from the surface and the active agent immobilized on the tether. Alternatively, the active agent can be immobilized directly on the surface without the use of a tether.

Cell adhesion agents can be immobilized to the compositions described herein. The efficacy of a cell adhesion agent in binding cells in complex environments may be enhanced by reducing non-specific protein adsorption on the surface from which they are presented, given that cell attachment may be a competitive process with other protein adsorption. Further, there may an advantage to resisting attachment of any cells other than those specifically targeted by the cell adhesion agent to prevent competitive blocking of the surface.

Examples of desirable cell attachment agents include, but are not limited to, integrin binders. Exemplary integrin binders include, but are not limited to, RGD peptides, along with a number of variants that include RGD motifs, YIGSR peptides, fibronectin, laminin or other proteins or peptides. Longer variants of these peptide may have more specific target cell binding. Further, the ability to present locally dense concentrations of cell attachment agents may increase the effectiveness of cell attachment by creating multimeric interactions. Other cell adhesion agents include, but are not limited, to REDV peptides. Tailored integrin binders can be used for a variety of applications including osteointegration.

Cell adhesion agents that bind specific immune cells may also benefit from attachment to zwitterions. Adhesion of immune cells to the biomaterial surface activates these cells and prefaces their phenotypic response, such as the transition of monocytes to macrophages that can result, in some cases, in the fusion into undesirable foreign body giant cells. The inherent resistivity to random protein fouling that zwitterions possess provides a unique platform to couple biomolecules that act as specific ligands for immune cells including neutrophils, monocytes, helper T-cells, killer T-cells, suppressor T-cells, B-cells and dendritic cells. Selection of appropriate ligands may prime these cells for beneficial instead of detrimental functions. These ligands include peptides or proteins that specifically bind immune cell receptors such as integrins, selectins, complement, or Fc gamma. When bound to these cell-associated proteins, such ligands may stimulate intracellular signaling pathways that lead to responses including cytoskeletal rearrangements, production and secretion of molecules including chemokines, cytokines and other chemoattractants, and induction of apoptosis. Desirable behaviors that could be tailored by presentation of biomolecules via zwitterionic tethers may include prevention/reduction in the secretion of proinflammatory cytokines, enhancement of phagocytosis, and modulation of the release of soluble factors that influence tissue-device integration.

Osteointegration may also be promoted or induced by factors which would benefit from the non-fouling properties and stable presentation of non-fouling materials, such as zwitterions. Osteointegration promoting agents include, but are not limited to, bone-morphogenic proteins, such as BMP2 and shortened analogues thereof. Non-fouling surfaces, such as zwitterionic surfaces, may enhance the activity of agents designed to promote desired cell regrowth over a surface. Reducing attachment of neutrophils and macrophages may inhibit the foreign body response and enable desired cell attachment and growth process to be favored.

Presentation of antithrombotic agents may also be more effective when tethered to grafted polymers, such as zwitterionic materials, relative to other tethers. The process of thrombosis involves both surface and bulk pathways. Zwitterions have shown an ability to reduce platelet attachment and activation, reducing one pathway. Combining an active antithrombotic that assists in the reduction of platelet activation or directly targets additional pathways for thrombosis with a zwitterionic tether could enhance the antithrombotic effect compared to either a non-platelet adherent surface or the antithrombotic agent alone. Suitable antithrombotic agents include, but are not limited to, thrombomodulin, heparin, heparin fragments, derivatized heparin fragments, hyaluronic acid, reversible albumin binders, tissue plasminogen activator binders, transglutimase, reversible NO binders, polylysine, sulphonated polymers, thrombin inhibitors including hirudin, urokinase, and streptokinase.

Device-centered infection remains a large problem. Non-fouling materials, such as zwitterions materials, can by themselves diminish microbial adhesion and retard biofilm development. Prevention of microbial adhesion and biofilm can be further enhanced on non-fouling surfaces, such as zwitterionic surfaces, by presentation of antimicrobials including, but not limited to, membrane-targeting antimicrobial agents, antimicrobial peptides and small molecule antimicrobial agents. Generally, antimicrobial peptides are cationic molecules with spatially separated hydrophobic and charged regions. Exemplary antimicrobial peptides include linear peptides that form an α-helical structure in membranes or peptides that form β-sheet structures, optionally stabilized with disulfide bridges in membranes. Representative antimicrobial peptides include, but are not limited to, cathelicidins, defensins, dermcidin, and more specifically magainin 2, protegrin, protegrin-1, melittin, LL-37, dermaseptin 01, cecropin, caerin, ovispirin, cecropin A melittin hybrid, and alamethicin, or hybrids or analogues of other AmPs. Naturally occurring antimicrobial peptides include peptides from vertebrates and non-vertebrates, including plants, humans, fungi, microbes, and insects.

Antimicrobial peptides can be made from naturally occurring amino acids, non-naturally occurring amino acids (e.g., synthetic or semisynthetic amino acids and peptidomimetics), or combinations thereof. Antimicrobial peptides which retain their activity when immobilized on a surface are generally referred to as membrane-targeting antimicrobial agents. Antimicrobial peptides can be immobilized on the non-fouling grafted polymer layer, the substrate, the undercoating or combinations thereof by reacting a functional group on the peptide with a functional group on the non-fouling grafted polymer layer, the substrate, and/or the primer coat. For example, the peptide can be designed to have a cysteine residue which can be used to immobilize the peptide on a surface by reacting the thiol group of the cysteine residue with a thiol-reactive group on the surface.

Tethering of these agents via non-fouling materials, such as zwitterions, should provide stable, long-term activity. Additionally, immobilization of enzymes that degrade bacterial attachment and biofilm proteins, such as glycosylases, lyases, and serine-proteases, or those that degrade microbial communication signal molecules, such as N-acyl-homoserine lactone acylases, could provide improved efficacy in prevention of initial microbial adhesion events and subsequent biofilm formation.

A broad range of antimicrobial or antiseptic agents may be incorporated in the substrate or the non-fouling polymer to enhance antimicrobial activity at the surface or be released to provide antimicrobial activity in the environment surrounding the article. Suitable agents include silver metals, silver salts such as silver sulfadiazine, silver oxide, silver carbonate, silver acetate, silver alginate, silver azide, silver citrate, silver lactate, silver nitrate, silver sulfate, silver chloride, silver thiocyanate, silver-sodium-hydrogen-zirconium phosphate, silver sulfadiazine, silver cyclohexanediacetic acid and disilver 2,5-dichloro-3,6-dihydroxy-2,5-cyclohexadiene-1,4-dione, among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidoneiodine, parachlorometaxylene, gramicidin, polymixin, norfloxacin, tobramycin, sulfamylon, polyhexamethylene biguanide, alexidine, iodine, rifampicin, miconazole, bacitracin, and minocycline, ciprofloxacin, clindamycin, erythromycin, gentamycin, tetracycline and vancomycin.

Biguanide compounds which may be used according to the invention include poly(hexamethylene biguanide) hydrochloride and chlorhexidine compounds. Chlorhexidine is the term denoting the chemical compound 1,6bis(N-5-p-chlorophenyl-N1-biguanido)hexane). Chlorhexidine compounds include chlorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine diisophthalate, chlorhexidine di-2-hydroxy-napthoate, and chlorhexidine embonate.

Bismuth salts which may be used according to the invention include bismuth nitrate, bismuth citrate, bismuth salicylate, bismuth borate, bismuth mandelate, bismuth palmitate, bismuth benzoate, and bismuth sulfadiazine.

Cerium salts which may be used according to the invention include cerium nitrate and other cerium salts having a water solubility similar to cerium nitrate.

The term silver-containing compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraminobenzoate, silver paraminosalicylate, silver acetylsalicylate, silver ethylenediaminetetraacetic acid ("Ag EDTA"), silver picrate, silver protein, silver citrate, silver lactate and silver laurate.

Zinc salts which may be used according to the invention include zinc acetate and other zinc salts having a water solubility similar to zinc acetate.

The classes of bioactive agents identified above may be incorporated in the substrate or the non-fouling polymer to enhance antimicrobial activity at the surface or be released to provide antimicrobial activity in the environment surrounding the article.

Additional groups/classes of bioactive agents may be incorporated in the substrate or the non-fouling polymer to enhance antimicrobial activity at the surface or be released to provide antimicrobial activity in the environment surrounding the article and include the following groups/classes:

Antipyretics, analgesics and antiphlogistics (such as indometacin, acetylsalicylic acid, diclofenac sodium, ketoprofen, ibuprofen, mefenamic acid, azulene, phenacetin, isopropyl antipyrine, acetaminophen, benzadac, phenylbutazone, flufenamic acid, acetylsalicylic acid (aspirin), paracetamol, phenazone, sodium salicylate, salicylamide, sazapyrine, and etodolac) Opioid analgesics (such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine) Non-selective COX inhibitors such as salicylic acid derivatives, aspirin, sodium salicylate, choline magnesium trisalicylate, salsalate, diflunisal, sulfasalazine and olsalazine). Para-aminophenol derivatives such as acetaminophen. Indole and indene acetic acids such as indomethacin and sulindac. Heteroaryl acetic acids such as tolmetin, dicofenac and ketorolac. Arylpropionic acids such as ibuprofen, naproxen, flurbiprofen, ketoprofen, fenoprofen and oxaprozin. Anthranilic acids (fenamates) such as mefenamic acid and meloxicam. Enolic acids such as the oxicams (piroxicam, meloxicam). Alkanones such as nabumetone. Selective COX-2 Inhibitors (such as diaryl-substituted furanones such as rofecoxib; diaryl-substituted pyrazoles such as celecoxib; indole acetic acids such as etodolac and sulfonanilides such as nimesulide);

Anti-inflammatory steroids (such as cortisone, hydrocortisone, prednisone, dexamethasone, methylprednisolone, triamcinolone, beclomethasone, flunisolide, fluticasone proprionate, triamcinolone acetonide, budesonide, loterednol etabonate, mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone and their derivatives);

Antiulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride);

Coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride);

Peripheral vasodilators (such as ifenprodil tartrate, cinepacide maleate, ciclandelate, cynnaridine and pentoxyphylin);

Antibiotics (such as ampicillin, amoxicillin, cefalexin, cephalexin, cefoxytin and cephalothin, erythromcmethyl succinate, vacampicillin hydrochloride, minocycline hydrochloride, chloramphenicol, tetracycline, erythromycin, ceftazidime, cefuroxime sodium, aspoxicillin chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, timidazole, fusidic acid, trimethoprim, and 2-thiopyridine N-oxide);

Synthetic antimicrobials (such as nalidixic acid, piromidic acid, pipemidic acid trihydrate, enoxacin, cinoxacin, of loxacin, norfloxacin, ciprofloxacin hydrochloride and sulfamethoxazole-trimethoprim);

Antiviral agents (such as acyclovir, ganciclovir, acyclovir prodrugs, famcyclovir, zidovudine, didanosine, stavudine, lamivudine, zalcitabine, saquinavir, indinavir, ritonavir, n-docosanol, tromantadine and idoxuridine);

Anticonvulsants (such as propantheline bromide, atropine sulfate, oxitropium bromide, timepidium bromide, scopolamine butylbromide, trospium chloride, butropiumbromide, N-methylscopolaminemethylsulfate and methyloctatropine bromide);

Antitussives (such as tipepedine hibenzate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate);

Expectorants (such as bromhexine hydrochloride, carbocysteine, ethyl cysteine hydrochloride and methylcysteine hydrochloride);

Bronchodilators (such as theophylline, aminophylline, sodium cromoglicate, procaterol hydrochloride, trimetoquinol hydrochloride, diprophilline, salbutamol sulfate, clorprenaline hydrochloride, formoterol fumarate, ocriprenaline sulfate, pilbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride), (13) cardiotonics (such as dopamine hydrochloride, dobutamine hydrochloride, docarpamine, denopamine, caffeine, digoxin, digitoxin and ubidecarenone);

Diuretics (such as furosemide, acetazolamide, triclormethiazide, methylclothiazide, hydrochlorothiazide, hydroflumethiazide, ethiazide, cyclopenthiazide, spironolactone, triamterene, florothiazide, piretanide, mefruside, etacrynic acid, azosemide and clofenamide);

Muscle relaxants (such as chlorphenesin carbamate, tolperisone hydrochloride, eperisone hydrochloride, tizanidine hydrochloride, mefenicine, chlorzoxazone, phenprobamate, methocarbamol, chlormezazone, pridinol mesilate, afloqualone, baclofen and dantrolene sodium);

Cerebral metabolism ameliorants (such as nicergoline, meclofenoxate hydrochloride and taltirelin);

Minor tranquilizers (such as oxazolam, diazepam, clotiazepam, medazepam, temazepam, fludiazepam, meprobamate, nitrazepam and chlordiazepoxide);

Major tranquilizers (such as sulpiride, clocapramine hydrochloride, zotepine, chlorpromazine and haloperidol);

Beta-blockers (such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumorol hydrochloride, indenolol hydrochloride, timolol maleate, befunolol hydrochloride and bupranolol hydrochloride);

Antiarrthymics (such as procainamide hydrochloride, diso-pyramide, ajmaline, quinidine sulfate, aprindine hydrochloride, propafenone hydrochloride, mexiletine hydrochloride and azmilide hydrochloride);

Athrifuges (such as allopurinol, probenicid, colchicine, sulfinpyrazone, benzbromarone and bucolome);

Anticoagulants/Antiplatelets (such as heparin, chondroiten sulfate ticlopidine hydrochloride, dicumarol, potassium warfarin, and (2R,3R)-3-acetoxy-5-[2-(dimethylamino)ethyl]-2,3-dihydro-8-methyl-2-(4-methylphenyl)-1,5-benzothiazepin-4(5H)-onemaleate);

Thrombolytics (such as stretokinase, urokinase and tissue plasminogin activators, methyl (2E,3Z)-3-benzylidene-4-(3,5-dimethoxy-α-methylbenzylidene)-N-(4-methylpiperazin-1-yl)-succinamate hydrochloride);

Liver disease drugs (such as (±)r-5-hydroxymethyl-t-7-(3, 4-dimethoxyphenyl)-4-oxo-4,5,6,7-tetrahydro-obenzo[b]furan-c-6-carboxylactone);

Antiepileptics (such as phenyloin, sodium valproate, metalbital and carbamazepine);

Antihistamines (such as chlorpheniramine maleate, clemastine fumarate, mequitazine, alimemazine tartrate, cyproheptadine hydrochloride and bepotastin besilate);

Antiemitics (such as difenidol hydrochloride, metoclopramide, domperidone and betahistine mesilate and trimebutine maleate);

Depressors (such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy]ethoxy]-5-(4-methylphenyl)-4-pyrimidinyl]-4-(2-hydroxy-1,1-dimethyl-ethyl)benzenesulfonamide sodium);

Hyperlipidemia agents (such as pravastatin sodium and fluvastatin sodium);

Sympathetic nervous stimulants (such as dihydroergotamine mesilate and isoproterenol hydrochloride, etilefrine hydrochloride);

Oral diabetes therapeutic drugs (such as glibenclamide, tolbutamide and glimidine sodium);

Oral carcinostatics (such as malimastat);

Alkaloid narcotics (such as morphine, codeine and cocaine);

Vitamins (such as vitamin B1, vitamin B2, vitamin B6, vitamin B12, vitamin C and folic acid);

Thamuria therapeutic drugs (such as flavoxate hydrochloride, oxybutynin hydrochloride and terolidine hydrochloride);

Angiotensin converting enzyme inhibitors (such as imidapril hydrochloride, enalapril maleate, alacepril and delapril hydrochloride);

Non-steroidal anti-inflammatory agents (including their racemic mixtures or individual enantiomers where applicable) (such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate);

Antineoplastic/antiangiogenic (such as acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof);

Immunosuppressant agents (such as cyclosporine A, mycophenolic acid, tacrolimus, rapamycin, rapamycin analogues, azathioprine, recombinant or monoclonal antibodies to interleukins, T-cells, B-cells and/or their receptors);

Vasodilators (such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol);

Antiproliferative agents (such as paclitaxel, actinomycin D, rapamycin, tacrolimus, everolimus, dexamethasone and rapamycin analogues);

Local anaesthetics (such as benzocaine, bupivacaine, amethocaine, lignocaine, lidocaine, cocaine, cinchocaine, dibucaine, mepivacaine, prilocalne, etidocaine, veratridine (specific c-fiber blocker) and procaine);

Antifungals (such as amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaftate, triacetin, zinc, pyrithione and sodium pyrithione);

Agents/chemicals that block microbial attachment to target cells and/or inhibits entry of infectious pathogens (e.g., sulphated and sulponated polymers such as PC-515 (carrageenan), Pro-2000, and Dextrin 2 Sulphate);

Antiretroviral agents (e.g., PMPA gel) that prevent retroviruses from replicating in the cells;

Agents which change the condition of the tissue to make it hostile to the pathogen (such as substances which alter mucosal pH (e.g., Buffer Gel and Acidform);

Agents that treat or prevent an allergic or immune response and/or cellular proliferation (such as various cytokine inhibitors such as humanized anti-cytokine antibodies, anti-cytokine receptor antibodies, recombinant antagonists, or soluble receptors; various leucotriene modifiers such as zafirlukast, montelukast and zileuton; immunoglobulin E (IgE) inhibitors such as Omalizumab (an anti-IgE monoclonal antibody) and secretory leukocyte protease inhibitor) and SYK Kinase inhibitors);

Agents that prevent restenosis (such as paclitaxel, sirolimus, everolimus, vincristine, biolimus, mycophenolic acid, ABT-578, cervistatin, simvastatin, methylprednisolone, dexamethasone, actinomycin-D, angiopeptin, L-arginine, estradiol, 17-β-estradiol, tranilast, methotrexate, batimistat, halofuginone, BCP-671, QP-2, lantrunculin D, cytochalasin A, nitric oxide, and analogues and derivatives);

Growth factors and inflammatory cytokines involved in angiogenesis, fibroblast migration, fibroblast proliferation, ECM synthesis and tissue remodeling, such as epidermal growth factor (EGF) family, transforming growth factor-α (TGF-α), transforming growth factor-β (TGF-9-1, TGF-9-2, TGF-9-3, platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor—PlGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNF9), nerve growth factor (NGF), interferon-α, interferon-β, histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see e.g., U.S. Pat. No. 5,997,895), and tissue adhesives, such as cyanoacrylate and crosslinked poly(ethylene glycol)-methylated collagen compositions, such as described below. Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) Science: 242(4885); 1528 1534;

Other representative fibrosis-inducing agents include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291;

Anti-thrombotic and/or antiplatelet agents (include heparin, heparin fragments, organic salts of heparin, heparin complexes (e.g., benzalkonium heparinate, tridodecylammonium heparinate, heparin-tridodecylmethylammonium chloride, heparin-benzalkonium chloride, heparin-steralkonium chloride, heparin-poly-N-vinylpyrrolidone, heparin-lecithin, heparin-didodecyldimethylammonium bromide, heparin-pyridinium chloride, and heparin-synthetic glycolipid complex), dextran, sulfonated carbohydrates such as dextran sulphate, coumadin, coumarin, heparinoid, danaparoid, argatroban chitosan sulfate, chondroitin sulfate, danaparoid, lepirudin, hirudin, AMP, adenosine, 2-chloroadenosine, aspirin, phenylbutazone, indomethacin, meclofenamate, hydrochloroquine, dipyridamole, iloprost, streptokinase, and factor Xa inhibitors, such as DX9065a, magnesium, and tissue plasminogen activator. In one aspect, the anti-thrombotic agent is a modified heparin compound, such as a hydrophobically modified heparin or modified hirudin compound (e.g., stearylkonium heparin, benzalkonium heparin, cetylkonium heparin, or trdodecylmethyl ammonium heparin). Further examples of anti-thrombotic agents include plasminogen, lys-plasminogen, alpha-2-antiplasmin, urokinase, ticlopidine, clopidogrel, glycoprotein IIb/IIIa inhibitors such as abcixamab, eptifibatide, and tirogiban. Other agents capable of affecting the rate of clotting include glycosaminoglycans, danaparoid, 4-hydroxycourmarin, warfarin sodium, dicumarol, phenprocoumon, indan-1,3-dione, acenocoumarol, anisindione, and rodenticides including bromadiolone, brodifacoum, diphenadione, chlorophacinone, and pidnone);

Polypeptide drugs (such as but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; and peptide or polypeptide vaccines. Cell response modifiers. (Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers (such as the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin) Therapeutic enzymes (Such as proteases, phospholipases, lipases, glycosidases, cholesterol esterases, and nucleases) Peptide-nucleic acid (PNA) conjugate, polysaccharide-peptide conjugates such as glyosylated polypeptides; glycoproteins), a poly (ethyleneglycol)-polypeptide conjugate (PEG-ylated polypeptides), or polymer pharmaceuticals;

Antibodies and antibody fragments (such as, but are not limited to, therapeutic antibodies include trastuzumab, alemtuzumab, gemtuzumab, rituximab, ibritumomab, tositumomab, edrecolomab, cetuximab, bevacizumab, Ranibizumab, satumomab, pertuzumab, and daclizumab);

Therapeutic enzymes (such as recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase);

Enzyme inhibitors (such as edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol);

Steroids (such as glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fluorocortisone, fluorocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, fluorogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof);

Non-steroidal anti-inflammatory agents (including their racemic mixtures or individual enantiomers where applicable) (such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate).

Formulations of the above antimicrobial or antiseptic agents may be enhanced by altering the solubility or physical characteristics of the agent if salts or crystals are used, for instance by using nanoparticles or other formulations with reduced size or enhanced surface area per mass.

Non-fouling surfaces, such as zwitterionic surfaces, may also present a particularly attractive surface for immobilization of biomolecules, such as antibodies, for use as biosensors. Immobilized antibodies on non-fouling surface surfaces, such as zwitterionic surfaces, have been demonstrated to retain both antibody activity and antigen specificity in whole blood. "Smart" implanted medical devices that detect undesirable activation of specific immune pathways, such as proinflammatory cytokines, or the presence of a possible infectious agent, perhaps through detection of a secreted microbial toxin, could be designed, for example, by utilizing specific antibodies or biomolecules tailored to monitor these threats. Appropriate therapeutic strategies could then be employed before an unfavorable outcome, such as infection, arises. The stability of the zwitterionic molecule in vivo provides a unique advantage in this type of scenario due to its longevity.

Methods of Use

The materials described above may be in the form of a medical device or other article to which the non-fouling material is grafted. Suitable devices include, but are not limited to, surgical, medical or dental instruments, ophthalmic devices, wound treatments (bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, especially human tissue.

In one embodiment, the non-fouling materials are grafted directly from a fibrous material, incorporated into a fibrous material or grafted indirectly from a fibrous material (e.g., coated on a different surface coating). These include wound dressings, bandages, gauze, tape, pads, sponges, including woven and non-woven sponges and those designed specifically for dental or ophthalmic surgeries (See, e.g., U.S. Pat. Nos. 4,098,728; 4,211,227; 4,636,208; 5,180,375; and 6,711,879), paper or polymeric materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimize or eliminate contamination of the cultures, The non-fouling agents are also readily bound to particles, including nanoparticles, microparticles, millimeter beads, or formed into micelles, that have uses in a variety of applications including cell culture, as mentioned above, and drug delivery. Non-fouling, biocompatible, polymeric micelles would prevent protein denaturation preventing activation of the immune response allowing for a more stealthy delivery of the desired therapeutic.

The non-fouling material can also be applied directly to, or incorporated in, polymeric, metallic, or ceramic substrates. Suitable devices include, but are not limited to surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal, interventional, etc.), shunts, wound drains, dialysis membranes, infusion ports, cochlear implants, endotracheal tubes, guide wires, fluid collection bags, sensors, wound treatments (dressings, bandages, sutures, cell scaffolds, bone cements, particles), ophthalmic devices including contact lenses, orthopedic devices (hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these. Preferably, the non-fouling coating herein does not significantly adversely affect the desired physical properties of the device including, but not limited to, flexibility, durability, kink resistance, abrasion resistance, thermal and electrical conductivity, tensile strength, hardness, and burst pressure.

In one embodiment, the substrate is a vascularly inserted catheter such as a peripherally inserted central catheter (PICC), central venous catheter (CVC) or hemodialysis catheter, venous valves, punctual plugs, and intra-ocular devices and implants.

In another embodiment, the substrate is a vascularly inserted catheter formed from a medical grade polyurethane or CARBOTHANE® or formed from a material coated with a medical grade polyurethane or polycarbothane.

In one specific embodiment, the catheter comprises an elongated catheter body containing multiple lumens. For example, the catheter may be a double-lumen or a triple-lumen catheter. The lumens may be coaxial or side-by-side. In one exemplary embodiment, the catheter body has two side-by-side lumens, each having a "D" shape and the catheter body has a length that is greater than 5 cm; typically the catheter body of such catheters have a length of at least 11 cm. In one particularly preferred embodiment, the catheter body is a medical-grade polycarbonate-based aliphatic and aromatic polyurethane.

The non-fouling materials can also be added to paints and other coatings and filters to prevent mildew, bacterial contamination, and in other applications where it is desirable to prevent fouling, such as marine applications (ship hull coatings), contact lenses, dental implants, coatings for in vivo sensors, devices for separations, such as membranes for microbial suspension, biomolecule separation, protein fractionation, cell separation, waste water treatment, bioreactors, and food processing.

Other applications include the treatment of fibers, particulates and films for applications in textiles, additives, electric/optical appliances, carbon nanotubes, packaging materials and colorants/inks.

Independent of any theory, articles of the present invention having a treated surface and a grafted polymer layer exhibit low fibrinogen adsorption in a fibrinogen adsorption assay. In general, the treated surface and the grafted polymer layer, in combination, constituting a modified surface, exhibits a fibrinogen adsorption of less than 125 $ng/cm^2$ in a fibrinogen adsorption assay in which samples are incubated for 60 minutes at 37° C. in 70 µg/mL fibrinogen derived from human plasma, and the amount of adsorbed fibrinogen is determined using a standard protocol, preferably by using radiolabled fibrinogen. For example, in one such embodiment, the modified surface exhibits a fibrinogen adsorption of less than 90 $ng/cm^2$ in such an assay. By way of further example, in one such embodiment, the modified surface exhibits a fibrinogen adsorption of less than 70 $ng/cm^2$ in such an assay. By way of further example, in one such embodiment, the modified surface exhibits a fibrinogen adsorption of less than 50 $ng/cm^2$ in such an assay. By way of further example, in one such embodiment, the modified surface exhibits a fibrinogen adsorption of less than 30 $ng/cm^2$ in such an assay. By way of further example, in one such embodiment, the modified surface exhibits a fibrinogen adsorption of less than 20 $ng/cm^2$ in such an assay. By way of further example, in one such embodiment, the modified surface exhibits a fibrinogen adsorption of less than 15 $ng/cm^2$ in such an assay. By way of further example, in one such embodiment, the modified surface exhibits a fibrinogen adsorption of less than 12 $ng/cm^2$ in such an assay. By way of further example, the treated surface and the grafted polymer layer, in combination, constituting a low-fouling surface, exhibits a fibrinogen adsorption of less than 10 $ng/cm^2$ in such an assay. By way of further example, the treated surface and the grafted polymer layer, in combination, constituting a low-fouling surface, exhibits a fibrinogen adsorption of less than 8 $ng/cm^2$ in such an assay. More preferably, the treated surface and the grafted polymer layer, in combination, constituting a low-fouling surface, exhibits a fibrinogen adsorption of less than 6 $ng/cm^2$ in such an assay. Still more preferably, the treated surface and the grafted polymer layer, in combination, constituting a low-fouling surface, exhibits a fibrinogen adsorption of less than 4 $ng/cm^2$ in such an assay. Still more preferably, the treated surface and the grafted polymer layer, in combination, constituting a low-fouling surface, exhibits a fibrinogen adsorption of less than 2 $ng/cm^2$ in such an assay. In certain embodiments, the treated surface and the grafted polymer layer exhibits a fibrinogen adsorption of less than 1 $ng/cm^2$ in such an assay; for example, in one embodiment, the grafted polymer layer exhibits a fibrinogen adsorption of less than 0.5 $ng/cm^2$ in such an assay, and more preferably less than 0.25 $ng/cm^2$ in such an assay. In one embodiment, the grafted polymer in each of the foregoing examples recited in this paragraph is a zwitterionic polymer. In one embodiment, the grafted polymer in each of the foregoing examples recited in this paragraph is a polymer containing sulfobetaine or carboxybetaine repeat units. In one embodiment, the grafted polymer in each of the foregoing examples recited in this paragraph is a zwitterionic polymer and the zwitterionic polymer is grafted from a polyurethane polymer. In one embodiment, the grafted polymer in each of the foregoing examples recited in this paragraph is a polymer containing sulfobetaine or carboxybetaine repeat units and the polymer containing sulfobetaine or carboxybetaine repeat units is grafted from a polyurethane polymer. In one embodiment, the treated surface exhibits a fibrinogen adsorption of <125 ng/cm$^2$, <90 ng/cm$^2$, <70 ng/cm$^2$, <50 ng/cm$^2$, <30 ng/cm$^2$, <20 ng/cm$^2$, <15 ng/cm$^2$, <12 ng/cm$^2$, <10 ng/cm$^2$, <8 ng/cm$^2$, <6 ng/cm$^2$, <4 ng/cm$^2$, <2 ng/cm$^2$, <1 ng/cm$^2$, <0.5 ng/cm$^2$, or <0.25 ng/cm$^2$.

Preferred embodiments also show reduction in thrombus. For example, thrombus reduction of treated and modified substrates can be assessed relative to unmodified substrates that are otherwise substantially identical by exposing them to freshly harvested bovine blood, heparinized, with radiolabeled platelets, in a flow loop for 2 hours. As an assessment of anti-thrombogenic performance, samples are placed in an ex-vivo flow loop model of thrombosis. Anti-thrombogenic activity can be evaluated using ex-vivo flow loop model of thrombosis. Briefly, up to 10 liters of fresh blood are collected from a single animal. This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for substrate containing a lumen by connecting the two ports of the substrate through a 2nd peristaltic pump. The size of tubing into which the article is placed and speed of the bloodflow may be adjusted based on the size of the article being tested. Preferably, when the articles are 14-15.5 French dialysis catheters, they are placed in a flow loop circuit with tubing diameter of approximately 12.5-25.4 mm inner diameter. Blood is pumped in the outer circuit at a rate of approximately 2.5 L/min, while blood in the inner circuit is pumped at a rate of approximately ~200-400 mL/min. When the articles are 5 French PICC catheter shafts, they are placed in a flow loop circuit of approximately 6.4 mm inner diameter and blood flow rate is approximately 200 mL/min. The lumens may be locked with a solution, for example saline, during evaluation. Alternatively, the distal tip may be sealed, for example with epoxy, during evaluation. When the articles are 10 French rods, they are placed in a flow loop circuit of approximately 6.4 mm inner diameter and blood flow rate is approximately 200 mL/min. After 60-120 minutes, the articles are removed, inspected visually for thrombus formation, and adhered platelets are quantified using a Gamma counter. For samples not containing a lumen, only an outer circuit may be used to measure thrombus on the outside of the device. Optionally, each of the ends of the articles may be trimmed up to 2 cm after blood exposure but before measuring adhered platelets to eliminate end effects. Optionally, but preferably, articles may be stored in solutions that contain PBS, citrated human plasma, fetal bovine serum, or adult human serum, for a period of 14, 30, 60, or 90 days prior to assessment of anti-thrombogenic performance.

Preferred embodiments show at least an 80% reduction relative to untreated and unmodified substrate in adsorbed platelets and substantial visual reduction of thrombus. Embodiments show a visual reduction of thrombus relative to untreated and unmodified substrate. Preferred embodiments show at least a 90% reduction in adsorbed platelets. Preferred embodiments show at least a 98% reduction in adsorbed platelets. Alternatively, in a preferred embodiment, the thrombogenecity is reduced relative to the untreated and unmodified substrate, after exposure to a 47% (w/v) sodium citrate solution in DI water for greater than 3 days. Embodiments show a visual reduction of thrombus relative to untreated and unmodified substrate. Preferred embodiments show at least an 80% reduction relative to untreated and unmodified substrate in adsorbed platelets and substantial visual reduction of thrombus. Preferred embodiments show at least a 90% reduction in adsorbed platelets. Preferred embodiments show at least a 98% reduction in adsorbed platelets. Alternatively, the thrombogenecity of preferred embodiments are reduced relative to the untreated and unmodified substrate after exposure to animal serum and/or plasma. For example, the thrombogenecity of preferred embodiments are reduced after 60 day exposure to citrated human plasma at 37° C. Embodiments show a visual reduction of thrombus relative to untreated and unmodified substrate. Preferred embodiments show at least an 80% reduction relative to untreated and unmodified substrate in adsorbed platelets and substantial visual reduction of thrombus. Preferred embodiments show at least a 90% reduction in adsorbed platelets. Preferred embodiments show at least a 98% reduction in adsorbed platelets.

Preferred embodiments show antibiofilm activity of at least 0.5 log, 1 log, 1.5 log, 2 log, 2.5 log, 3 log, or 4 log. More preferred embodiments have antibiofilm activity after extended exposures to PBS, serum, or plasma products. In one preferred embodiment, antibiofilm activity of 1 log is achieved after 30 days storage in PBS at 37° C. In a further preferred embodiment, antibiofilm activity of 1 log is achieved after 90 days storage in PBS at 37° C. In one preferred embodiment, antibiofilm activity of 2 log is achieved after 30 days storage in PBS at 37° C. In a further preferred embodiment, antibiofilm activity of 2 log is achieved after 90 days storage in PBS at 37° C. In one preferred embodiment, antibiofilm activity of 1 log is achieved after 30 days storage in citrated human plasma at 37° C. In a further preferred embodiment, antibiofilm activity of 1 log is achieved after 90 days storage in citrated human plasma at 37° C. In one preferred embodiment, antibiofilm activity of 2 log is achieved after 30 days storage in citrated human plasma at 37° C. In a further preferred embodiment, antibiofilm activity of 2 log is achieved after 90 days storage in citrated human plasma at 37° C. Optionally, but preferably, articles may be stored in solutions that contain PBS, citrated human plasma, fetal bovine serum, or adult human serum, for a period of 14, 30, 60, or 90 days prior to assessment of anti-thrombogenic performance.

Preferred embodiments show resistance to protein adsorption after extended exposure to PBS, which may indicate hydrolytic stability. In some embodiments, the treated surface and the grafted polymer layer, in combination, constituting a low-fouling surface, exhibits a fibrinogen adsorption of less than 50 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the treated surface and the grafted polymer layer, in combination, exhibits a fibrinogen adsorption of less than 20 ng/cm$^2$ in a fibrinogen adsorption assay in which samples are incubated for 60 minutes at 37° C. in 70 μg/mL fibrinogen derived from human plasma after 30 days exposure to PBS at 37° C. In some embodiments, the treated surface and the grafted polymer layer, in combination, exhibits a fibrinogen adsorption of less than 10 ng/cm$^2$ in a fibrinogen adsorption assay in which samples are incubated for 60 minutes at 37° C. in 70 μg/mL fibrinogen derived from human plasma after 30 days exposure to PBS at 37° C. Preferred embodiments show resistance to protein adsorption after extended exposure to PBS, which may indicate hydrolytic stability. In some embodiments, the treated surface and the grafted polymer layer, in combination, exhibits a fibrinogen adsorption of less than 30 ng/cm$^2$ in a fibrinogen adsorption assay in which samples are incubated for 60 minutes at 37° C. in 70 μg/mL fibrinogen derived from human plasma after 90 days exposure to PBS at 37° C. In some embodiments, the treated surface and the grafted polymer layer, in combination, exhibits a fibrinogen adsorption of less than 20 ng/cm² in a fibrinogen adsorption assay in which samples are incubated for 60 minutes at 37° C. in 70 μg/mL fibrinogen derived from human plasma after 90 days exposure to PBS at 37° C. In some embodiments, the treated surface and the grafted polymer layer, in combination, exhibits a fibrinogen adsorption of less than 10 ng/cm² in a fibrinogen adsorption assay in which samples are incubated for 60 minutes at 37° C. in 70 μg/mL fibrinogen derived from human plasma after 90 days exposure to PBS at 37° C.

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Removal of Surface BaSO₄ Particles by Treatment of Carbothane-BaSO₄ Rods with HCl and Modification with SBMA HCl treatment. Sectioned carbothane-BaSO₄ rods were treated with 1 N HCl over 3 nights, the HCl solution being exchanged with fresh HCl after the first 24 h period. The HCl solution was decanted and the rods were washed extensively with deionized water and dried. SEM pictures of the surface confirmed the removal of BaSO₄ particles.

Imbibing with DCP. The dried rods were imbibed with a solution of dicumylperoxide (10% in acetone) for 2 h, filtered, rinsed with acetone, and dried for 18 h.

SBMA modification. A degassed suspension of the dicumylperoxide imbibed samples were modified with SBMA monomer and Fe(II) reaction solution for 5 h. The solution was decanted, and the rods were washed with PBS. SBMA modification was confirmed by the presence of the peak corresponding to the sulfobetaine group in the IR spectrum and sectioned samples (1 cm sections with both ends trimmed) had an average 73% reduction in adsorbed radio labeled fibrinogen compared to unmodified carbothane-BaSO₄ rods.

Example 2

Reduction of Microbial Adhesion Post Incubation in Serum

Rods that were modified with SBMA following an acid treatment to remove surface BaSO₄ were incubated in 50% FBS over the course of 1, 30, and 90 d. At each interval the reduction in adherent *E. coli* bacteria using the mCDC assay, compared with unmodified control, was determined and are shown in the table below.

| Days Incubated in 50% FBS | E. Coli Log Reduction |
|---|---|
| 1 | 4.55 |
| 30 | 3.06 |
| 90 | 2.67 |

Example 3

Sonication to Reduce Surface Roughness and Surface Defects

Sonication of Tecothane 97A-30% BaSO₄ 5FR double D lumen tubing for up to 2 hours provides a smoother surface by Lext Ra evaluation and by visual examination. The sonication solvent is either water or alcohol at 42Kz. For solvent or water sonication, the Tecothane 97A-30% BaSO₄ 5FR double D lumen tubing is enclosed in a sealed glass jar of ethanol, or isopropyl alcohol or DI water. The jar is submerged into the sonication water bath. The sonication dwell cycle was 2 hours and held to ~20° C. using flowing tap water in and out of the sonication bath. The tubing was then analyzed post SBMA modification (SBMA modification using TBEC imbibing and iron(II) gluconate was as described elsewhere) by IR to confirm SBMA signal and also LEXT.

| Transverse Roughness - Outside - 50x Magnification Post SBMA Modification | |
|---|---|
| Pretreatment | Rq2 (um) |
| Control | 0.15 |
| No Sonication | 0.18 |
| 30 min Sonication | 0.16 |
| 2 hr Sonication w/Imbibe (in this example peroxide was added to the sonication solution) | 0.06 |
| 3 hr Sonication | 0.20 |

What is claimed is:

1. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm² in a fibrinogen binding assay in which the low-fouling surface is incubated for 60 minutes at 37° C. in a composition containing 70 μg/ml fibrinogen derived from human plasma and 1.4

µg/ml I-125 radiolabeled fibrinogen, wherein treating the substrate surface comprises contacting the substrate surface with a solution containing an acid, a base or a chelating agent to remove the second material from the substrate surface.

2. The process of claim 1, wherein the second material is an inorganic material.

3. The process of claim 1, wherein the second material comprises a metal, a ceramic, a glass, or a second polymeric material, and the second polymeric material has a chemical composition that differs from the first material.

4. The process of claim 1, wherein the second material is a radiopaque material.

5. The process of claim 1, wherein the second material is a radiopaque material comprising barium, bismuth, gold, tantalum or a combination thereof.

6. The process of claim 1, wherein the second material comprises barium sulfate, a bismuth salt, gold foil, tantalum or a combination thereof.

7. The process of claim 1, wherein the first material comprises a polyurethane polymer or a copolymer thereof.

8. The process of claim 1, wherein treating the substrate surface comprises contacting the substrate surface with a solution containing an acid to remove the second material from the substrate surface.

9. The process of claim 8, wherein the acid comprises hydrochloric acid, sulfuric acid, nitric acid, phosphoric acid, boric acid, hydrofluoric acid, hydrobromic acid, lactic acid, acetic acid, carbonic acid, formic acid, citric acid, oxalic acid, uric acid, a carboxylic acid, a sulfonic acid, sulfamic acid, or chlorous acid.

10. The process of claim 1, wherein treating the substrate surface comprises contacting the substrate surface with a solution containing a base to remove the second material from the substrate surface.

11. The process of claim 10, wherein the base comprises sodium hydroxide, potassium hydroxide, ammonia solution, or sodium chlorite.

12. The process of claim 1, wherein treating the substrate surface comprises contacting the substrate surface with a solution containing a chelating agent to remove the second material from the substrate surface.

13. The process of claim 12, wherein the chelating agent comprises water, glycine, beta-alanine, iminodiacetic acid (IDA), nitrilotriacetic acid (NTA), ethylenediaminetetraacetic acid, (EDTA), diethylene triamine pentaacetic acid (DTPA), 1,2-bis(o-aminophenoxy)ethane-N,N,N',N'-tetraacetic acid (BAPTA), or 1,4,7,10-tetraazacyclododecane-1,4,7,10-tetraacetic acid (DOTA).

14. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 µg/ml fibrinogen derived from human plasma and 1.4 µg/ml I-125 radiolabeled fibrinogen, wherein treating the substrate surface comprises polishing the substrate surface.

15. The process of claim 14, wherein the second material comprises a metal, a ceramic, a glass, or a second polymeric material, and the second polymeric material has a chemical composition that differs from the first material.

16. The process of claim 14, wherein the second material is a radiopaque material comprising barium, bismuth, gold, tantalum or a combination thereof.

17. The process of claim 14, wherein the first material comprises a polyurethane polymer or a copolymer thereof.

18. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 µg/ml fibrinogen derived from human plasma and 1.4 µg/ml I-125 radiolabeled fibrinogen, wherein treating the substrate surface comprises mechanically, chemically, or chemomechanically polishing the substrate surface.

19. The process of claim 18, wherein the second material comprises a metal, a ceramic, a glass, or a second polymeric material, and the second polymeric material has a chemical composition that differs from the first material.

20. The process of claim 18, wherein the second material is a radiopaque material comprising barium, bismuth, gold, tantalum or a combination thereof.

21. The process of claim 18, wherein the first material comprises a polyurethane polymer or a copolymer thereof.

22. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 µg/ml fibrinogen derived from human plasma and 1.4 µg/ml I-125 radiolabeled fibrinogen, wherein, after the surface is treated, the particles have an average particle size and a distribution such that the number density of the particles in the near-surface zone is less than the overall number density of the particles in the composite, the near-surface zone extends a distance, D, from the substrate surface and into the substrate, and D has a value that does not exceed twice the average particle size.

23. The process of claim 22 wherein the number density of the particles in the near-surface zone is less than 50% of the overall number density of the particles in the composite.

24. The process of claim 22 wherein the number density of the particles in the near-surface zone is less than 10% of the overall number density of the particles in the composite.

25. The process of claim 22 wherein the number density of the particles in the near-surface zone is less than 1% of the overall number density of the particles in the composite.

26. The process of claim 22, wherein the second material comprises a metal, a ceramic, a glass, or a second polymeric material, and the second polymeric material has a chemical composition that differs from the first material.

27. The process of claim 22, wherein the second material is a radiopaque material comprising barium, bismuth, gold, tantalum or a combination thereof.

28. The process of claim 22, wherein the first material comprises a polyurethane polymer or a copolymer thereof.

29. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 µg/ml fibrinogen derived from human plasma and 1.4 µg/ml I-125 radiolabeled fibrinogen, wherein the treated surface has a R$_{rms}$ surface roughness of no more than 100 nm and a surface defect density of less than 0.1 defects/µm$^2$ of defects having a size greater than 0.5 micrometers.

30. The process of claim 29, wherein the second material comprises a metal, a ceramic, a glass, or a second polymeric material, and the second polymeric material has a chemical composition that differs from the first material.

31. The process of claim 29, wherein the second material is a radiopaque material comprising barium, bismuth, gold, tantalum or a combination thereof.

32. The process of claim 29, wherein the first material comprises a polyurethane polymer or a copolymer thereof.

33. A process for preparing an article having a low-fouling surface on a substrate, the substrate having a surface, a bulk beneath the surface, and a near-surface zone lying between the surface and the bulk, the surface, near-surface zone and bulk containing a composite, the composite comprising a continuous phase of a first material and particles of a second material dispersed in the continuous phase, the first material being polymeric and the first and second material being different, the process comprising (a) treating the substrate surface to reduce the second material from the substrate surface and (b) forming a grafted polymer layer on the treated substrate surface, the treated surface and the grafted polymer layer, in combination, constituting a low-fouling surface having a fibrinogen adsorption of less than about 125 ng/cm$^2$ in a fibrinogen binding assay in which the low-fouling surface is incubated for 60 minutes at 37° C. in a composition containing 70 µg/ml fibrinogen derived from human plasma and 1.4 µg/ml I-125 radiolabeled fibrinogen, wherein the substrate surface is treated with a surfactant.

34. The process of claim 33, wherein the second material comprises a metal, a ceramic, a glass, or a second polymeric material, and the second polymeric material has a chemical composition that differs from the first material.

35. The process of claim 33, wherein the second material is a radiopaque material comprising barium, bismuth, gold, tantalum or a combination thereof.

36. The process of claim 33, wherein the first material comprises a polyurethane polymer or a copolymer thereof.

37. The process of claim 33, wherein the surfactant is an anionic surfactant.

38. The process of claim 37, wherein the anionic surfactant is ammonium lauryl sulfate, sodium lauryl sulfate, sodium laureth sulfate, sodium myreth sulfate, dioctyl sodium sulfosuccinate, perfluorooctanesulfonate, perfluorobutanesulfonate, alkyl aryl ether phosphate, alkyl ether phosphate, sodium stearate, sodium lauroyl sarcosinate, perfluorononanoate, or perfluorooctanoate.

39. The process of claim 33, wherein the surfactant is a cationic surfactant.

40. The process of claim 39, wherein the cationic surfactant is octenidine dihydrochloride, cetyl trimethylammonium bromide, cetyl trimethylammonium chloride, cetylpyridinium chloride, polyethoxylated tallow amine, benzalkonium chloride, benzethonium chloride, 5-bromo-5-nitro-1,3-dioxane, dimethyldioctadecylammonium chloride, or dioctadecyldimethylammonium bromide.

41. The process of claim 33, wherein the surfactant is a zwitterionic surfactant.

42. The process of claim 41, wherein the zwitterionic surfactant is 3-[(3-Cholamidopropyl)dimethylammonio]-1-propanesulfonate, cocamidopropyl hydroxysultaine, an amino acid; an imino acid; cocamidopropyl betaine, or lecithin.

43. The process of claim 33, wherein the surfactant is a nonionic surfactant.

44. The process of claim 43, wherein the nonionic surfactant is cetyl alcohol, stearyl alcohol, cetostearyl alcohol, oleyl alcohol, octaethylene glycol monododecyl ether, pentaethylene glycol monododecyl ether, a polyoxypropylene glycol alkyl ether, a glucoside alkyl ether, decyl glucoside, lauryl glucoside, octyl glucoside, a polyoxyethylene glycol octylphenol ether, Triton X-100, a polyoxyethylene glycol alkylphenol ether, Nonoxynol-9, glyceryl laurate, a polyoxyethylene glycol sorbitan alkyl ester, a polysorbate, a sorbitan alkyl ester, Spans, cocamide MEA, cocamide DEA, dodecyldimethylamine oxide, or block copolymers of polyethylene glycol and polypropylene glycol.

* * * * *